(12) United States Patent
Bertozzi et al.

(10) Patent No.: US 9,410,958 B2
(45) Date of Patent: Aug. 9, 2016

(54) ALKYNE-ACTIVATED FLUOROGENIC AZIDE COMPOUNDS AND METHODS OF USE THEREOF

(71) Applicant: The Regents of the University of California, Oakland, CA (US)

(72) Inventors: Carolyn R. Bertozzi, Berkeley, CA (US); Peyton Shieh, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/665,962

(22) Filed: Mar. 23, 2015

(65) Prior Publication Data

US 2015/0276752 A1   Oct. 1, 2015

Related U.S. Application Data

(60) Provisional application No. 61/970,200, filed on Mar. 25, 2014.

(51) Int. Cl.
| | | |
|---|---|---|
| G01N 33/58 | (2006.01) | |
| G01N 33/68 | (2006.01) | |
| G01N 33/50 | (2006.01) | |
| C09B 11/08 | (2006.01) | |
| C09B 11/24 | (2006.01) | |
| C12Q 1/02 | (2006.01) | |
| C07B 59/00 | (2006.01) | |
| C07F 7/08 | (2006.01) | |

(52) U.S. Cl.
CPC ............ *G01N 33/582* (2013.01); *C07F 7/0816* (2013.01); *C09B 11/08* (2013.01); *C09B 11/24* (2013.01)

(58) Field of Classification Search
CPC ..... G01N 33/582; G01N 33/58; G01N 33/68; G01N 33/50; C09B 11/08; C09B 11/24; C12Q 1/02; C07B 59/00
See application file for complete search history.

(56) References Cited

U.S. PATENT DOCUMENTS

| | | |
|---|---|---|
| 6,570,040 B2 | 5/2003 | Saxon et al. |
| 7,122,703 B2 | 10/2006 | Saxon et al. |
| 7,667,012 B2 | 2/2010 | Saxon et al. |
| 7,807,619 B2 | 10/2010 | Bertozzi et al. |
| 7,838,665 B2 | 11/2010 | Saxon et al. |
| 7,923,582 B2 | 4/2011 | Saxon et al. |
| 7,939,626 B2 | 5/2011 | Saxon et al. |
| 8,076,496 B2 | 12/2011 | Saxon et al. |
| 8,431,558 B2 | 4/2013 | Bertozzi et al. |
| 8,461,298 B2 | 6/2013 | Bertozzi et al. |
| 2013/0344527 A1 | 12/2013 | Bertozzi et al. |

FOREIGN PATENT DOCUMENTS

| | | |
|---|---|---|
| WO | WO 01/68565 | 9/2001 |
| WO | WO 2006/050262 | 5/2006 |

OTHER PUBLICATIONS

Shieh et al., J. Am. Chem. Soc., 2012, 134, 17428-17431.*
(Shieh et al.—2), Shieh et al., PNAS, 2014, vol. 111 No. 15, pp. 5456-5461.*
Shieh, et al.; "Fluorogenic Azidofluoresceins for Biological Imaging"; J. Am. Chem. Soc.: vol. 134, No. 42, pp. 17428-17431 (Oct. 24, 2012).

* cited by examiner

*Primary Examiner* — Sun Jae Yoo
(74) *Attorney, Agent, or Firm* — Bozicevic Field & Francis, LLP; Paula A. Borden; Glenn J. Foulds

(57) ABSTRACT

The present disclosure provides fluorogenic azide compounds. Also provided are methods of using the subject compounds for labelling a target biomolecule that includes an alkyne. In some embodiments, the method includes contacting the biomolecule with a fluorogenic azide compound, wherein the contacting results in covalent linkage of the compound with the alkyne moiety of the target biomolecule.

36 Claims, 28 Drawing Sheets

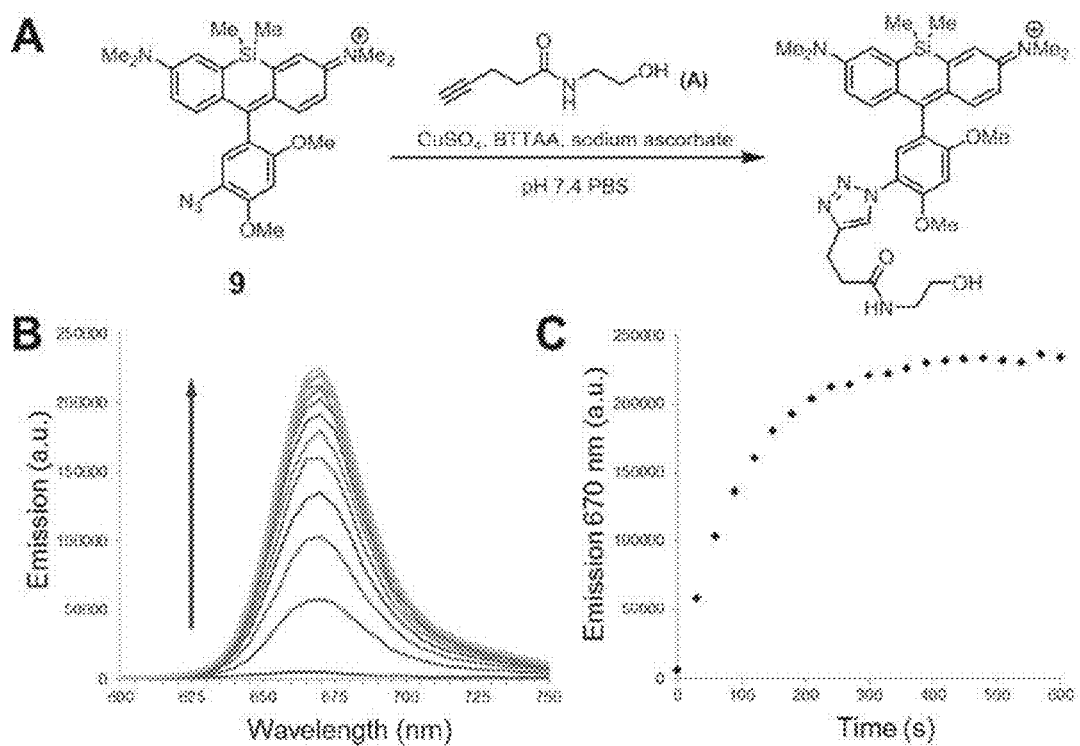
FIG. 4A-C
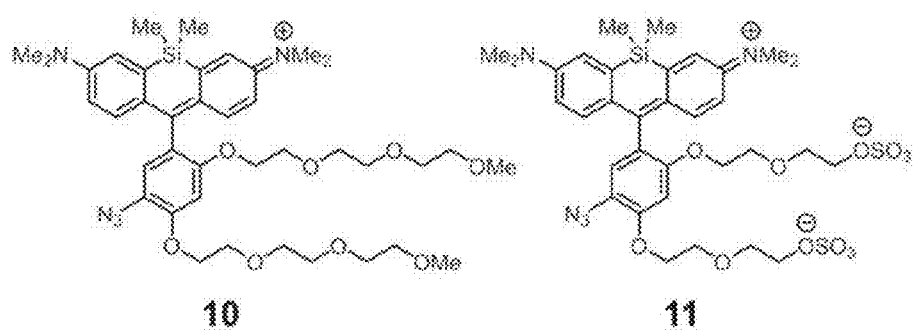
FIG. 5

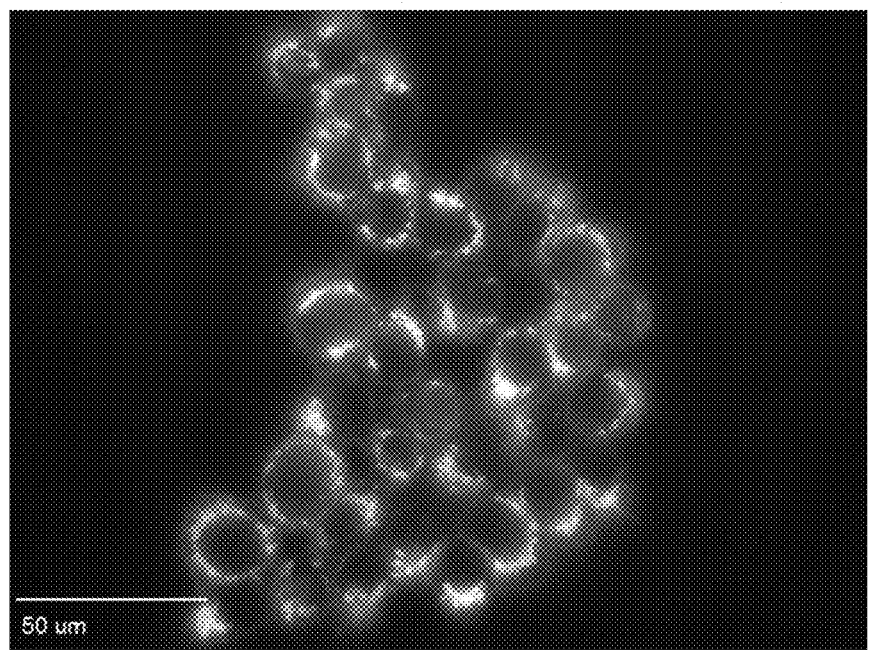
FIG. 15
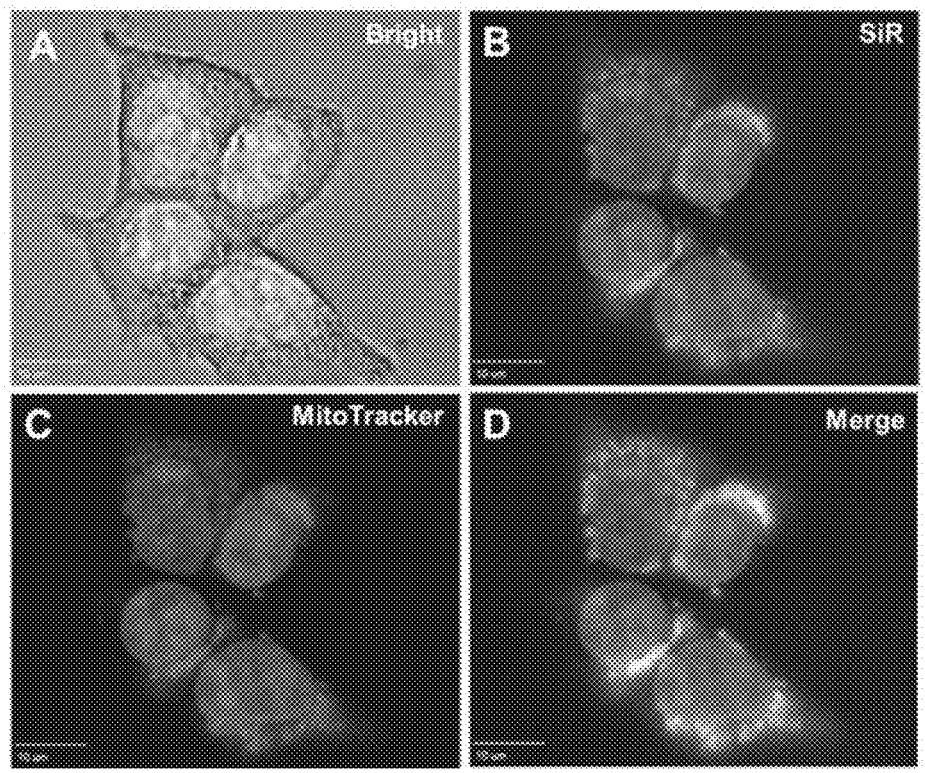
FIG. 16A-D

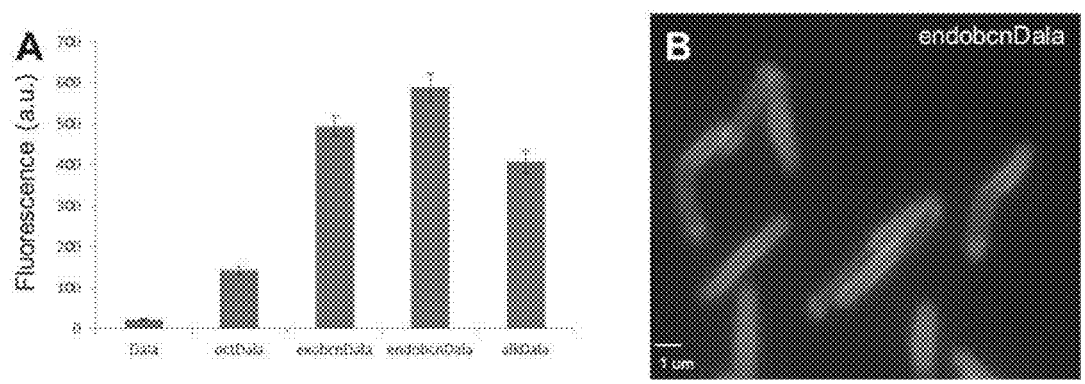
FIG. 19A-B
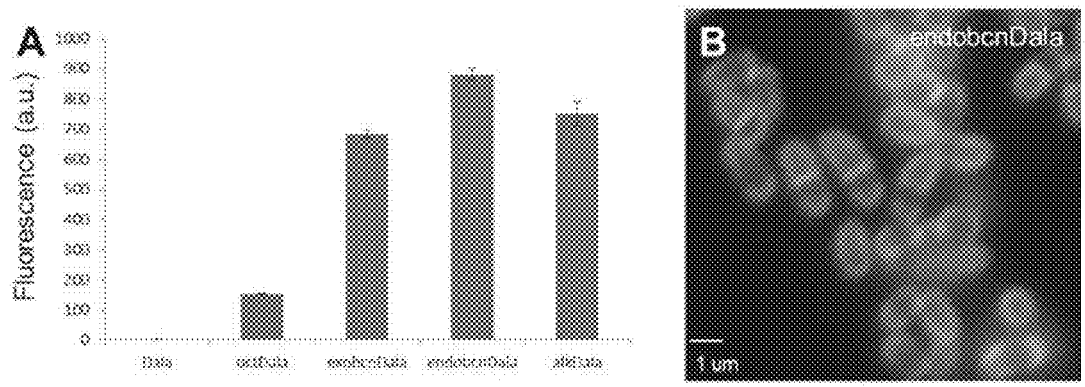
FIG. 20A-B

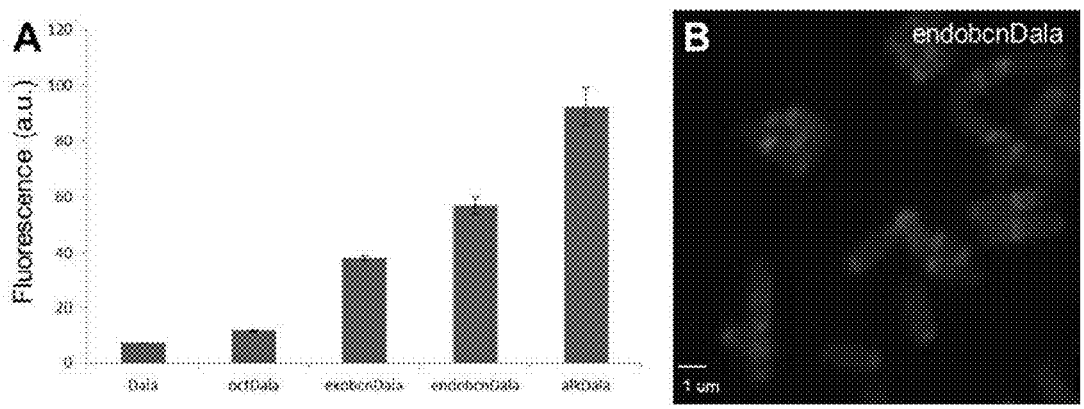
FIG. 21A-B
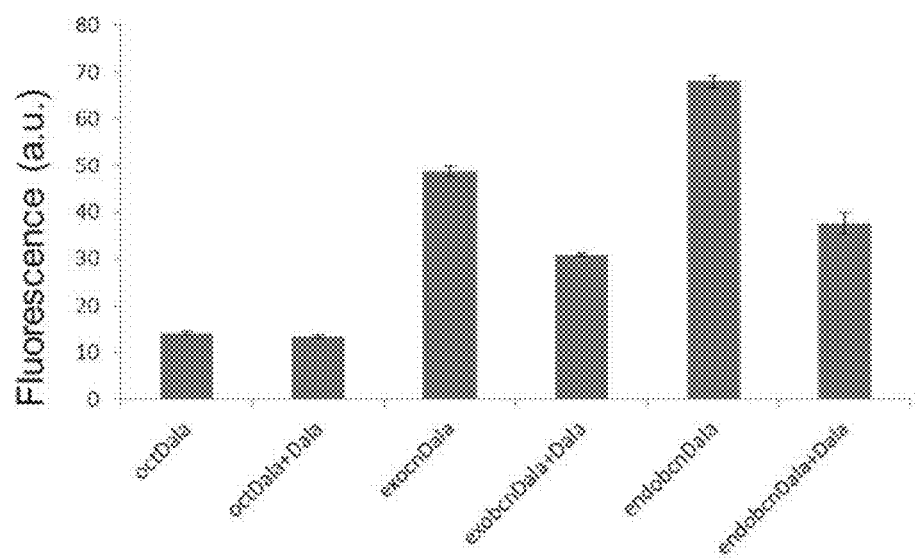
FIG. 22

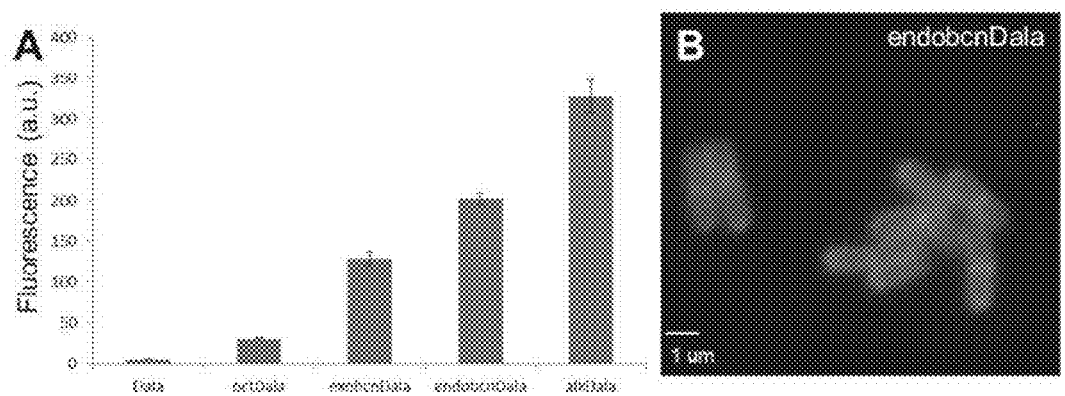
FIG. 23A-B
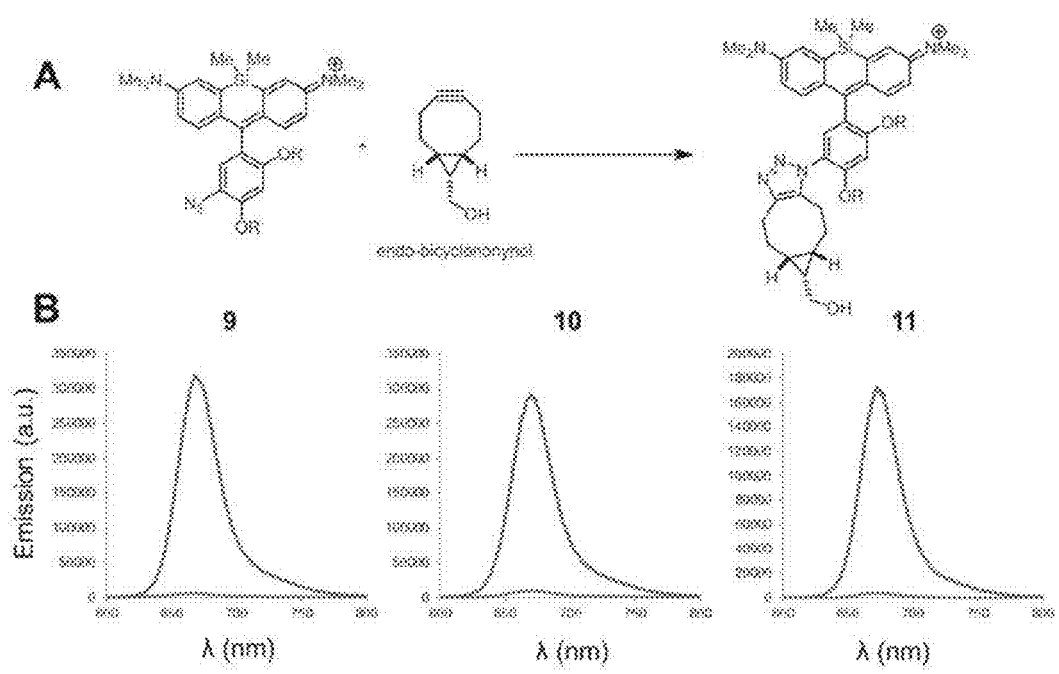
FIG. 24A-B

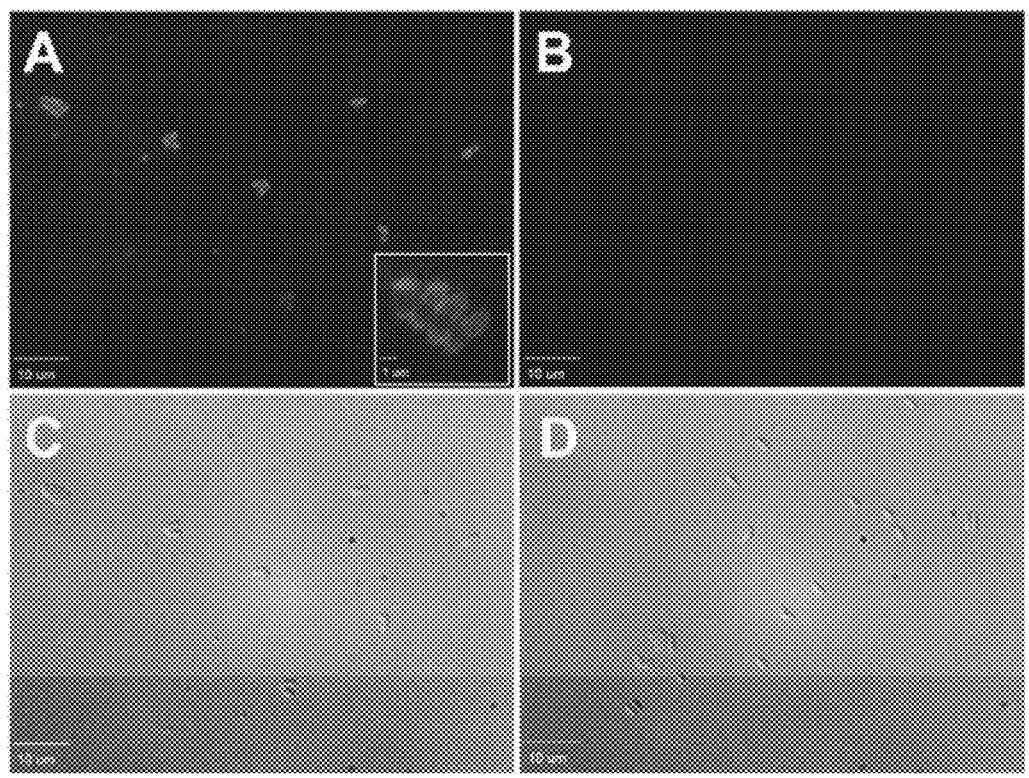
FIG. 25A-D

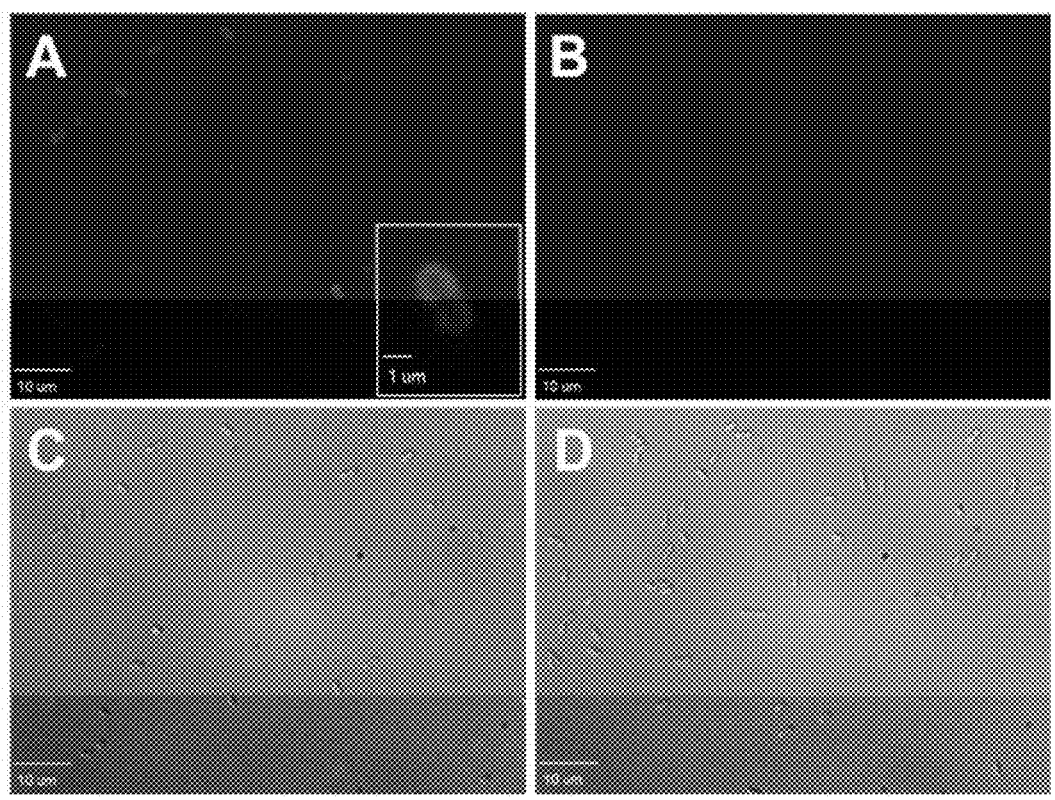
FIG. 26A-D

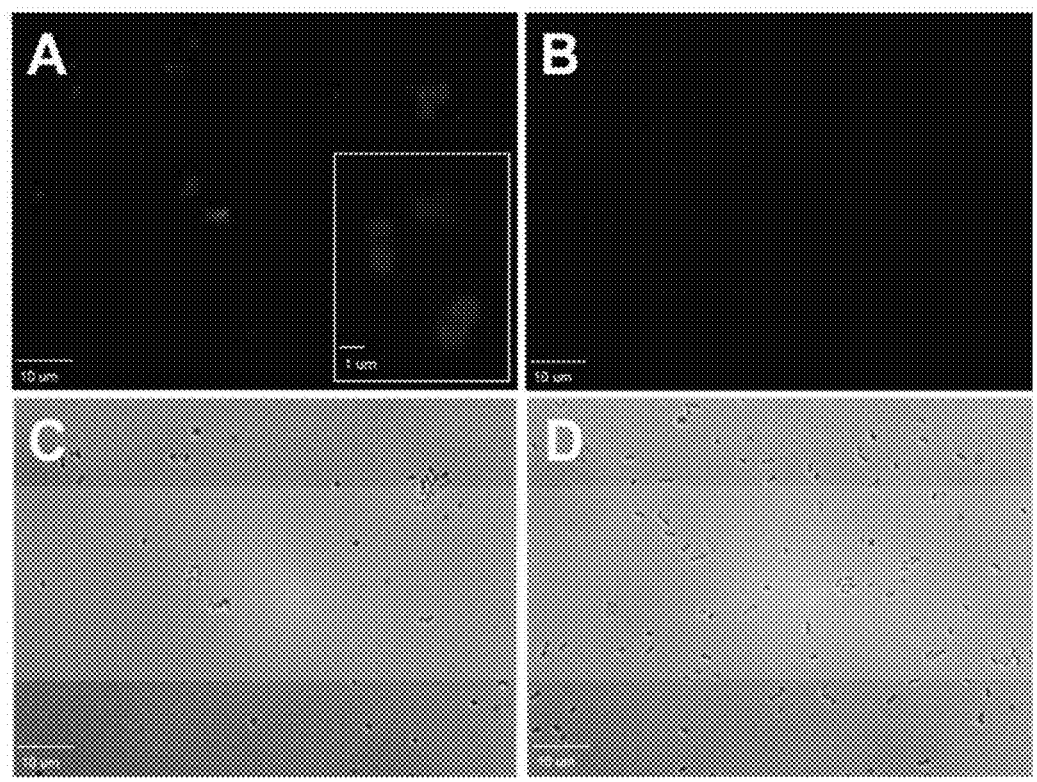
FIG. 27A-D

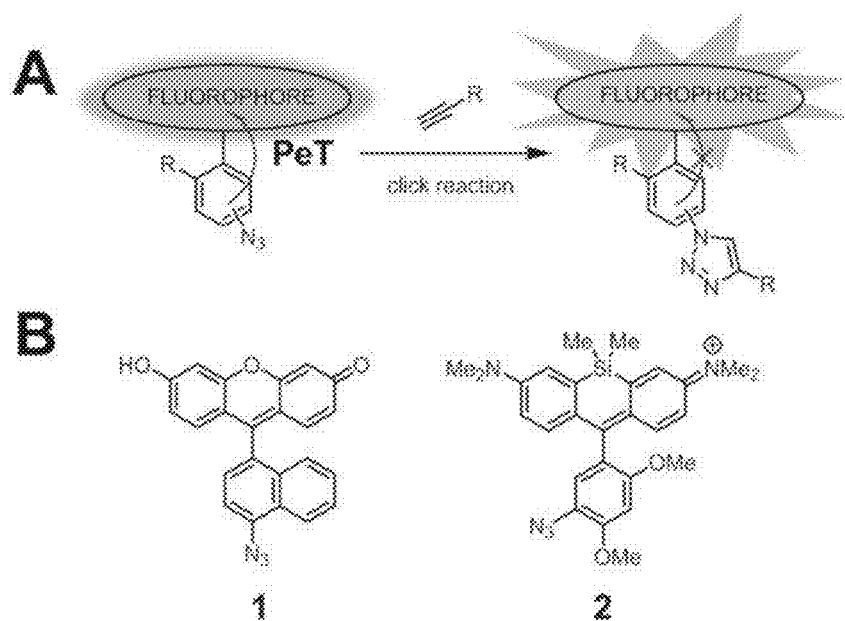
FIG. 30A-B

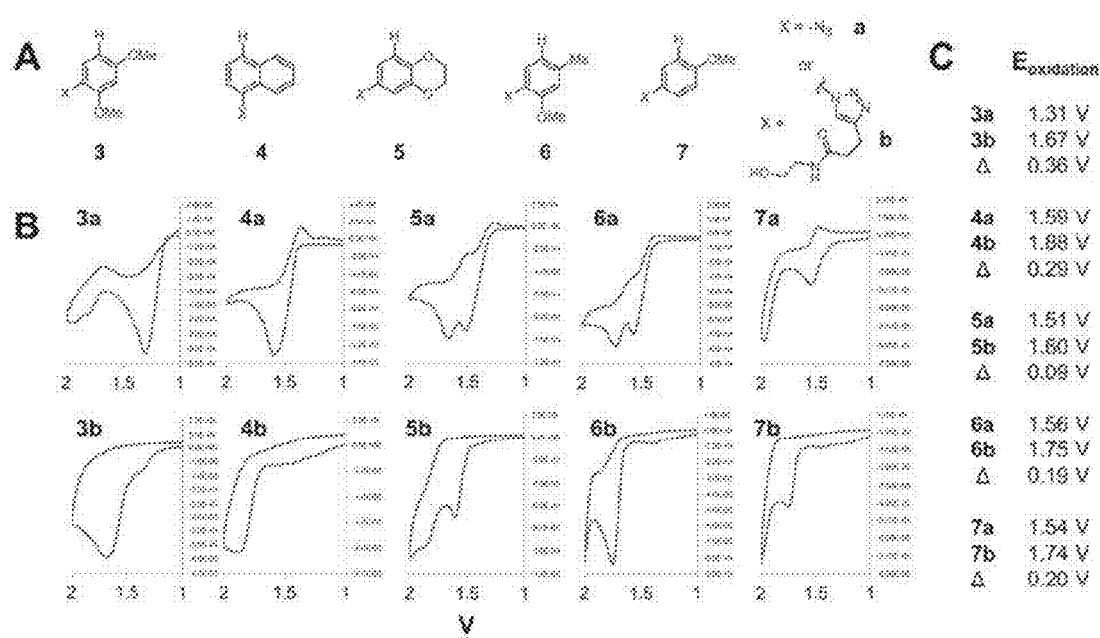
FIG. 31A-B

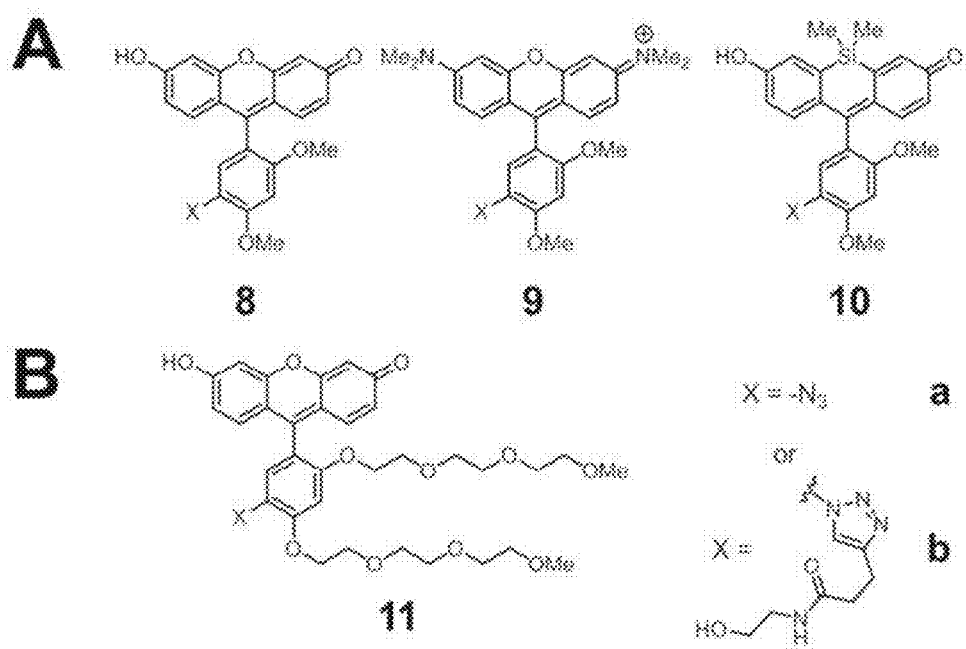
FIG. 32A-B

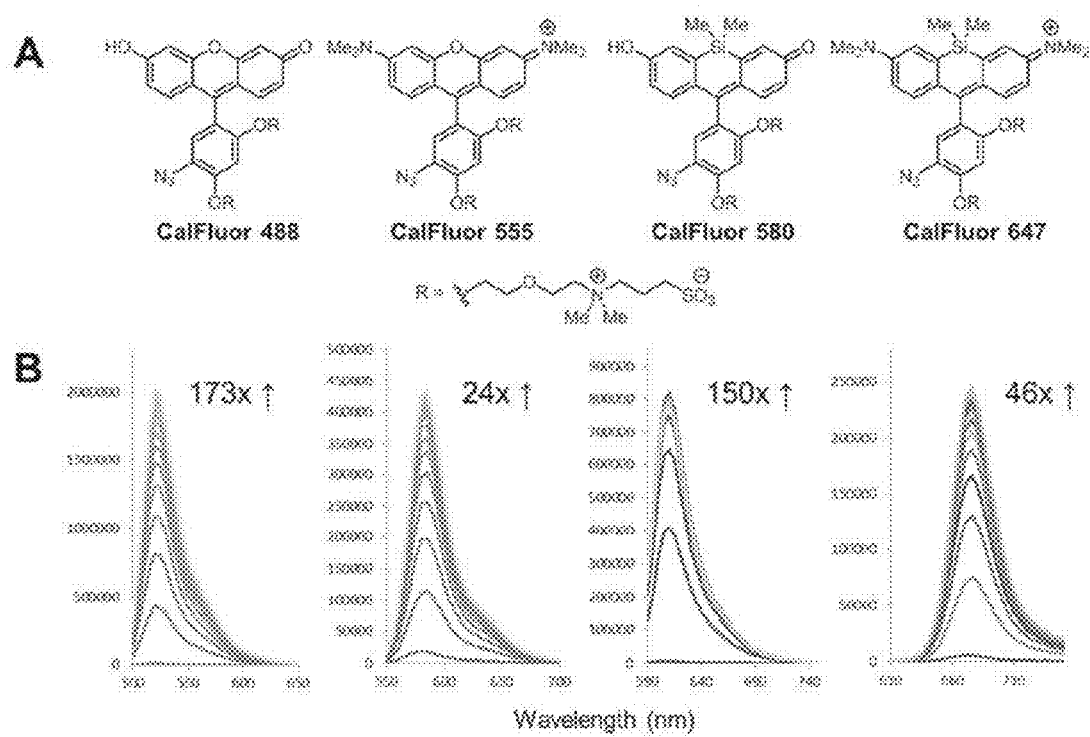
FIG. 33A-B

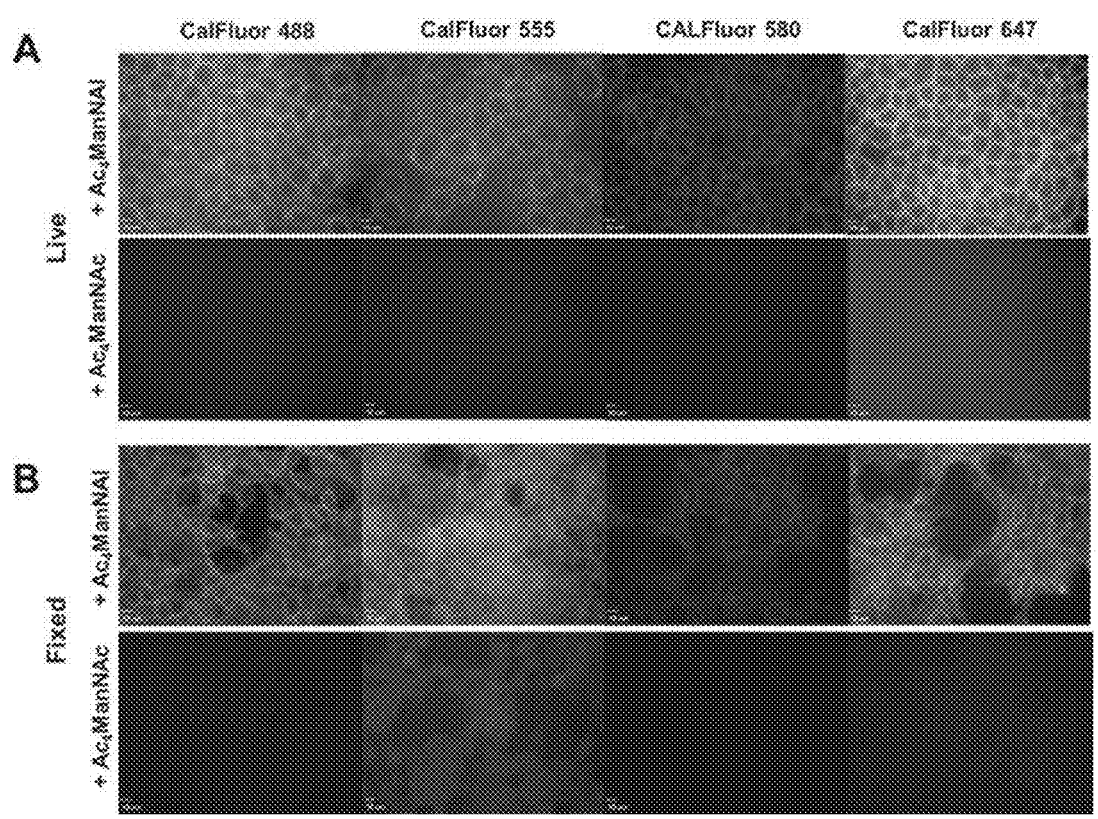
FIG. 34A-B

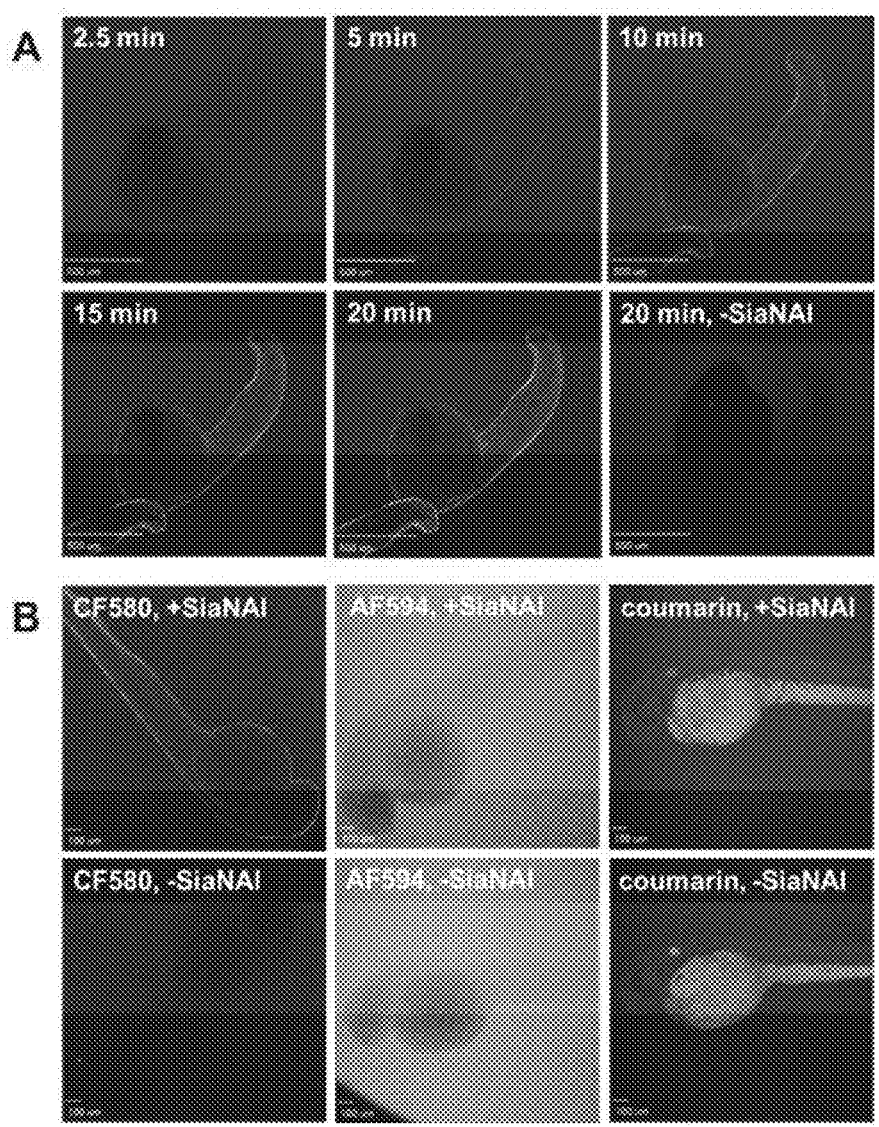
FIG. 35A-B

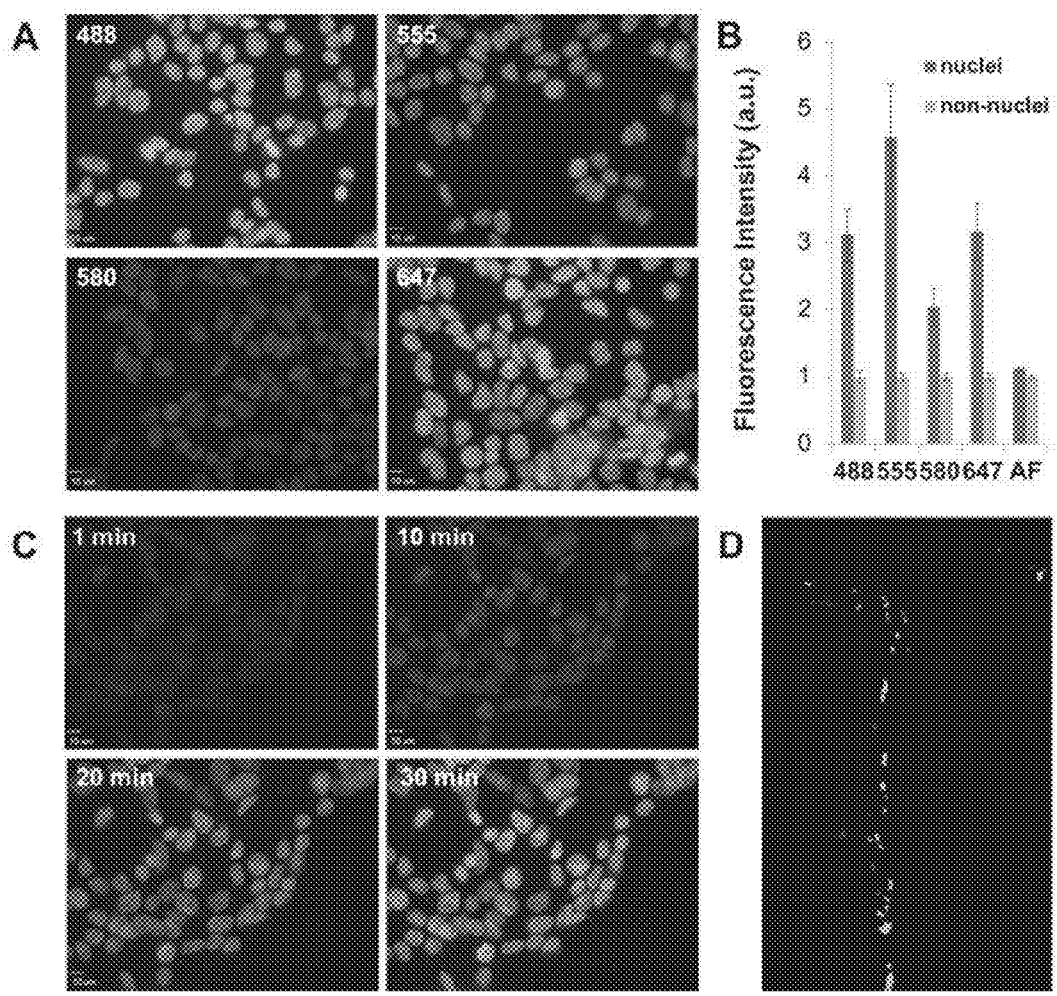
FIG. 36A-D

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 1

Tyr Pro Tyr Asp Val Pro Asp Tyr Ala
1               5

<210> SEQ ID NO 2
<211> LENGTH: 8
<212> TYPE: PRT
<213> ORGANISM: Artificial sequence
<220> FEATURE:
```

```
<223> OTHER INFORMATION: Synthetic polypeptide

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 3

Asp Tyr Lys Asp Asp Asp Asp Lys Cys
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 4

Glu Gln Lys Leu Ile Ser Glu Glu Asp Leu
1               5                   10

<210> SEQ ID NO 5
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 5

His His His His His
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 6

His His His His His His
1               5

<210> SEQ ID NO 7
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 7

Glu Gln Lys Leu Ile Ser Glu Glu Asp Leu
1               5                   10

<210> SEQ ID NO 8
<211> LENGTH: 8
<212> TYPE: PRT
<213> ORGANISM: Artificial sequence
<220> FEATURE:
<223> OTHER INFORMATION: Synthetic polypeptide
```

```
<400> SEQUENCE: 8

Trp Ser His Pro Gln Phe Glu Lys
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 9

Tyr Pro Tyr Asp Val Pro Asp Tyr Ala
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 10

Arg Tyr Ile Arg Ser
1               5

<210> SEQ ID NO 11
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 11

Phe His His Thr
1

<210> SEQ ID NO 12
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 12

Trp Glu Ala Ala Ala Arg Glu Ala Cys Cys Arg Glu Cys Cys Ala Arg
1               5                   10                  15
Ala
```

ALKYNE-ACTIVATED FLUOROGENIC AZIDE COMPOUNDS AND METHODS OF USE THEREOF

CROSS-REFERENCE

This application claims the benefit of U.S. Provisional Patent Application No. 61/970,200, filed Mar. 25, 2014, which application is incorporated herein by reference in its entirety.

STATEMENT REGARDING FEDERALLY SPONSORED RESEARCH

This invention was made with government support under Grant Nos. GM058867 and AI051622 awarded by The National Institutes of Health. The government has certain rights in the invention.

INTRODUCTION

Significant progress has been made in the discovery of fluorogenic probes activated by various bioorthogonal chemistries, including the Staudinger ligation as well as azide-alkyne, tetrazine-alkene, tetrazine-alkyne, and photoactivated tetrazole-alkene cycloadditions. However, the dyes employed have emission maxima below 600 nm. The identification of activatable near-infrared (NIR) fluorogenic probes with emission maxima greater than 600 nm has proven much more challenging.

There is a need in the art for methods of labeling biomolecules in vitro or in vivo.

SUMMARY

The present disclosure provides fluorogenic azide compounds. Also provided are methods of using the subject compounds for labelling a target biomolecule that includes an alkyne. In some embodiments, the method includes contacting the biomolecule with a fluorogenic azide compound, wherein the contacting results in covalent linkage of the compound with the alkyne moiety of the target biomolecule.

BRIEF DESCRIPTION OF THE DRAWINGS

FIG. 4A-4C show a schematic and graphs of fluorescence enhancement of 9 during copper-catalyzed click reaction in situ, according to embodiments of the present disclosure. FIG. 4A shows the reaction between fluorogenic Si-rhodamine 9 and alkyne A. FIG. 4B shows emission spectra acquired during the reaction. Scans were performed every 30 seconds, with the first scan acquired immediately before addition of alkyne A. $\lambda_{ex}$=600 nm. FIG. 4C shows a plot of emission at 670 nm vs. reaction time.

FIG. 5 shows structures of bis-oligoethylene glycol-substituted azido Si-rhodamine probe 10 and bis-sulfated probe 11, according to embodiments of the present disclosure.

FIG. 15 shows a fluorescence image of Ac$_4$ManNAl-treated HEK 293T cells labeled with 10, according to embodiments of the present disclosure. Labeling was performed for 15 min and quenched with BCS following the above procedure. Scale bar=50 µm.

FIG. 16A-D show images of mitochondrial staining by 10 in HEK 293T cells, according to embodiments of the present disclosure. (A) Brightfield image (B) Cy5 channel showing fluorescence from 10 (C) FITC channel showing mitochondrial staining by MitoTracker Green FM. (D) Overlay of Cy5 and FITC channels. Scale bar=10 µm

FIG. 19A-19B show labeling of *M. smegmatis* with azido-$PEG_3$-carboxyrhodamine 110, according to embodiments of the present disclosure. (A) Flow cytometry data of labeling with various D-amino acids. (B) A representative image showing cell surface localization of fluorescence signal for cells treated with endobcnDala. Scale bar=1 µm.

FIG. 20A-20B show labeling of *C. glutamicum* with azido-$PEG_3$-carboxyrhodamine 110, according to embodiments of the present disclosure. (A) Flow cytometry data of labeling with various D-amino acids. (B) A representative image showing cell surface localization of fluorescence signal for cells treated with endobcnDala. Scale bar=1 µm.

FIG. 21A-21B show labeling of wild-type *L. monocytogenes* with azido-$PEG_3$-carboxyrhodamine 110, according to embodiments of the present disclosure. (A) Flow cytometry data of labeling with various D-amino acids. (B) A representative image showing cell surface localization of fluorescence signal for cells treated with endobcnDala. Scale bar=1 µm.

FIG. 22 shows a graph of a competition experiment using wild-type *L. monocytogenes*, according to embodiments of the present disclosure. The bacteria were incubated with 5 mM cyclooctyne amino acid, in the presence of either 0 or 20 mM D-alanine, and labeled following the general procedure.

FIG. 23A-23B show labeling of *L. monocytogenes* pbp5::tn with azido-$PEG_3$-carboxyrhodamine 110, according to embodiments of the present disclosure. (A) Flow cytometry data of labeling with various D-amino acids. (B) A representative image showing cell surface localization of fluorescence signal for cells treated with endobcnDala. Note the increased sidewall labeling versus wild-type *L. monocytogenes*. Scale bar=1 µm.

FIG. 24A-24B show a scheme and graphs of fluorescence enhancement upon reaction with endo-bicyclononynol, according to embodiments of the present disclosure. (A) Reaction of azido Si-rhodamines 9 to 11 with endobicyclononynol to form a triazole. (B) Fluorescence spectra of 2 µM 9 to 11 incubated with either 2 eq. endo-bicyclononynol in DMSO (red) or only DMSO (blue) for 18 h. Excitation at 600 nm.

FIG. 25A-25D show images of no-wash peptidoglycan labeling of *Corynebacterium glutamicum* with reduced amino acid loading, according to embodiments of the present disclosure. Bacteria were incubated with 500 µM endobcn-Dala for one doubling time and imaged in the presence of 5 µM of azido Si-rhodamine 11 as described above. (A), (C) Fluorescence and brightfield images of bacteria incubated with endobcnDala. (B), (D) Fluorescence and brightfield images of bacteria incubated with Dala. Scale bar=10 Inset in (A) shows cells enlarged to highlight cell surface labeling. Scale bar=1 µm.

FIG. 26A-26D shows images of no-wash peptidoglycan labeling of the Gram-negative *Escherichia coli*, according to embodiments of the present disclosure. *E. coli* incubated with 5 mM endobcnDala or Dala for 2 h from a starting OD of 0.05 and imaged in the presence of 20 µM of azido Si-rhodamine 11 as described above. Only a fraction of the bacteria incubated with endobcnDala were fluorescently labeled under these conditions. (A), (C) Fluorescence and brightfield images of *E. coli* incubated with 5 mM endobcnDala. (B), (D) Fluorescence and brightfield images of *E. coli* incubated with 5 mM Dala. Scale bar=10 µm. Inset in (A) shows cells enlarged to highlight cell surface labeling. Scale bar=1 µm.

FIG. 27A-27D show images of labeling *Escherichia coli* with azido-carboxyrhodamine 110, according to embodiments of the present disclosure. *E. coli* were incubated with 5 mM endobcnDala or Dala for 2 h from a starting OD of 0.05, washed, and labeled with using 20 µM of azido-carboxyrhodamine 110 (Lumiprobe, note the lack of a PEG spacer) for 1 h. The cells were then washed, fixed, and imaged as described above for labeling with azido-$PEG_3$-carboxyrhodamine 110. (A), (C) Fluorescence and brightfield images of *E. coli* incubated with 5 mM endobcnDala. (B), (D) Fluorescence and brightfield images of *E. coli* incubated with 5 mM Dala. Scale bar=10 µm. Inset in (A) shows cells enlarged to highlight cell surface labeling. Scale bar=1 µm.

FIG. 30A-B show PeT-based fluorogenic azide probes activated by click chemistry. (A) General strategy. (B) Structures of fluorogenic azide probes of interest.

FIG. 31A-B show a cyclic voltammetry analysis of substituted aryl systems of interest. (A) Aryl azides (3a-7a) and triazoles (3b-7b) synthesized and studied by cyclic voltammetry. (B) Cyclic voltammetry plots of compounds 3-7. (C) Oxidation potentials of compounds 3-7.

FIG. 32A-B depict structures of fluorophores of interest. (A) Dimethoxy-substituted fluorophores 8 to 10. (B) Oligoethylene-glycol functionalized fluorescein derivative 11.

FIG. 33A-B illustrate structures of CalFluors of interest and their fluorescence enhancements. (A) Structures of CalFluors 488, 555, 580, and 647. (B) Fluorescence enhancements of CalFluors during copper-catalyzed click reactions.

FIG. 34A-B illustrates no-wash labeling of cell-surface glycoproteins on HEK 293T cells. Cells were grown for 3 days, then subjected to click labeling with CalFluor probes. (A) Labeling glycoproteins on live cell surfaces. (B) Labeling glycoproteins on fixed cells.

FIG. 35A-B illustrate visualization of sialic acids in developing zebrafish with CalFluors. Zebrafish were injected with 50 pmol SiaNAl at the one to four-cell stage and allowed to develop over time. (A) Real-time labeling of sialic acids. After 24 hpf, zebrafish were incubated in a solution containing 1 µM CalFluor 580 and copper catalyst. Alkyne-dependent labeling was observable after 5 minutes, and appeared to saturate at 20 minutes. Scale bar=500 (B) Comparing no-wash labeling performance by azide probes. After 36 hpf, the embryos were transferred to a solution containing the fluorophore (1 µM for CalFluor 580 and AlexaFluor 594 alkyl azide, or 5 µM for 3-azido-7-hydroxycoumarin) and copper catalyst and imaged without washing after 20 minutes. Only zebrafish labeled with CalFluor 580 show alkyne-dependent fluorescence signal. Scale bar=100 μm.

FIG. 36A-D illustrate visualization of 5-ethynyl-2'-deoxyuridine (EdU)-labeled DNA using fluorogenic azide probes. (A) No-wash labeling of EdU-labeled HEK 293T cells. Cells were treated with EdU for 16 h, fixed and permeabilized, then treated with 10 μM CalFluor probe, 1 mM $CuSO_4$, 100 μM TBTA ligand, 2 mM sodium ascorbate, and 0.1 mg/mL BSA and imaged without further wash steps after 1 hour. (B) Quantification of normalized signal over background for the four panels in (A), and comparison to labeling under identical conditions using the non-fluorogenic AlexaFluor 647 alkyl azide (AF). (C) Two-color labeling using Hoescht 33342 and CalFluor 555. After staining with Hoescht, the cells were incubated with a solution of 1 μM CalFluor probe and copper catalyst and imaged in real-time. (D) Visualization of EdU-labeled newly proliferating cells in mouse brain slices with CalFluor 647.

DEFINITIONS

Figure 1:
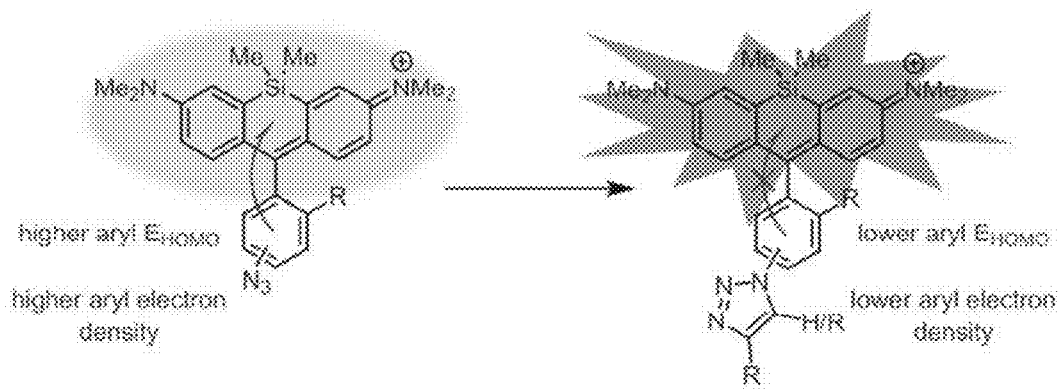
FIG. 1 shows a schematic of a photoinduced electron transfer (PeT)-based fluorogenic azido Si-rhodamine, according to embodiments of the present disclosure.

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3$)($CH_3CH_2$)CH—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocloooxy, thiol, thioalkoxy, substituted thioalkoxy, aryl, aryloxy, heteroaryl, heteroaryloxy, heterocyclyl, heterocloooxy, hydroxylamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH$($CH_3$)—), (—C($CH_3$)2CH2CH2-), (—C($CH_3$)$_2CH_2$C(O)—), (—C($CH_3$)$_2CH_2$C(O)NH—), (—CH($CH_3$)$CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocloooxy, thiol, thioalkoxy, substituted thioalkoxy, aryl, aryloxy, heteroaryl, heteroaryloxy, heterocyclyl, heterocloooxy, hydroxylamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxylamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH3C(O)—

"Acylamino" refers to the groups —NR$_{20}$C(O)alkyl, —NR$_{20}$C(O)substituted alkyl, NR$_{20}$C(O)cycloalkyl, —NR$_{20}$C(O)substituted cycloalkyl, —NR$_{20}$C(O)cycloalkenyl, —NR$_{20}$C(O)substituted cycloalkenyl, —NR$_{20}$C(O)alkenyl, —NR$_{20}$C(O)substituted alkenyl, —NR$_{20}$C(O)alkynyl, —NR$_{20}$C(O)substituted alkynyl, —NR$_{20}$C(O)aryl, —NR$_{20}$C(O)substituted aryl, —NR$_{20}$C(O)heteroaryl, —NR$_{20}$C(O)substituted heteroaryl, —NR$_{20}$C(O)heterocyclic, and —NR$_{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxyl, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO2-alkyl, —SO2-substituted alkyl, —SO2-aryl, —SO2-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O— cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclohexyl, cyclooctyl and the like. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxylamino, alkoxyamino, nitro, —SO-alkyl, —SO-substituted alkyl, —SO-aryl, —SO-heteroaryl, —SO2-alkyl, —SO2-substituted alkyl, —SO2-aryl and —SO2-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxylamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxyl, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxylamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxylamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cycloalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example of 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the terms "polyethylene oxide", "PEO", "polyethylene glycol" and "PEG" are used interchangeably and refer to a polymeric group including a chain described by the formula —$(CH_2$—$CH_2$—O—$)_n$— or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15. It is understood that the PEG polymeric group may be of any convenient length and may include a variety of terminal groups and/or further substituent groups, including but not limited to, alkyl, aryl, hydroxyl, amino, acyl, acyloxy, and amido terminal and/or substituent groups. PEG groups that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165; and by Zhu et al in "Water-Soluble Conjugated Polymers for Imaging, Diagnosis, and Therapy", Chem. Rev., 2012, 112 (8), pp 4687-4735.

The term "water solubilizing group" (WSG) refers to a group that is well solvated in aqueous environments e.g., under physiological conditions, and that imparts improved water solubility to the molecules to which it is attached. In some embodiments, a WSG increases the solubility of the compound in a predominantly aqueous solution, as compared to a compound which lacks the WSG. The water soluble groups may be any convenient hydrophilic group that is well solvated in aqueous environments. In some cases, the hydrophilic water soluble group is charged, e.g., positively or negatively charged. In certain cases, the hydrophilic water soluble group is a neutral hydrophilic group. In some embodiments, the WSG is a hydrophilic polymer, e.g., a polyethylene glycol, a cellulose, a chitosan, or a derivative thereof. Water soluble groups of interest include, but are not limited to, carboxylate, phosphonate, phosphate, sulfonate, sulfate, sulfinate, sulfonium, ester, polyethylene glycols (PEG) and modified PEGs, hydroxyl, amine, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —$SO_3M'$, —$PO_3M'$, —$NR_3^+$, Y', $(CH_2CH_2O)_pR$ and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —$(CH_2CH_2O)_{yy}CH_2CH_2XR^{yy}$, —$(CH_2CH_2O)_{yy}CH_2CH_2X$—, —$X(CH_2CH_2O)_{yy}CH_2CH_2$—, glycol, and polyethylene glycol, wherein yy is selected from 1 to 1000, X is selected from O, S, and $NR^{zz}$, and $R^{zz}$ and $R^{yy}$ are independently selected from H and $C_{1-3}$ alkyl.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "physiological conditions" is meant to encompass those conditions compatible with living cells, e.g., predominantly aqueous conditions of a temperature, pH, salinity, etc. that are compatible with living cells.

As used herein, the term "cell" in the context of the in vivo applications of the invention is meant to encompass eukaryotic and prokaryotic cells of any genus or species. Eukaryotic cells include, but are not limited to, mammalian cells, fungal cells, yeast cells, plant cells, and single-celled parasites. "Cell" is also meant to encompass both normal cells and diseased cells, e.g., cancerous cells. In many embodiments, the cells are living cells.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a fluorogenic azide compound" includes a plurality of such compounds and reference to "the cellular component" includes reference to one or more cellular components and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides fluorogenic azide compounds, and methods of use of same for labelling a target biomolecule.

Azido-Functionalized Fluorogenic Compounds

The present disclosure provides azido-functionalized fluorogenic compounds, and compositions including the compounds. The fluorogenic azide compounds may include a xanthene scaffold directly linked to an azido switch group. An azido switch group refers to an aryl or heteroaryl group that includes an azido substitutent and is electronically connected (e.g., capable of photoinduced electron transfer) with the xanthene scaffold such that conversion of the azide to a triazole (e.g., via Click conjugation) unquenches a fluorescence of the xanthene. Any convenient xanthene scaffold may be adapted for use in the subject compounds. In some instances, an azido-functionalized fluorogenic compound of the present disclosure includes a compound of any one of Formulas I-V, as set out below.

Aspects of the present disclosure include a compound of formula (I):

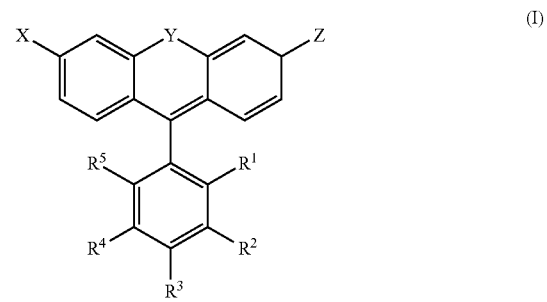

wherein
X is selected from hydroxyl, amino and substituted amino;
Y is O or an alkylsilane;
Z is selected from oxo, imine and substituted imine;
$R^1$, $R^2$, $R^3$, $R^4$ and $R^5$ are each independently selected from hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl;
optionally, one of $R^1$, $R^2$, $R^3$, $R^4$ or $R^5$ together with its adjacent R-group form a cycloalkyl, substituted cycloalkyl, heterocycloalkyl, substituted heterocycloalkyl, aryl, substituted aryl, heteroaryl or substituted heteroaryl; and
one of $R^1$, $R^2$, $R^3$, $R^4$ or $R^5$ is azido and one of $R^1$, $R^2$, $R^3$, $R^4$ or $R^5$ is optionally a molecule of interest.

In certain embodiments, X is selected from hydroxyl, amino and substituted amino. In certain embodiments, X is hydroxyl. In certain embodiments, X is amino or substituted amino. In some instances, X is amino. In some instances, X is amino substituted with one or two alkyl or substituted alkyl groups, such as $C_1$-$C_6$ alkyl or $C_1$-$C_3$ alkyl, or $C_1$-$C_6$ substituted alkyl or $C_1$-$C_3$ substituted alkyl. For example, X may be amino substituted with one or two methyl groups. In some instances, X is dimethylamino.

In certain embodiments, Y is O or an alkylsilane. In certain embodiments, Y is O. In certain embodiments, Y is an alkylsilane, such as a silane substituted with one or two alkyl or substituted alkyl groups, such as $C_1$-$C_6$ alkyl or $C_1$-$C_3$ alkyl, or $C_1$-$C_6$ substituted alkyl or $C_1$-$C_3$ substituted alkyl. For example, Y may be a silane substituted with one or two methyl group. In some instances, Y is silane substituted with two methyl groups.

In certain embodiments, Z is selected from oxo, imine and substituted imine. In certain embodiments, Z is oxo. In certain embodiments, Z is imine or substituted imine. In some instances, Z is an imine. In some instances, Z is a substituted imine, such as an imine substituted with one or two alkyl or substituted alkyl groups, such as $C_1$-$C_6$ alkyl or $C_1$-$C_3$ alkyl, or $C_1$-$C_6$ substituted alkyl or $C_1$-$C_3$ substituted alkyl. For example, Z may be an imine substituted with a methyl group (e.g., =NCH$_3$). In some cases, Z is an imine substituted with two methyl groups, and as such may have a charge, such as a positive charge (e.g., an aminium group; =N(CH$_3$)$_2$$^+$).

In certain embodiments, $R^1$, $R^2$, $R^3$, $R^4$ and $R^5$ are each independently selected from hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl.

In certain embodiments, $R^1$, $R^2$, $R^3$, $R^4$ and $R^5$ are each independently selected from hydrogen, alkyl, substituted alkyl, alkoxy, substituted alkoxy, azido, amino, substituted amino, cycloalkyl, substituted cycloalkyl, heterocycloalkyl, substituted heterocycloalkyl, aryl, substituted aryl, heteroaryl, and substituted heteroaryl.

In certain embodiments, $R^1$, $R^2$, $R^3$, $R^4$ and $R^5$ are each independently selected from hydrogen, alkyl, substituted alkyl, alkoxy, substituted alkoxy, azido, heterocycloalkyl, and substituted heterocycloalkyl.

In certain embodiments, $R^1$ is selected from hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl. In certain embodiments, $R^1$ is hydrogen. In certain embodiments, $R^1$ is alkyl or substituted alkyl. For example, $R^1$ may be $C_1$-$C_6$ alkyl, such as $C_1$-$C_3$ alkyl. In some instances, $R^1$ is methyl. In certain embodiments, $R^1$ is alkoxy or substituted alkoxy. For example, $R^1$ may be $C_1$-$C_6$ alkoxy, such as $C_1$-$C_3$ alkoxy. In some instances, $R^1$ is methoxy. In some instances, $R^1$ is substituted alkoxy, such as $C_1$-$C_6$ alkoxy, substituted with one or more groups, such as, but not limited to alkyl, substituted alkyl, alkoxy, substituted alkoxy, and the like. For example, $R^1$ may be substituted alkoxy, such as $C_1$-$C_6$ alkoxy, substituted with an alkoxy or substituted alkoxy. For instance, $R^1$ may include a polyethylene glycol group, such as —(OCH$_2$CH$_2$)$_n$—$R^{10}$, where n is an integer from 1 to 10 and $R^{10}$ is selected from alkyl, substituted alkyl, hydroxyl, alkoxy, substituted alkoxy, acyl, acyloxy, carboxyl, carboxyl ester and sulfate. In some instances, n is 1. In some instances, n is 2. In some instances, n is 3. In some instances, n is 4. In some instances, n is 5. In some instances, n is 6. For example, $R^1$ may be —(OCH$_2$CH$_2$)$_n$—$R^{10}$, where n is 3 and $R^{10}$ is methoxy. In some instances, $R^{10}$ is alkoxy, such as $C_1$-$C_6$ alkoxy, e.g., methoxy. In certain embodiments, $R^{10}$ is hydroxyl. In certain embodiments, $R^{10}$ is acyl or acyloxy. In certain embodiments, $R^{10}$ is carboxyl or carboxyl ester. In certain embodiments, $R^{10}$ is sulfate. In certain embodiments, $R^1$ is azido. In certain embodiments, $R^1$ is amino or substituted amino. In certain embodiments, $R^1$ is nitro. In certain embodiments, $R^1$ is cyano. In certain embodiments, $R^1$ is acyl, carboxyl, or carboxylester. In certain embodiments, $R^1$ is cycloalkyl or substituted cycloalkyl. In certain embodiments, $R^1$ is heterocycloalkyl or substituted heterocycloalkyl. In certain embodiments, $R^1$ is aryl or substituted aryl. In certain embodiments, $R^1$ is heteroaryl or substituted heteroaryl.

In certain embodiments, $R^2$ is selected from hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl. In certain embodiments, $R^2$ is hydrogen. In certain embodiments, $R^2$ is alkyl or substituted alkyl. For example, $R^2$ may be $C_1$-$C_6$ alkyl, such as $C_1$-$C_3$ alkyl. In some instances, $R^2$ is methyl. In certain embodiments, $R^2$ is alkoxy or substituted alkoxy. For example, $R^2$ may be $C_1$-$C_6$ alkoxy, such as $C_1$-$C_3$ alkoxy. In some instances, $R^2$ is methoxy. In some instances, $R^2$ is substituted alkoxy, such as $C_1$-$C_6$ alkoxy, substituted with one or more groups, such as, but not limited to alkyl, substituted alkyl, alkoxy, substituted alkoxy, and the like. For example, $R^2$ may be substituted alkoxy, such as $C_1$-$C_6$ alkoxy, substituted with an alkoxy or substituted alkoxy. For instance, $R^2$ may include a polyethylene glycol group, such as —(OCH$_2$CH$_2$)$_n$—$R^{10}$, where n is an integer from 1 to 10 and $R^{10}$ is selected from alkyl, substituted alkyl, hydroxyl, alkoxy, substituted alkoxy, acyl, acyloxy, carboxyl, carboxyl ester and sulfate. In some instances, n is 1. In some instances, n is 2. In some instances, n is 3. In some instances, n is 4. In some instances, n is 5. In some instances, n is 6. For example, $R^2$ may be —(OCH$_2$CH$_2$)$_n$—$R^{10}$, where n is 3 and $R^{10}$ is methoxy. In some instances, $R^{10}$ is alkoxy, such as $C_1$-$C_6$ alkoxy, e.g., methoxy. In certain embodiments, $R^{10}$ is hydroxyl. In certain embodiments, $R^{10}$ is acyl or acyloxy. In certain embodiments, $R^{10}$ is carboxyl or carboxyl ester. In certain embodiments, $R^{10}$ is sulfate. In certain embodiments, $R^2$ is azido. In certain embodiments, $R^2$ is amino or substituted amino. In certain embodiments, $R^2$ is nitro. In certain embodiments, $R^2$ is cyano. In certain embodiments, $R^2$ is acyl, carboxyl, or carboxylester. In certain embodiments, $R^2$ is cycloalkyl or substituted cycloalkyl. In certain embodiments, $R^2$ is heterocycloalkyl or substituted heterocycloalkyl. In certain embodiments, $R^2$ is aryl or substituted aryl. In certain embodiments, $R^2$ is heteroaryl or substituted heteroaryl.

In certain embodiments, $R^3$ is selected from hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl. In certain embodiments, $R^3$ is hydrogen. In certain embodiments, $R^3$ is alkyl or substituted alkyl. For example, $R^3$ may be $C_1$-$C_6$ alkyl, such as $C_1$-$C_3$ alkyl. In some instances, $R^3$ is methyl. In certain embodiments, $R^3$ is alkoxy or substituted alkoxy. For example, $R^3$ may be $C_1$-$C_6$ alkoxy, such as $C_1$-$C_3$ alkoxy. In some instances, $R^3$ is methoxy. In some instances, $R^3$ is substituted alkoxy, such as $C_1$-$C_6$ alkoxy, substituted with one or more groups, such as, but not limited to alkyl, substituted alkyl, alkoxy, substituted alkoxy, and the like. For example, $R^3$ may be substituted alkoxy, such as $C_1$-$C_6$ alkoxy, substituted with an alkoxy or substituted alkoxy. For instance, $R^3$ may include a polyethylene glycol group, such as —$(OCH_2CH_2)_n$—$R^{10}$, where n is an integer from 1 to 10 and $R^{10}$ is selected from alkyl, substituted alkyl, hydroxyl, alkoxy, substituted alkoxy, acyl, acyloxy, carboxyl, carboxyl ester and sulfate. In some instances, n is 1. In some instances, n is 2. In some instances, n is 3. In some instances, n is 4. In some instances, n is 5. In some instances, n is 6. For example, $R^3$ may be —$(OCH_2CH_2)_n$—$R^{10}$, where n is 3 and $R^{10}$ is methoxy. In some instances, $R^{10}$ is alkoxy, such as $C_1$-$C_6$ alkoxy, e.g., methoxy. In certain embodiments, $R^{10}$ is hydroxyl. In certain embodiments, $R^{10}$ is acyl or acyloxy. In certain embodiments, $R^{10}$ is carboxyl or carboxyl ester. In certain embodiments, $R^{10}$ is sulfate. In certain embodiments, $R^3$ is azido. In certain embodiments, $R^3$ is amino or substituted amino. In certain embodiments, $R^3$ is nitro. In certain embodiments, $R^3$ is cyano. In certain embodiments, $R^3$ is acyl, carboxyl, or carboxylester. In certain embodiments, $R^3$ is cycloalkyl or substituted cycloalkyl. In certain embodiments, $R^3$ is heterocycloalkyl or substituted heterocycloalkyl. In certain embodiments, $R^3$ is aryl or substituted aryl. In certain embodiments, $R^3$ is heteroaryl or substituted heteroaryl.

In certain embodiments, $R^4$ is selected from hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl. In certain embodiments, $R^4$ is hydrogen. In certain embodiments, $R^4$ is alkyl or substituted alkyl. For example, $R^4$ may be $C_1$-$C_6$ alkyl, such as $C_1$-$C_3$ alkyl. In some instances, $R^4$ is methyl. In certain embodiments, $R^4$ is alkoxy or substituted alkoxy. For example, $R^4$ may be $C_1$-$C_6$ alkoxy, such as $C_1$-$C_3$ alkoxy. In some instances, $R^4$ is methoxy. In some instances, $R^4$ is substituted alkoxy, such as $C_1$-$C_6$ alkoxy, substituted with one or more groups, such as, but not limited to alkyl, substituted alkyl, alkoxy, substituted alkoxy, and the like. For example, $R^4$ may be substituted alkoxy, such as $C_1$-$C_6$ alkoxy, substituted with an alkoxy or substituted alkoxy. For instance, $R^4$ may include a polyethylene glycol group, such as —$(OCH_2CH_2)_n$—$R^{10}$, where n is an integer from 1 to 10 and $R^{10}$ is selected from alkyl, substituted alkyl, hydroxyl, alkoxy, substituted alkoxy, acyl, acyloxy, carboxyl, carboxyl ester and sulfate. In some instances, n is 1. In some instances, n is 2. In some instances, n is 3. In some instances, n is 4. In some instances, n is 5. In some instances, n is 6. For example, $R^4$ may be —$(OCH_2CH_2)_n$—$R^{10}$, where n is 3 and $R^{10}$ is methoxy. In some instances, $R^{10}$ is alkoxy, such as $C_1$-$C_6$ alkoxy, e.g., methoxy. In certain embodiments, $R^{10}$ is hydroxyl. In certain embodiments, $R^{10}$ is acyl or acyloxy. In certain embodiments, $R^{10}$ is carboxyl or carboxyl ester. In certain embodiments, $R^{10}$ is sulfate. In certain embodiments, $R^4$ is azido. In certain embodiments, $R^4$ is amino or substituted amino. In certain embodiments, $R^4$ is nitro. In certain embodiments, $R^4$ is cyano. In certain embodiments, $R^4$ is acyl, carboxyl, or carboxylester. In certain embodiments, $R^4$ is cycloalkyl or substituted cycloalkyl. In certain embodiments, $R^4$ is heterocycloalkyl or substituted heterocycloalkyl. In certain embodiments, $R^4$ is aryl or substituted aryl. In certain embodiments, $R^4$ is heteroaryl or substituted heteroaryl.

In certain embodiments, $R^5$ is selected from hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl. In certain embodiments, $R^5$ is hydrogen. In certain embodiments, $R^5$ is alkyl or substituted alkyl. For example, $R^5$ may be $C_1$-$C_6$ alkyl, such as $C_1$-$C_3$ alkyl. In some instances, $R^5$ is methyl. In certain embodiments, $R^5$ is alkoxy or substituted alkoxy. For example, $R^5$ may be $C_1$-$C_6$ alkoxy, such as $C_1$-$C_3$ alkoxy. In some instances, $R^5$ is methoxy. In some instances, $R^5$ is substituted alkoxy, such as $C_1$-$C_6$ alkoxy, substituted with one or more groups, such as, but not limited to alkyl, substituted alkyl, alkoxy, substituted alkoxy, and the like. For example, $R^5$ may be substituted alkoxy, such as $C_1$-$C_6$ alkoxy, substituted with an alkoxy or substituted alkoxy. For instance, $R^5$ may include a polyethylene glycol group, such as —$(OCH_2CH_2)_n$—$R^{10}$, where n is an integer from 1 to 10 and $R^{10}$ is selected from alkyl, substituted alkyl, hydroxyl, alkoxy, substituted alkoxy, acyl, acyloxy, carboxyl, carboxyl ester and sulfate. In some instances, n is 1. In some instances, n is 2. In some instances, n is 3. In some instances, n is 4. In some instances, n is 5. In some instances, n is 6. For example, $R^5$ may be —$(OCH_2CH_2)_n$—$R^{10}$, where n is 3 and $R^{10}$ is methoxy. In some instances, $R^{10}$ is alkoxy, such as $C_1$-$C_6$ alkoxy, e.g., methoxy. In certain embodiments, $R^{10}$ is hydroxyl. In certain embodiments, $R^{10}$ is acyl or acyloxy. In certain embodiments, $R^{10}$ is carboxyl or carboxyl ester. In certain embodiments, $R^{10}$ is sulfate. In certain embodiments, $R^5$ is azido. In certain embodiments, $R^5$ is amino or substituted amino. In certain embodiments, $R^5$ is nitro. In certain embodiments, $R^5$ is cyano. In certain embodiments, $R^5$ is acyl, carboxyl, or carboxylester. In certain embodiments, $R^5$ is cycloalkyl or substituted cycloalkyl. In certain embodiments, $R^5$ is heterocycloalkyl or substituted heterocycloalkyl. In certain embodiments, $R^5$ is aryl or substituted aryl. In certain embodiments, $R^5$ is heteroaryl or substituted heteroaryl.

In certain embodiments, one of $R^1$, $R^2$, $R^3$, $R^4$ or $R^5$ together with its adjacent R-group form a cycloalkyl, substituted cycloalkyl, heterocycloalkyl, substituted heterocycloalkyl, aryl, substituted aryl, heteroaryl or substituted heteroaryl.

In certain embodiments, $R^1$ and $R^2$ together form a cycloalkyl, substituted cycloalkyl, heterocycloalkyl, substituted heterocycloalkyl, aryl, substituted aryl, heteroaryl or substituted heteroaryl. In certain embodiments, $R^1$ and $R^2$ together form a cycloalkyl or substituted cycloalkyl. In certain embodiments, $R^1$ and $R^2$ together form a heterocycloalkyl or substituted heterocycloalkyl. In certain embodiments, $R^1$ and $R^2$ together form an aryl or substituted aryl. In certain embodiments, $R^1$ and $R^2$ together form a heteroaryl or substituted heteroaryl.

In certain embodiments, $R^2$ and $R^3$ together form a cycloalkyl, substituted cycloalkyl, heterocycloalkyl, substituted heterocycloalkyl, aryl, substituted aryl, heteroaryl or substituted heteroaryl. In certain embodiments, $R^2$ and $R^3$ together form a cycloalkyl or substituted cycloalkyl. In certain embodiments, $R^2$ and $R^3$ together form a heterocycloalkyl or substituted heterocycloalkyl. In certain embodiments, $R^2$ and $R^3$ together form an aryl or substituted aryl. In certain embodiments, $R^2$ and $R^3$ together form a heteroaryl or substituted heteroaryl.

In certain embodiments, $R^3$ and $R^4$ together form a cycloalkyl, substituted cycloalkyl, heterocycloalkyl, substituted heterocycloalkyl, aryl, substituted aryl, heteroaryl or substituted heteroaryl. In certain embodiments, $R^3$ and $R^4$ together form a cycloalkyl or substituted cycloalkyl. In certain embodiments, $R^3$ and $R^4$ together form a heterocycloalkyl or substituted heterocycloalkyl. In certain embodiments, $R^3$ and $R^4$ together form an aryl or substituted aryl. In certain embodiments, $R^3$ and $R^4$ together form a heteroaryl or substituted heteroaryl.

In certain embodiments, $R^4$ and $R^5$ together form a cycloalkyl, substituted cycloalkyl, heterocycloalkyl, substituted heterocycloalkyl, aryl, substituted aryl, heteroaryl or substituted heteroaryl. In certain embodiments, $R^4$ and $R^5$ together form a cycloalkyl or substituted cycloalkyl. In certain embodiments, $R^4$ and $R^5$ together form a heterocycloalkyl or substituted heterocycloalkyl. In certain embodiments, $R^4$ and $R^5$ together form an aryl or substituted aryl. In certain embodiments, $R^4$ and $R^5$ together form a heteroaryl or substituted heteroaryl.

In certain embodiments, one of $R^1$, $R^2$, $R^3$, $R^4$ or $R^5$ together with its adjacent R-group form a cyclic group selected from cyclopropyl, cyclobutyl, cyclopentyl, cyclohexyl, phenyl, pyridinyl, piperidinyl, pyrazinyl, piperazinyl, pyrimidinyl, pyridazinyl, furyl, tetrahydrofuranyl, pyrrolyl, pyrrolidinyl, pyrazolyl, pyrazolidinyl, imidazolyl, imidazolidinyl, imidazolinyl, triazolyl, tetrazolyl, thiazolyl, isothiazolyl, oxazolyl, isoxazolyl, thiazolidinyl, thiophenyl, morpholinyl, thiomorpholinyl, and diaoxane.

In certain embodiments, one of $R^1$, $R^2$, $R^3$, $R^4$ or $R^5$ together with its adjacent R-group form a cyclic group selected from phenyl, pyrrolyl, and dioxane. In certain embodiments, one of $R^1$, $R^2$, $R^3$, $R^4$ or $R^5$ together with its adjacent R-group form a phenyl group. In certain embodiments, one of $R^1$, $R^2$, $R^3$, $R^4$ or $R^5$ together with its adjacent R-group form a pyrrolyl group. In certain embodiments, one of $R^1$, $R^2$, $R^3$, $R^4$ or $R^5$ together with its adjacent R-group form a dioxane group.

In certain embodiments, one of $R^1$, $R^2$, $R^3$, $R^4$ or $R^5$ is azido. In certain embodiments, $R^1$ is azido. In certain embodiments, $R^2$ is azido. In certain embodiments, $R^3$ is azido. In certain embodiments, $R^4$ is azido. In certain embodiments, $R^5$ is azido.

In certain embodiments, one of $R^1$, $R^2$, $R^3$, $R^4$ or $R^5$ is optionally a molecule of interest. In certain embodiments, $R^1$ is the molecule of interest. In certain embodiments, $R^2$ is the molecule of interest. In certain embodiments, $R^3$ is the molecule of interest. In certain embodiments, $R^4$ is the molecule of interest. In certain embodiments, $R^5$ is the molecule of interest. In certain embodiments, the molecule of interest is a toxin, a drug, a peptide, a nucleic acid (e.g., an oligonucleotide), a member of a specific binding pair, an epitope tag, or an affinity domain. In certain embodiments, the molecule of interest is a toxin. In certain embodiments, the molecule of interest is a drug. In certain embodiments, the molecule of interest is a peptide. In certain embodiments, the molecule of interest is a nucleic acid (e.g., an oligonucleotide). In certain embodiments, the molecule of interest is a member of a specific binding pair. In certain embodiments, the molecule of interest is an epitope tag or an affinity domain. Molecules of interest are described in more detail below.

In certain embodiments, two of $R^1$, $R^2$, $R^3$, $R^4$ and $R^5$ are hydrogen, one of $R^1$, $R^2$, $R^3$, $R^4$ or $R^5$ is azido, and one of $R^1$, $R^2$, $R^3$, $R^4$ or $R^5$ together with its adjacent R-group form a cycloalkyl, substituted cycloalkyl, heterocycloalkyl, substituted heterocycloalkyl, aryl, substituted aryl, heteroaryl or substituted heteroaryl. For example, one of $R^1$, $R^2$, $R^3$, $R^4$ or $R^5$ together with its adjacent R-group may form a cyclic group as described above (e.g., phenyl, pyrrolyl or dioxane).

In certain embodiments, three of $R^1$, $R^2$, $R^3$, $R^4$ and $R^5$ are hydrogen, one of $R^1$, $R^2$, $R^3$, $R^4$ or $R^5$ is azido, and one of $R^1$, $R^2$, $R^3$, $R^4$ and $R^5$ is alkyl, substituted alkyl, alkoxy, substituted alkoxy, heterocycloalkyl, or substituted heterocycloalkyl.

In certain embodiments, two of $R^1$, $R^2$, $R^3$, $R^4$ and $R^5$ are hydrogen, one of $R^1$, $R^2$, $R^3$, $R^4$ or $R^5$ is azido, and two of $R^1$, $R^2$, $R^3$, $R^4$ and $R^5$ are independently selected from alkyl, substituted alkyl, alkoxy, substituted alkoxy, heterocycloalkyl, and substituted heterocycloalkyl. For example, in some instances, two of $R^1$, $R^2$, $R^3$, $R^4$ and $R^5$ are hydrogen, one of $R^1$, $R^2$, $R^3$, $R^4$ or $R^5$ is azido, and two of $R^1$, $R^2$, $R^3$, $R^4$ and $R^5$ are alkoxy or substituted alkoxy. For example, two of $R^1$, $R^2$, $R^3$, $R^4$ and $R^5$ may be substituted alkoxy, such as $C_1$-$C_6$ alkoxy, substituted with an alkoxy or substituted alkoxy. For instance, two of $R^1$, $R^2$, $R^3$, $R^4$ and $R^5$ may include a polyethylene glycol group, such as —$(OCH_2CH_2)_n$—$R^{10}$, where n is an integer from 1 to 10 and $R^{10}$ is selected from alkyl, substituted alkyl, hydroxyl, alkoxy, substituted alkoxy, acyl, acyloxy, carboxyl, carboxyl ester and sulfate. In some instances, n is 1. In some instances, n is 2. In some instances, n is 3. In some instances, n is 4. In some instances, n is 5. In some instances, n is 6. For example, two of $R^1$, $R^2$, $R^3$, $R^4$ and $R^5$ may be —$(OCH_2CH_2)_n$—$R^{10}$, where n is 3 and $R^{10}$ is methoxy. In some instances, $R^1$ is —$(OCH_2CH_2)_n$—$R^{10}$, where n is 3 and $R^{10}$ is methoxy. In some instances, $R^3$ is —$(OCH_2CH_2)_n$—$R^{10}$, where n is 3 and $R^{10}$ is methoxy. In some instances, $R^4$ is azido. In some instances, $R^1$ is —$(OCH_2CH_2)_n$—$R^{10}$, where n is 3 and $R^{10}$ is methoxy; $R^3$ is —$(OCH_2CH_2)_n$—$R^{10}$, where n is 3 and $R^{10}$ is methoxy; and $R^4$ is azido.

In certain embodiments, a compound as described above is a compound of formula (II):

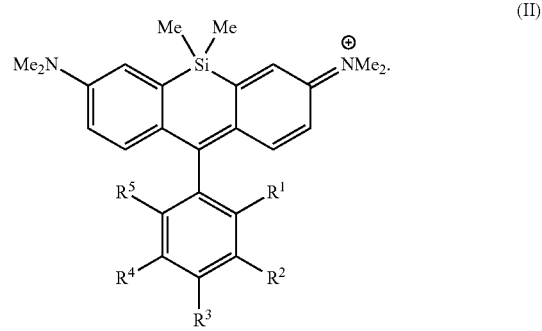

(II)

In certain embodiments, a compound of formula (II) includes $R^1$, $R^2$, $R^3$, $R^4$ and $R^5$ as described above for formula (I).

In certain embodiments, a compound as described above is a compound of formula (III):

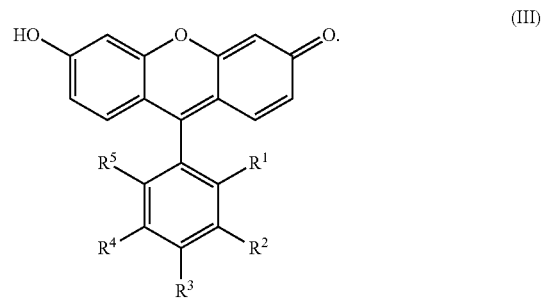

(III)

In certain embodiments, a compound of formula (III) includes $R^1$, $R^2$, $R^3$, $R^4$ and $R^5$ as described above for formula (I).

In certain embodiments, a compound as described above is a compound of formula (IV):

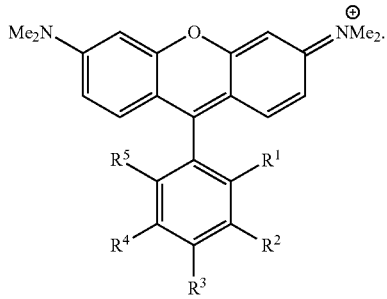

(IV)

In certain embodiments, a compound of formula (IV) includes $R^1$, $R^2$, $R^3$, $R^4$ and $R^5$ as described above for formula (I).

In certain embodiments, a compound as described above is a compound of formula (V):

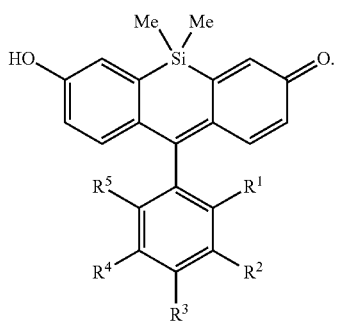

(V)

In certain embodiments, a compound of formula (V) includes $R^1$, $R^2$, $R^3$, $R^4$ and $R^5$ as described above for formula (I).

In certain embodiments, the substituted phenyl ring of a compound of formulae (I) to (V) is a substituted phenyl ring of the following structure:

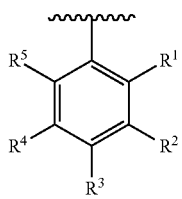

wherein $R^1$, $R^2$, $R^3$, $R^4$ and $R^5$ as described above for formula (I), where the wavy line indicates the attachment to the rest of the compound.

In certain embodiments, the substituted phenyl ring of a compound of formulae (I) to (V) is a substituted phenyl ring of the following structure:

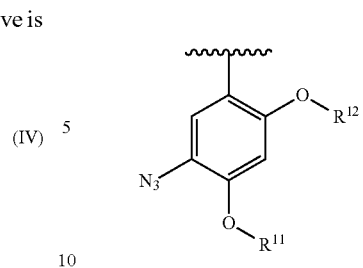

where $R^{11}$ and $R^{12}$ are each independently hydrogen, an alkyl, a substituted alkyl, a PEG, a zwitterionic group or a water solubilizing group (WSG). The term zwitterionic group refers to any convenient substituent that includes both a positively charged moiety (e.g., an amine, an ammonium, a sulfonium, a phosphonium, etc) and a negatively charged moiety (e.g., a sulfonate, a carboxylate, a phosphate, etc). Any convenient zwitterionic groups may be utilized in the subject compounds. In certain embodiments, $R^{11}$ and $R^{12}$ are each a WSG. In certain embodiments, $R^{11}$ and $R^{12}$ are each a zwitterionic group. In certain embodiments, $R^{11}$ and $R^{12}$ are each a PEG. In certain embodiments, $R^{11}$ and $R^{12}$ are each an alkyl. In certain embodiments, $R^{11}$ and $R^{12}$ are each a substituted alkyl. In certain embodiments, $R^{11}$ and $R^{12}$ are each hydrogen.

In some embodiments, the zwitterionic group is described by the formula: $-L^1-Z^1-L^2-Z^2$ where $L^1$ and $L^2$ are linkers and one of $Z^1$ and $Z^2$ is a positively charged group and the other of $Z^1$ and $Z^2$ is a negatively charged group. In certain instances, $Z^1$ and $Z^2$ are independently selected from ammonium, sulfonium, phosphonium, sulfonate, phosphate and carboxylate. In certain embodiments, the zwitterionic group is described by the formula:

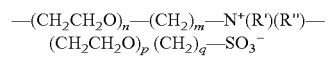

where n, m, p and q are each independently 0 or an integer from 1 to 6, R' and R" are each independently H, an alkyl or a substituted alkyl. In some cases, p is 0 and n, m, and q are each >0. In some cases, p is 0, n is 1-3, m is 2-3, and q is 2-4. In some cases, p is 0, n is 1, m is 2, and q is 3. In certain embodiments of the substituted phenyl ring, $R^{11}$ and $R^{12}$ are each a zwitterionic group described by the structure:

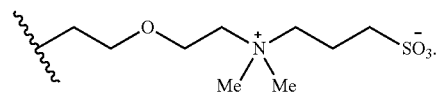

In certain embodiments, the substituted phenyl ring of a compound of formulae (I) to (V) is a substituted phenyl ring selected from the following structures:

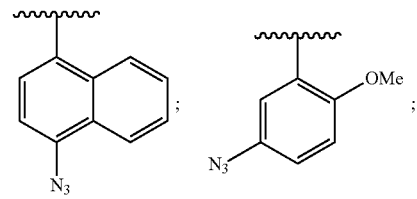

-continued
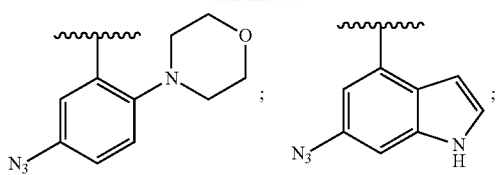
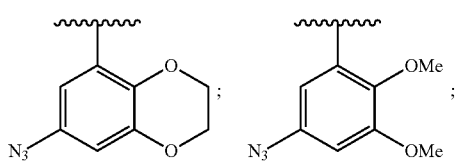
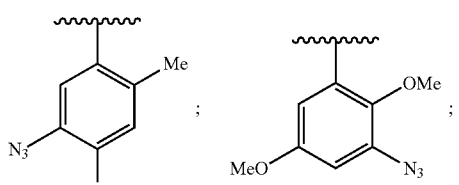
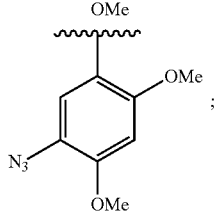
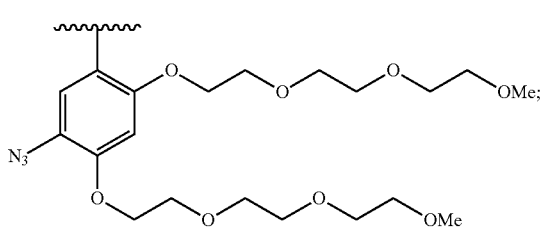
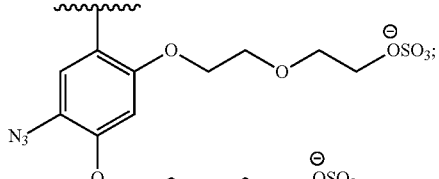
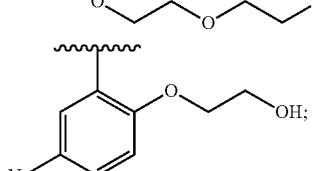
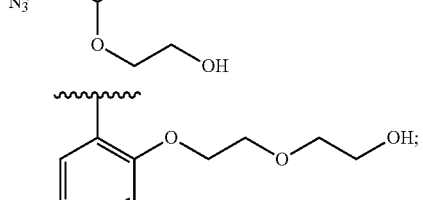
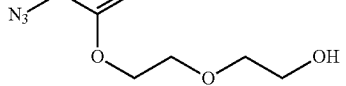
-continued
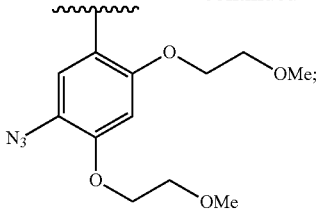
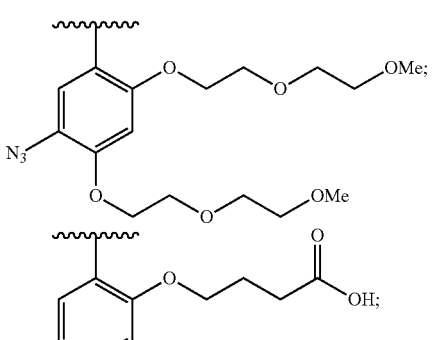
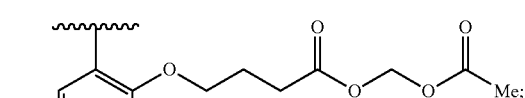
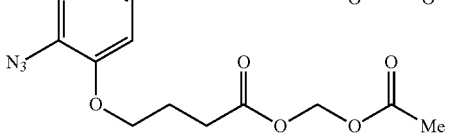
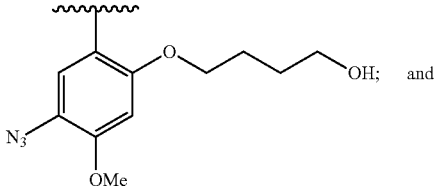
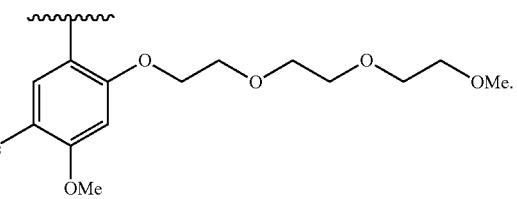
In certain embodiments, the substituted phenyl ring of a compound of formulae (I) to (V) is a substituted phenyl ring described by the following structure:
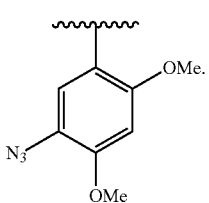 [SMILES: *c1cc(N=[N+]=[N-])c(OC)cc1OC]

In certain embodiments, the substituted phenyl ring of a compound of formulae (I) to (V) is a substituted phenyl ring described by the following structure:
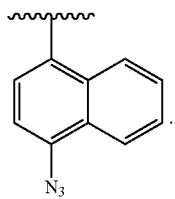 [SMILES: *c1ccc(N=[N+]=[N-])c2ccccc12]
In certain embodiments, a compound of formulae (I) to (V) is a compound selected from:
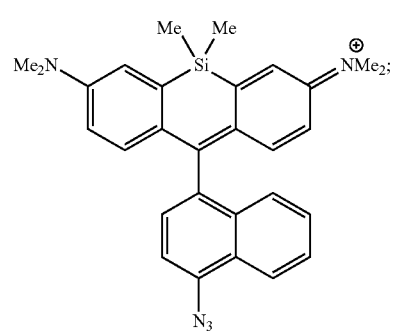
(Compound 1)
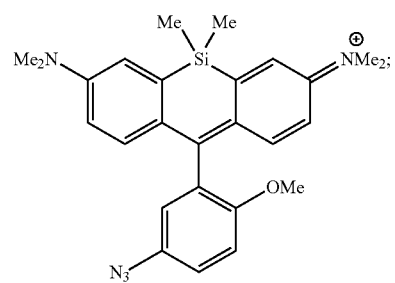
(Compound 2)
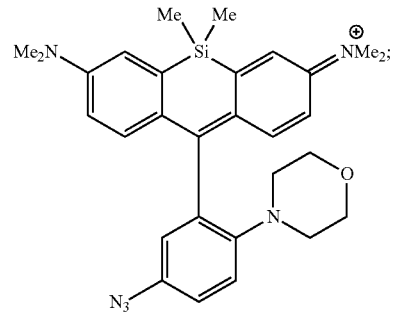
(Compound 3)
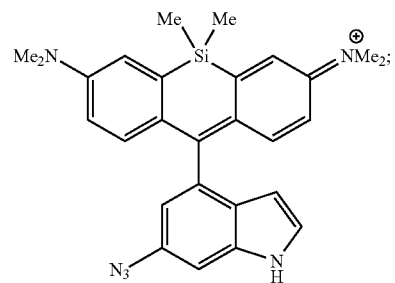
(Compound 4)
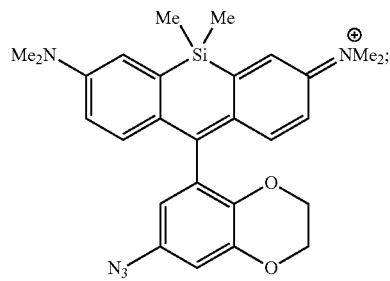
(Compound 5)
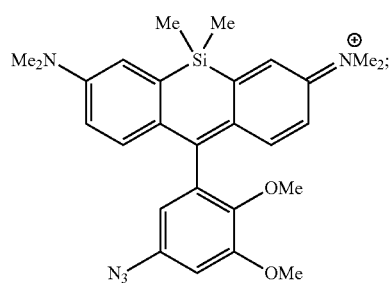
(Compound 6)
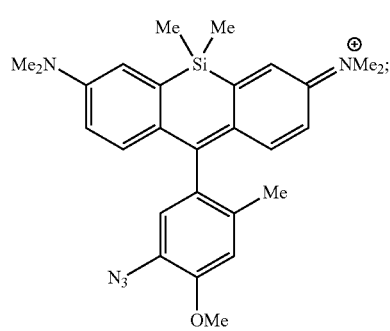
(Compound 7)
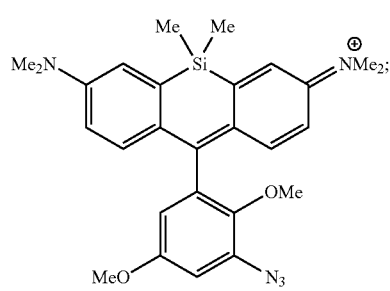
(Compound 8)
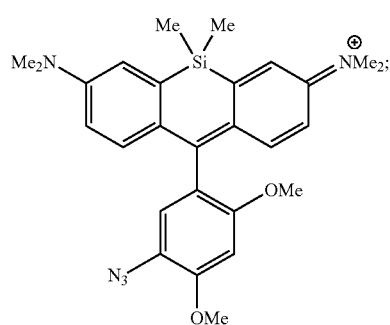
(Compound 9)

-continued

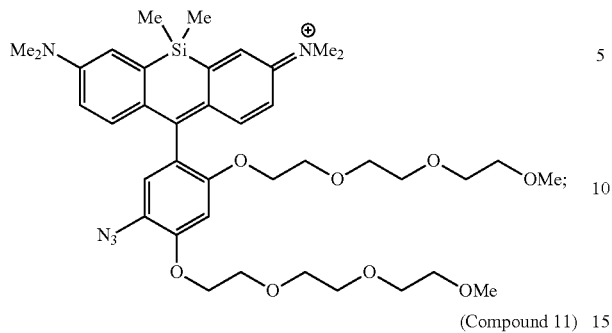

(Compound 10)
(Compound 11)
(Compound 12)
(Compound 13)
(Compound 14)

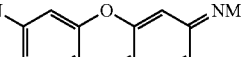

In certain embodiments, a compound of formulae (I) to (V) is a compound selected from:

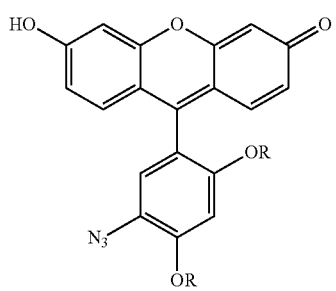

CalFluor 488

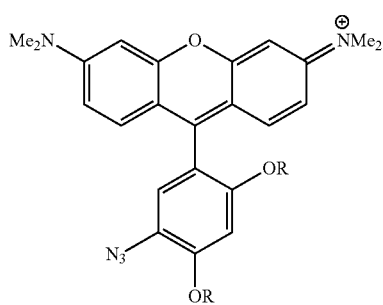

CalFluor 555

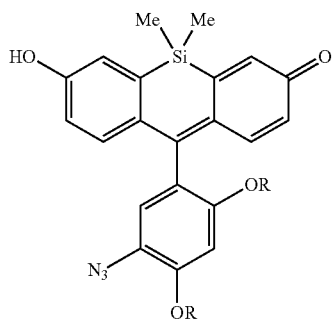

CalFluor 580

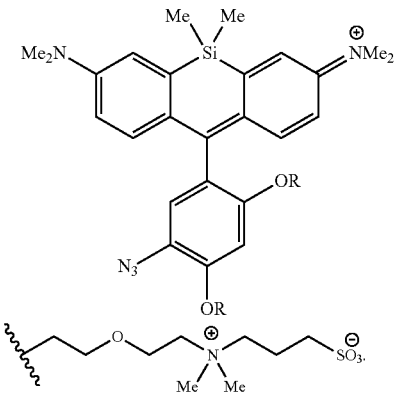

CalFluor 647

Molecules of Interest

As noted above, in certain embodiments, one of $R^1$, $R^2$, $R^3$, $R^4$ or $R^5$ is optionally a molecule of interest. In certain embodiments, $R^1$ is the molecule of interest. In certain embodiments, $R^2$ is the molecule of interest. In certain embodiments, $R^3$ is the molecule of interest. In certain embodiments, $R^4$ is the molecule of interest. In certain embodiments, $R^5$ is the molecule of interest. It is understood that the molecule of interest may be linked directly or indirectly to the azido-functionalized fluorogenic compound. In some instances, the molecule of interest is linked to the compound via an linker, e.g., one of $R^1$-$R^5$ is a -linker-molecule of interest. In certain embodiments, the molecule of interest is a toxin, a drug, a peptide, an oligonucleotide, a member of a specific binding pair, an epitope tag, or an affinity domain. In certain embodiments, the molecule of interest is a toxin. In certain embodiments, the molecule of interest is a drug. In certain embodiments, the molecule of interest is a peptide. In certain embodiments, the molecule of interest is a nucleic acid (e.g., an oligonucleotide). In certain embodiments, the molecule of interest is a member of a specific binding pair. In certain embodiments, the molecule of interest is an epitope tag. In certain embodiments, the molecule of interest is an affinity domain. Where one of $R^1$, $R^2$, $R^3$, $R^4$ or $R^5$ is optionally a molecule of interest, the molecule of interest does not sterically hinder chemical coupling of the compound of one of Formulas I-V via the azido group to the alkyne moiety of a target biomolecule.

Where one of $R^1$, $R^2$, $R^3$, $R^4$ or $R^5$ is an epitope tag, conjugation of a compound of one of Formulas I-V to an alkyne-modified target biomolecule provides for a epitope tag that can be detected using, e.g., an antibody specific for the epitope, thereby providing for detection and/or purification of a target biomolecule that is conjugated to a compound of one of Formulas I-V. Where one of $R^1$, $R^2$, $R^3$, $R^4$ or $R^5$ is an affinity domain, conjugation of a compound of one of Formulas I-V to an alkyne-modified target biomolecule provides for an affinity domain that can be used to purify a target biomolecule that is conjugated to a compound of one of Formulas I-V. Where one of $R^1$, $R^2$, $R^3$, $R^4$ or $R^5$ is a drug, conjugation of a compound of one of Formulas I-V to an alkyne-modified target biomolecule can provide for delivery of the drug to a cell comprising the target biomolecule. Where one of $R^1$, $R^2$, $R^3$, $R^4$ or $R^5$ is a cytotoxic compound, conjugation of a compound of one of Formulas I-V to an alkyne-modified target biomolecule can provide for killing of a cell comprising the target biomolecule.

Epitope Tags and Affinity Domains

Suitable epitope tags include, but are not limited to, hemagglutinin (HA; e.g., YPYDVPDYA; SEQ ID NO:1), FLAG (e.g., DYKDDDDK; SEQ ID NO:2), FLAG-C (e.g., DYKDDDDKC; SEQ ID NO:3, c-myc (e.g., EQKLISEEDL; SEQ ID NO:4), a metal ion affinity tag such as a polyhistidine tag (e.g., $His_6$), and the like.

Exemplary, non-limiting, affinity domains include His5 (HHHHH) (SEQ ID NO:5), HisX6 (HHHHHH) (SEQ ID NO:6), C-myc (EQKLISEEDL) (SEQ ID NO:7), Flag (DYKDDDDK) (SEQ ID NO:2), StrepTag (WSHPQFEK) (SEQ ID NO:8), hemagglutinin, e.g., HA Tag (YPYDVPDYA; SEQ ID NO:9), glutathinone-S-transferase (GST), thioredoxin, cellulose binding domain, RYIRS (SEQ ID NO:10), Phe-His-His-Thr (SEQ ID NO:11), chitin binding domain, S-peptide, T7 peptide, SH2 domain, C-end RNA tag, WEAAAREACCRECCARA (SEQ ID NO:12), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

Member of a Specific Binding Pair

A member of a pair of binding partners (a member of a specific binding pair) is referred to herein as a "specific binding partner." Suitable specific binding partners include, but are not limited to, a member of a receptor/ligand pair; a member of an antibody/antigen pair; a member of a lectin/carbohydrate pair; a member of an enzyme/substrate pair; biotin/avidin; biotin/streptavidin; digoxin/antidigoxin; and the like. Suitable specific binding partners include, but are not limited to a receptor ligand; a receptor for a ligand; a ligand-binding portion of a receptor; an antibody; an antigen-binding fragment of an antibody; an antigen; a hapten; a lectin; a lectin-binding carbohydrate; an enzyme substrate; an irreversible inhibitor of an enzyme (e.g., an irreversible inhibitor that binds a substrate binding site of an enzyme, e.g., a "suicide" substrate); and the like.

Suitable ligand members of receptor/ligand pairs include, but are not limited to, neurotransmitters such as opioid compounds, acetylcholine, and the like; viral proteins that bind to a cell surface receptor, e.g., human immunodeficiency virus gp120, and the like; hormones; and the like.

Suitable antigen-binding antibody fragments include $F(ab')_2$, $F(ab)_2$, Fab', Fab, Fv, scFv, and Fd fragments, single-chain antibodies, and fusion proteins comprising an antigen-binding portion of an antibody and a non-antibody protein (e.g., an antigen-binding fragment of an antibody fused to an immunoglobulin constant region).

Suitable haptens include, but are not limited to, (4-hydroxy-3-nitrophenyl) acetyl; diethylenetriaminepentaacetic acid (DTPA) or one of its metal complexes; paranitrophenyl; biotin; fluorescein isothiocyanate; and the like.

Drugs

Suitable drugs include, but are not limited to, cytotoxic compounds (e.g., cancer chemotherapeutic compounds); antiviral compounds; biological response modifiers (e.g., hormones, chemokines, cytokines, interleukins, etc.); microtubule affecting agents; hormone modulators; steroidal compounds; and the like.

Suitable cancer chemotherapeutic compounds include, but are not limited to, non-peptidic (e.g., non-proteinaceous) compounds that reduce proliferation of cancer cells; peptidic compounds that reduce proliferation of cancer cells; antimetabolite agents; cytotoxic agents; and cytostatic agents. Non-limiting examples of chemotherapeutic agents include alkylating agents, nitrosoureas, antimetabolites, antitumor antibiotics, plant (vinca) alkaloids, and steroid hormones.

Suitable agents that act to reduce cellular proliferation include, but are not limited to, alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Suitable antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable anti-proliferative natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g.

etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other suitable anti-proliferative cytotoxic agents are navelbene, CPT-11, anastrazole, letrazole, capecitabine, reloxafine, cyclophosphamide, ifosamide, and droloxafine.

Suitable microtubule affecting agents that have antiproliferative activity include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Suitable hormone modulators and steroids (including synthetic analogs) include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), Zoladex®, and the like. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are also suitable for attachment to a cycloalkyne moiety. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283, 253; 5,279,949; 5,274,137; 5,202,448; 5,200,534; 5,229,529; and EP 590,267, the disclosures of which are incorporated herein by reference in their entirety), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but are not limited to, galactose and mannose derivatives described in International Patent Application No. WO 99/18113, the disclosure of which is incorporated herein by reference in its entirety; piperazino and other derivatives described in WO 99/14209, the disclosure of which is incorporated herein by reference in its entirety; taxane derivatives described in WO 99/09021, WO 98/22451, and U.S. Pat. No. 5,869,680, the disclosures of which are incorporated herein by reference in their entirety; 6-thio derivatives described in WO 98/28288, the disclosure of which is incorporated herein by reference in its entirety; sulfenamide derivatives described in U.S. Pat. No. 5,821,263, the disclosure of which is incorporated herein by reference in its entirety; and taxol derivative described in U.S. Pat. No. 5,415,869, the disclosure of which is incorporated herein by reference in its entirety. The term "taxane" further includes prodrugs of paclitaxel including, but not limited to, those described in WO 98/58927; WO 98/13059; and U.S. Pat. No. 5,824,701, the disclosures of which are incorporated herein by reference in their entirety.

Suitable biological response include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; (9) inhibitors of angiogenesis; and the like.

Nucleic Acids

Suitable nucleic acids include, e.g., a polymer of nucleotides or nucleosides of any length, e.g., a polymer having a length of from 1 to 100 nucleotides or nucleosides, e.g., from 1 to 5, from 5 to 10, from 10 to 15, from 15 to 20, from 20 to 25, from 25 to 30, from 30 to 40, from 40 to 50, or from 50 to 100 nucleotides or nucleosides. A nucleic acid can include one or more modifications such as a modified phosphate backbone, or other modification that can enhance stability or other property of the nucleic acid.

Linkers

In some cases, a molecule of interest is attached to the aryl group via a linker. Suitable linkers include, but are not limited to, a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, a nitro, a peptide linker, and the like.

Exemplary peptide linkers for use in linking a molecule of interest will in some embodiments have a combination of glycine, alanine, proline and methionine residues. In some embodiments, a peptide linker comprises multiple serine residues, e.g., from 50% to 75%, or from 75% to 100% of the amino acids in the linker are serine residues. In some embodiments, a peptide linker comprises multiple glycine residues, e.g., from 50% to 75%, or from 75% to 100% of the amino acids in the linker are glycine residues. Any flexible linker, generally having a length of from 6 amino acids to 40 amino acids is suitable for use. Linkers may have virtually any sequence that results in a generally flexible peptide.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as high performance liquid chromatography (HPLC), preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Examples of synthetic routes that can be used to synthesize the compounds disclosed herein are described below.

Compounds of the present disclosure can be synthesized according to the general synthetic reaction scheme shown below. For example, water soluble 2,4-dialkoxy-5-azido-substituted Si-rhodamine derivatives may be prepared. In certain embodiments, a variety of other analogs may be prepared that have different properties, such as cell-permeability or cell-trappability. In some instances, variations in the R-groups of the analogs minimally perturb the electronics of the pendant aryl ring while changing the biochemical properties of the probes. In some embodiments, the compounds contain carboxylates or alcohols, which may serve as attachment points for conjugation onto surfaces or other molecules of interest.

In certain embodiments, the synthetic routes used to produce the compounds are efficient and modular. The use of different alcohols (Step 1, below) or xanthones (Step 5, below) facilitates the preparation of fluorogenic azide probes with varying excitation/emission wavelengths or physical/biochemical properties.

General Synthetic Reaction Scheme

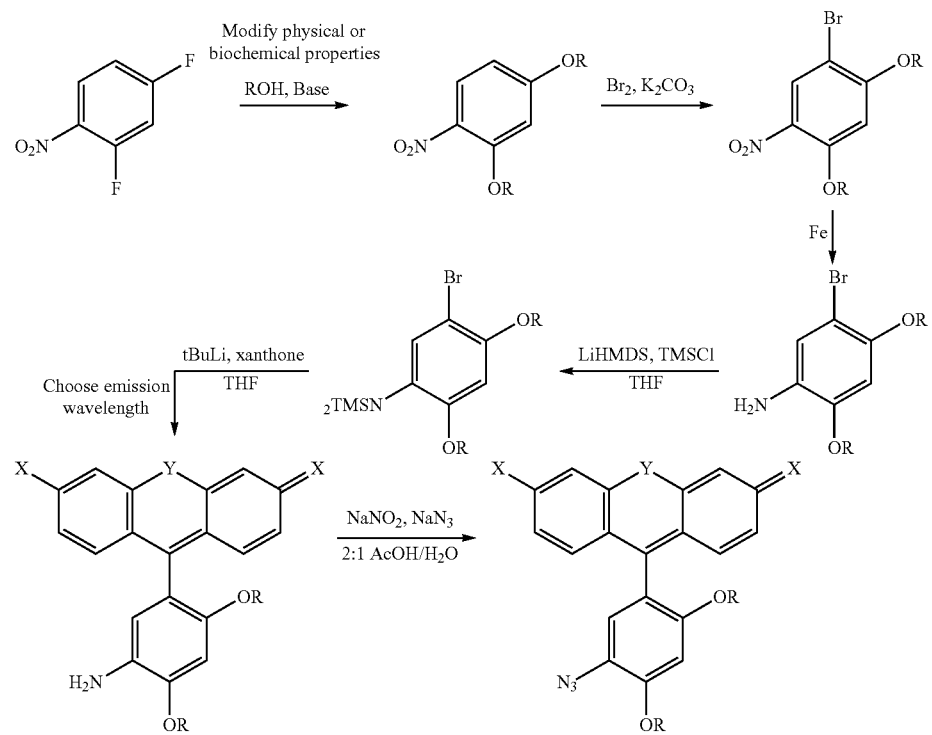

Labeling Methods

The present disclosure provides a method of labeling a target biomolecule comprising an alkyne, the method comprising contacting the biomolecule with an azido-functionalized fluorogenic compound of any one of Formulas I-V, as described above, wherein said contacting results in covalent linkage of the compound of any one of Formulas I-V with the alkyne moiety of the target biomolecule. The covalent linkage of a compound of any one of Formulas I-V with the alkyne moiety of the alkyne-containing target biomolecule is through the azido moiety of the compound of any one of Formulas I-V.

In some embodiments, a compound of any one of Formulas I-V provides for an emission maximum that is greater than 600 nm, e.g., greater than 625 nm, greater than 650 nm, greater than 675 nm, or greater than 700 nm. For example, a compound of any one of Formulas I-V, when conjugated to an alkyne-containing biomolecule, provides for an emission maximum that is greater than 600 nm, e.g., greater than 625 nm, greater than 650 nm, greater than 675 nm, or greater than 700 nm. For example, a compound of any one of Formulas I-V, when conjugated to an alkyne-containing biomolecule, provides for an emission maximum that is from 600 nm to about 610 nm, from about 610 nm to about 625 nm, from about 625 nm to about 650 nm, from about 650 nm to about 675 nm, from about 675 nm to about 700 nm, from about 700 nm to about 750 nm, or from about 750 nm to about 800 nm, or greater than 800 nm.

In some embodiments, a fluorogenic compound of any one of Formulas I-V, when conjugated to an alkyne-modified target biomolecule, provides for an at least 10-fold increase in fluorescence quantum yield, compared to the unconjugated compound of any one of Formulas I-V. In some cases, a fluorogenic compound of any one of Formulas I-V, when conjugated to an alkyne-modified target biomolecule, provides for an at least 10-fold, at least 15-fold, at least 20-fold, at least 25-fold, at least 30-fold, at least 35-fold, at least 40-fold, at least 45-fold, or more than 45-fold, increase in fluorescence quantum yield, compared to the unconjugated compound of any one of Formulas I-V.

A suitable target biomolecule includes, e.g., a sugar, an amino acid, a fatty acid, a nucleotide, a nucleoside, and the like, which contains, or is modified to contain, an alkyne. A suitable target biomolecule includes a macromolecule comprising a sugar, an amino acid, a fatty acid, a nucleotide, or a nucleoside, which contains, or is modified to contain, an alkyne. For example, a suitable target biomolecule includes a polysaccharide, a polypeptide, a lipid, a peptidoglycan, a lipopolysaccharide, a glycolipid, a lipoprotein, a glycoprotein, and the like, which contains, or is modified to contain, an alkyne.

In some cases, the target biomolecule is a sugar which contains, or is modified to contain, an alkyne. Suitable sugars include, e.g., glucose, glucosamine, acetyl glucosamine, fructose, galactose, galactosamine, mannose, mannosamine, or any other sugar or sugar analog. In some cases, the sugar is a substrate of sialic acid biosynthesis. In some cases, the sugar is mannosamine or acetylated mannosamine. As used herein, the term "sugar" or "saccharide," refers to a mono-, di-, tri-, or higher order saccharide or oligosaccharide. Representative monosaccharides include glucose, mannose, galactose, glucosamine, mannosamine, galactosamine, fructose, glyceraldehyde, erythrose, threose, ribose, arabinose, xylose, lyxose, allose, altrose, glucose, idose, talose, psicose, sorbose, and tagatose. Exemplary disaccharides include maltose, lactose, sucrose, cellobiose, trehalose, isomaltose, gentiobiose, melibiose, laminaribiose, chitobiose, xylobiose, mannobiose, sophorose, and the like. Certain tri- and higher oligosaccharides include raffinose, maltotriose, isomaltotriose, maltotetraose, maltopentaose, mannotriose, manninotriose, etc. Exemplary polysaccharides include starch, sodium starch glycolate, alginic acid, cellulose, carboxymethylcellulose, hydroxyethylcellulose, hydropropylcellulose, hydroxypropylmethylcellulose, ethylcellulose, carageenan, chitosan, chondroitin sulfate, heparin, hyaluronic acid, and pectinic acid.

In some cases, the target biomolecule is an amino acid which contains, or is modified to contain, an alkyne. The amino acid can be an encoded amino acid, a non-coded amino acid, an amino acid analog, or an amino acid derivative. Where the target molecule is a polypeptide, the polypeptide may comprise D-amino acids, L-amino acids, or both, and may be further modified, either naturally, synthetically, or recombinantly, to include other moieties. For example, the target polypeptide may be a lipoprotein, a glycoprotein, or other such modified protein.

Suitable amino acids include, but are not limited to, aliphatic amino acids, e.g., glycine, alanine, valine, leucine, and isoleucine; hydroxyl or sulfur/selenium-containing amino acids, e.g., serine, cysteine, selenocysteine, threonine, and methionine; cyclic amino acids, e.g., proline; aromatic amino acids, e.g., phenylalanine, tyrosine, and tryptophan; basic amino acids, e.g., histidine, lysine, and arginine; and acidic amino acids, e.g., aspartate, glutamate, asparagine, and glutamine. Suitable amino acids include, but are not limited to, hydroxyproline, β-alanine, o-aminobenzoic acid, m-aminobenzoic acid, p-aminobenzoic acid, m-aminomethylbenzoic acid, 2,3-diaminopropionic acid, a-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Suitable amino acids include, but are not limited to:
a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;
b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;
c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) substitution of side chain amide residue, including asparagine, glutamine, and alkyl or aromatic substituted derivatives of asparagine or glutamine; and f) substitution of hydroxyl containing amino acids, including serine, threonine, homoserine, 2,3-diaminopropionic acid, and alkyl or aromatic substituted derivatives of serine or threonine.

In some cases, the target biomolecule is a lipid which contains, or is modified to contain, an alkyne. In some cases, the target biomolecule is a lipid-containing macromolecule (e.g., glycolipids, lipopolysaccharides, lipoproteins, and the like) which contains, or is modified to contain, an alkyne.

In some cases, the target biomolecule is a nucleotide or nucleoside which contains, or is modified to contain, an alkyne.

In some cases, the method is carried out in aqueous conditions. In some cases, the reaction between an alkyne-containing target biomolecule and azido-functionalized fluorogenic compound of the present disclosure is performed under physiological conditions. For example, in some cases, the reaction between an alkyne-containing target biomolecule and azido-functionalized fluorogenic compound of the present disclosure is performed in a reaction that is essentially free of copper.

In some cases, the target biomolecule is expressed on a cell surface. In some cases, the target biomolecule is present intracellularly.

The target molecule can be naturally occurring, or may be synthetically or recombinantly produced, and may be isolated, substantially purified, or present within the native milieu of the unmodified molecule upon which the alkyne-containing target molecule is based (e.g., on a cell surface or within a cell, including within a host animal, e.g., a mammalian animal, such as a murine host (e.g., rat, mouse), hamster, canine, feline, bovine, swine, and the like). In some embodiments, the target molecule is present in vitro in a cell-free reaction. In other embodiments, the target molecule is present in a cell and/or displayed on the surface of a cell. In many embodiments of interest, the target molecule is in a living cell; on the surface of a living cell; in a living organism, e.g., in a living multicellular organism. Suitable living cells include cells that are part of a living multicellular organism; cells isolated from a multicellular organism; immortalized cell lines; and the like.

The present disclosure provides a method for labeling a cellular component, the method comprising: a) introducing an alkyne moiety into a cellular component, thereby generating an alkyne-modified cellular component; and b) contacting a cell comprising the alkyne-modified cellular component with a compound of any one of Formulas I-V as described herein, wherein said contacting results in covalent linkage of the compound of any one of Formulas I-V as described herein with the alkyne moiety of the alkyne-modified cellular component, thereby generating a labeled conjugate. In some cases, the cellular component comprises an amino acid, a fatty acid, or a sugar that is modified with the alkyne moiety. In some cases, the cellular component is a polypeptide or a polypeptide-containing macromolecule. In some cases, the cellular component is a lipid or a lipid-containing macromolecule. In some cases, the cellular component is a polysaccharide or a polysaccharide-containing macromolecule. In some cases, the cellular component is a lipid or a lipid-containing macromolecule. In some cases, the cellular component is a nucleic acid. The cell can be a prokaryotic cell or a eukaryotic cell. In some cases, the method further comprises detecting the labeled conjugate.

The step of contacting a cell comprising the alkyne-modified cellular component with a compound of any one of Formulas I-V as described herein, can be carried out in vitro (e.g., in an in vitro cell-free system), or in vivo. The step of contacting a cell comprising the alkyne-modified cellular component with a compound of any one of Formulas I-V as described herein, can be carried out under physiological conditions.

As noted above, in some cases, the method further comprises detecting the labeled conjugate. In some cases, the cell is not washed prior to detecting the conjugate.

Incorporating an Alkyne into a Biomolecule

A biomolecule can be modified to include an alkyne, generating an alkyne-modified biomolecule. In some cases, an alkyne suitable for use in modifying a biomolecule is a cycloalkyne, e.g., a cyclooctyne.

Methods for introducing an alkyne (e.g., a cyclooctyne) into a protein are known in the art; any known method can be used. For example, incorporation of an alkyne (e.g., a cyclooctyne) into a polypeptide (by reaction with an amino acid residue) can be carried out as described in Lang et al. (2012) *J. Am. Chem. Soc.* 134:10317; Plass et al. (2011) *Angew. Chem. Int. Ed. Engl.* 50:3878; and Borrmann et al. (2012) *Chembiochem.* 13:2094. As another example, incorporation of an alkyne (e.g., a cyclooctyne) into a lipid can be carried out as described in Neef and Schultz (2009) *Angew. Chem. Int. Ed. Engl.* 48:1498. Incorporation of an alkyne (e.g., a cyclooctyne) into a saccharide (by reaction with a sugar moiety) can be carried out as described in the Examples.

Alkynyl groups and chemistries of interest include, but are not limited to: the cycloalkyne and heterocycloalkyne groups described by Bertozzi et al. in U.S. patent application Ser. No. 12/049,034, filed Mar. 14, 2008; the modified cycloalkyne groups described by Jewett et al. in U.S. patent application Ser. No. 13/024,908, filed Feb. 10, 2011; the fused cyclooctyne compounds described by Van Delft et al. in WO/2011/136645, which applications are incorporated herein by reference in their entirety.

Utility

Compositions and methods of the present disclosure are useful in a variety of applications, including research applications, diagnostic applications, and synthetic applications (e.g., materials applications).

Research Applications

In some embodiments, the subject azido-functionalized fluorogenic compound, and subject labelling methods, are useful in research applications. Applications of interest include research applications, e.g., exploring functional and physical characteristics of a receptor; proteomics; metabolomics; development; and the like. Research applications also include drug discovery or other screening applications.

Proteomics aims to detect, identify, and quantify proteins to obtain biologically relevant information. Metabolomics is the detection, identification, and quantification of metabolites and other small molecules such as lipids and carbohydrates. Fiehn (2001) *Comparative and Functional Genomics* 2:155-168; and U.S. Pat. No. 6,873,914.

As an example, a subject azido-functionalized fluorogenic compound and a subject method can be used to image peptidoglycan in a bacterium.

In some cases, the bacterium is an obligate intracellular pathogen or a facultative intracellular pathogen. Examples of such bacteria include, e.g., a *Mycobacterium* species. Examples of species of *Mycobacterium* include, but are not limited to, *M. tuberculosis, M. bovis, M. bovis* strain *Bacillus* calmette-guerin (BCG) including BCG substrains, *M. avium, M. intracellulare, M. africanunum, M. kansasii, M. marinum, M. ulcerans* and *M. paratuberculosis*. Examples of other obligate and facultative intracellular bacterial species include, but are not limited to, *Legionella pneumophila*, other *Legionella* species, *Salmonella typhi*, other *Salmonella* species, *Shigella* species, *Listeria monocytogenes, Staphylococcus aureus, Staphylococcus epidermidis, Bacteroides fragilis*, other *Bacteroides* species, *Chlamydia pneumoniae, Chlamydia trachomatis, Chlamydia psittaci, Coxiella burnetii*, other Rickettsial species, and *Ehrlichia* species.

Suitable bacteria include, but are not limited to, *Francisella tularensis; Listeria monocytogenes; Salmonella; Brucella; Legionella pneumophila; Mycobacterium* (e.g., *M. tuberculosis, M. leprae, M. bovis, M. avium, M. abscessus*); *Nocardia* (e.g., *N. asteroids, N. farcinica, N. nova, N. transvalensis, N. brasiliensis, N. pseudobrasiliensis*); *Rhodococcus equui; Yersinia pestis; Neisseria* (e.g., *N. meningitidis, N. gonorrhoeae*); *Shigella* (e.g., *S. dysenteriae, S. flexneri, S. boydii*, and *S. sonnei*); *Chlamydia* (*C. trachomatis, C. pneumoniae, C. psittaci*); *Rickettsia;* and *Coxsiella.* Other suitable bacteria include, e.g., pathogens such as *Vibrio cholerae, Pseudomonas aeruginosa*, and pathogenic *Escherichia coli*; model organisms such as *Escherichia coli, Bacillus subtilis*, and *Caulobacter cresentus*; facultative pathogens such as Streptococcal and Clostridial species; and commensals such as *Bacteroides thetaiotamicron.*

As another example, subject azido-functionalized fluorogenic compound and a subject method can be used to track development of a multicellular organism.

As another example, subject azido-functionalized fluorogenic compound and a subject method can be used for labeling a large panel of alkyne-functionalized biomolecules in both live and fixed cells, in tissue and in vivo. In some cases, the cells that are labeled using a subject method are eukaryotic cells. In some cases, the cells that are labeled using a subject method are mammalian cells (including live cells in vitro; fixed cells in vitro; cells in tissue in vitro; cells in vitro, live cells in vivo; etc.). In some cases, the cells that are labeled using a subject method are amphibian cells (including live cells in vitro; fixed cells in vitro; cells in tissue in vitro; cells in vitro, live cells in vivo; etc.). In some cases, the cells that are labeled using a subject method are plant cells (including live cells in vitro; fixed cells in vitro; cells in tissue in vitro; cells in vitro, live cells in vivo; etc.). In some cases, the cells that are labeled using a subject method are reptile cells (including live cells in vitro; fixed cells in vitro; cells in tissue in vitro; cells in vitro, live cells in vivo; etc.). In some cases, the cells that are labeled using a subject method are parasite cells (including live cells in vitro; fixed cells in vitro; cells in tissue in vitro; cells in vitro, live cells in vivo; etc.).

In some embodiments, a subject azido-functionalized fluorogenic compound, and subject labelling methods, are useful for visualization of nucleic acids in a cell or tissue, in vitro, ex vivo, or in vivo. In some embodiments, a subject azido-functionalized fluorogenic compound, and subject labelling methods, are useful for visualization of newly-synthesized nucleic acids, e.g., newly-synthesized nucleic acids in a cell. In some embodiments, a subject azido-functionalized fluorogenic compound, and subject labelling methods, are useful for visualization of EdU-labeled DNA.

In some embodiments, a subject azido-functionalized fluorogenic compound, and subject labelling methods, are useful for cell surface labeling of eukaryotic cells (e.g., mammalian cells; amphibian cells; fish cells; etc.). In some embodiments, a subject azido-functionalized fluorogenic compound, and subject labelling methods, are useful for cell surface labeling of glycoconjugates on eukaryotic cells (e.g., mammalian cells; amphibian cells; fish cells; etc.).

Diagnostic Applications

In some embodiments, a subject azido-functionalized fluorogenic compound, and subject labelling methods, are useful in diagnostic applications. For example, a subject method of labeling a target biomolecule comprising an alkyne, the method comprising contacting the biomolecule with an azido-functionalized fluorogenic compound of any one of Formulas I-V, as described above, wherein said contacting results in covalent linkage of the compound of any one of Formulas I-V with the alkyne moiety of the target biomolecule, can be used to label a target biomolecule in the context of diagnosis. As an example, where the target biomolecule is a disease-associated biomolecule, labelling of the target biomolecule can provide for one or more of: detection of a disease state; localization of diseased tissue within the body; monitoring of disease progression; and assessment of efficacy of treatment for a disease. In some embodiments, the subject azido-functionalized fluorogenic compound, and subject labelling methods, are useful for analysis of living cells. In some embodiments, the subject azido-functionalized fluorogenic compound, and subject labelling methods, are useful for analysis of fixed cells (e.g., cells fixed for histological examination). In some embodiments, the subject azido-functionalized fluorogenic compound, and subject labelling methods, are useful for histological analysis of a cell sample obtained from an individual (e.g., a mammalian individual, e.g., a human). As another example, a subject azido-functionalized fluorogenic compound, and a subject method, can be used for labeling a large panel of alkyne-functionalized biomolecules in both live and fixed cells, in tissue and in vivo. For example, a subject azido-functionalized fluorogenic compound, and a subject method, can be used for labeling a large panel of alkyne-functionalized biomolecules in live cells in vitro; fixed cells in vitro; cells in tissue in vitro; cells in vitro, live cells in vivo; etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Synthesis and Evaluation of Azido Si-Rhodamines

Figure 2:
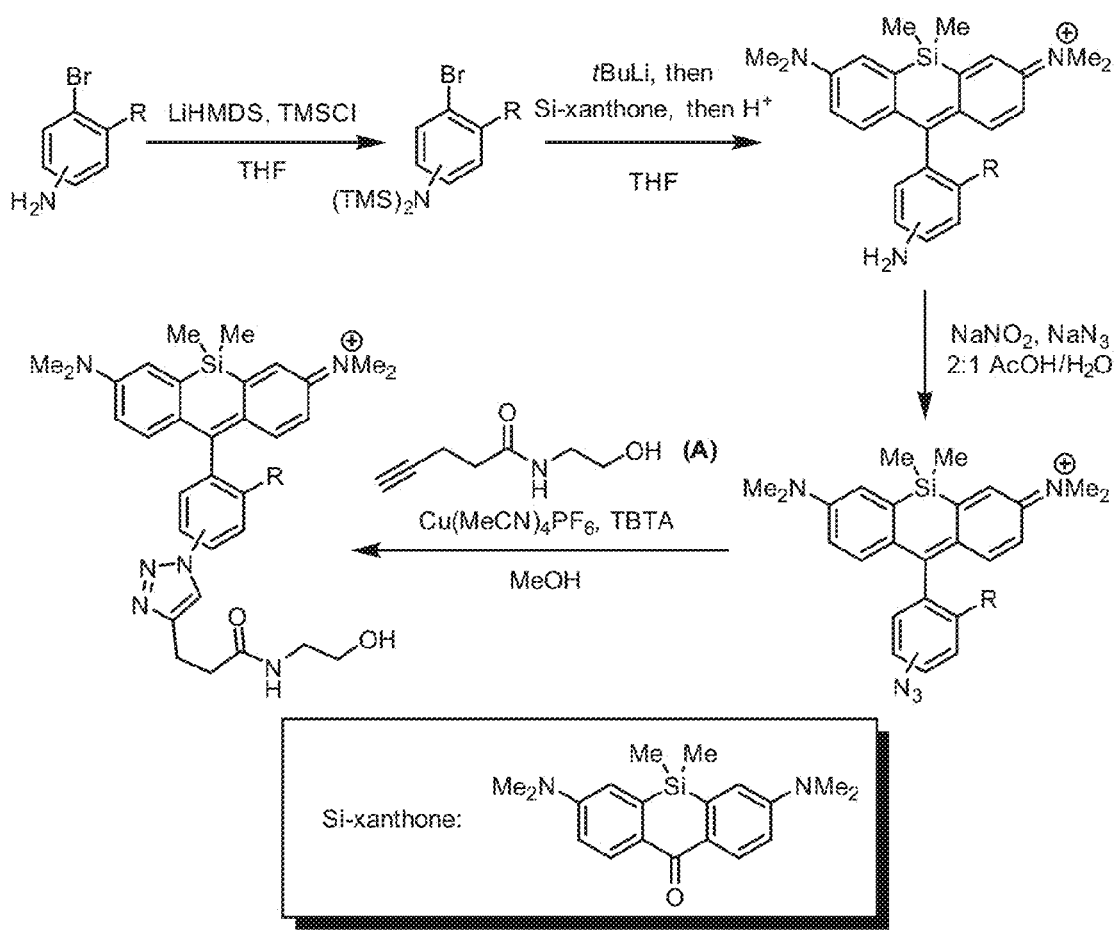
FIG. 2. shows a scheme for the synthesis of amino, azido and triazolyl Si-rhodamines from bromoanilines tBuLi=tert-butyl lithium, TBTA=tris[(1-benzyl-1H-1,2,3-triazol-4-yl)methyl]amine, according to embodiments of the present disclosure.
Figure 3:
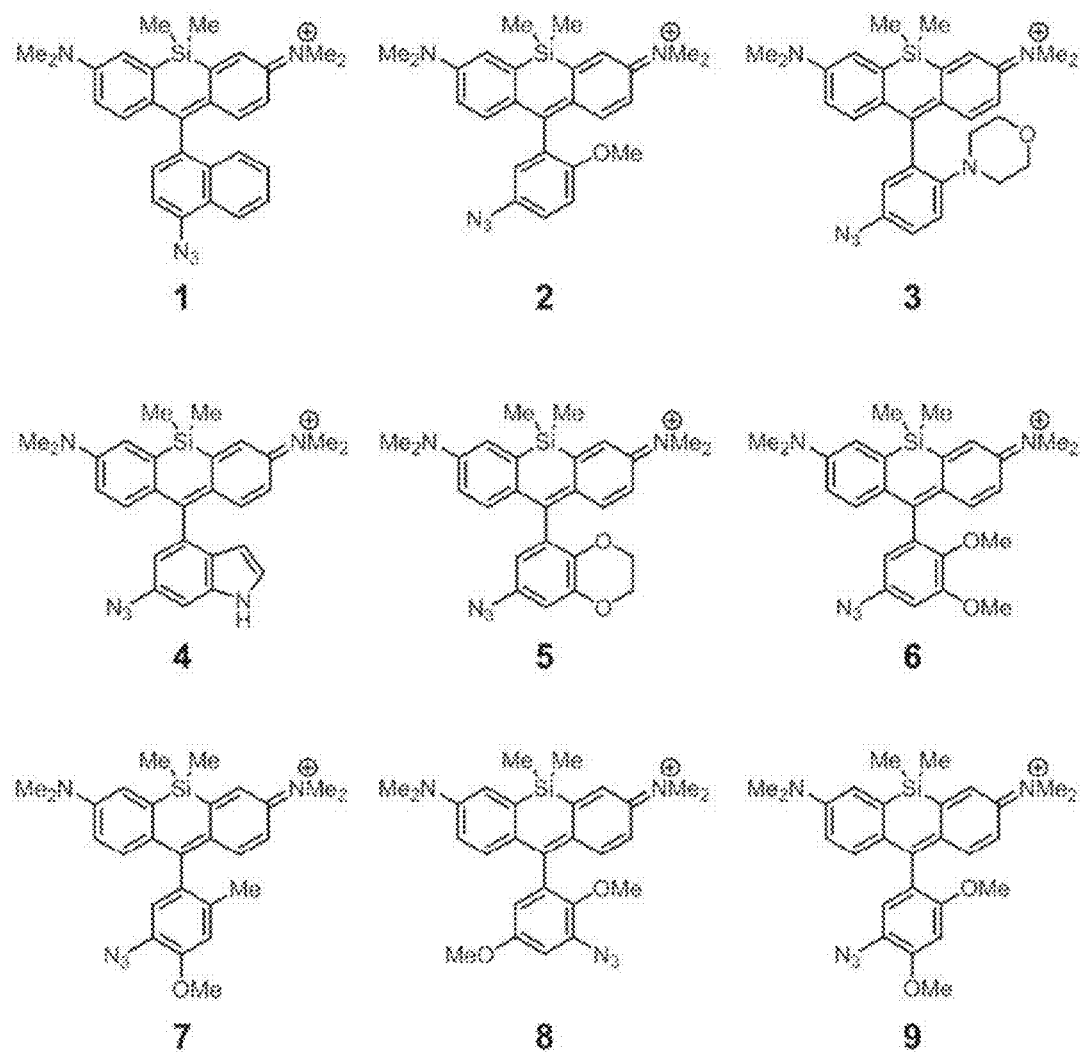
FIG. 3 shows structures of azido Si-rhodamines synthesized and evaluated, according to embodiments of the present disclosure.

An efficient and modular synthesis to access azide-functionalized Si-rhodamines from various bromoanilines was developed (FIG. 2). The bromoanilines were first protected as the bis-trimethylsilyl (TMS) derivatives by deprotonation with lithium hexamethyldisilazide (LiHMDS) and reaction with trimethylsilyl chloride (TMSCl). Next, the protected bromoanilines were subjected to lithium-halogen exchange and added into Si-xanthone, which afforded the amino Si-rhodamines after acidic workup. As described below, the photophysical properties of these intermediates were measured in comparison to their azido and triazolyl counterparts. The amino Si-rhodamines were finally subjected to diazotization with sodium nitrite and displacement by azide ion to yield the desired azido Si-rhodamines. Through this route, compounds 1-9 (FIG. 3) were generated. To evaluate fluorescence enhancement upon triazole formation, the corresponding triazolyl Si-rhodamines were synthesized by copper-catalyzed click chemistry with 4-pentynoyl ethanolamine amide (compound A, FIG. 2).

The fluorescence quantum yields of the purified amino, azido, and triazolyl Si-rhodamines were measured in pH 7.4 phosphate buffered saline (PBS) using cresyl violet in methanol ($\Phi fl$=0.54) as a standard (Table 1). The four analogs containing the same pendant aryl rings from our previous study 30 (1 to 4, FIG. 3) did not display significant fluorescence enhancement upon triazole formation. The best candidate of the four, 8-azidonaphthyl-substituted Si-rhodamine 1, afforded only a 5-fold increase in fluorescence quantum yield as compared with the 29-fold enhancement observed with the corresponding fluorescein. This result was not unexpected given the difference in electronics between the two systems and previous observation that more electron-rich pendant aryl rings are needed to quench fluorescence via PeT in Si-rhodamines.

Figure 9:
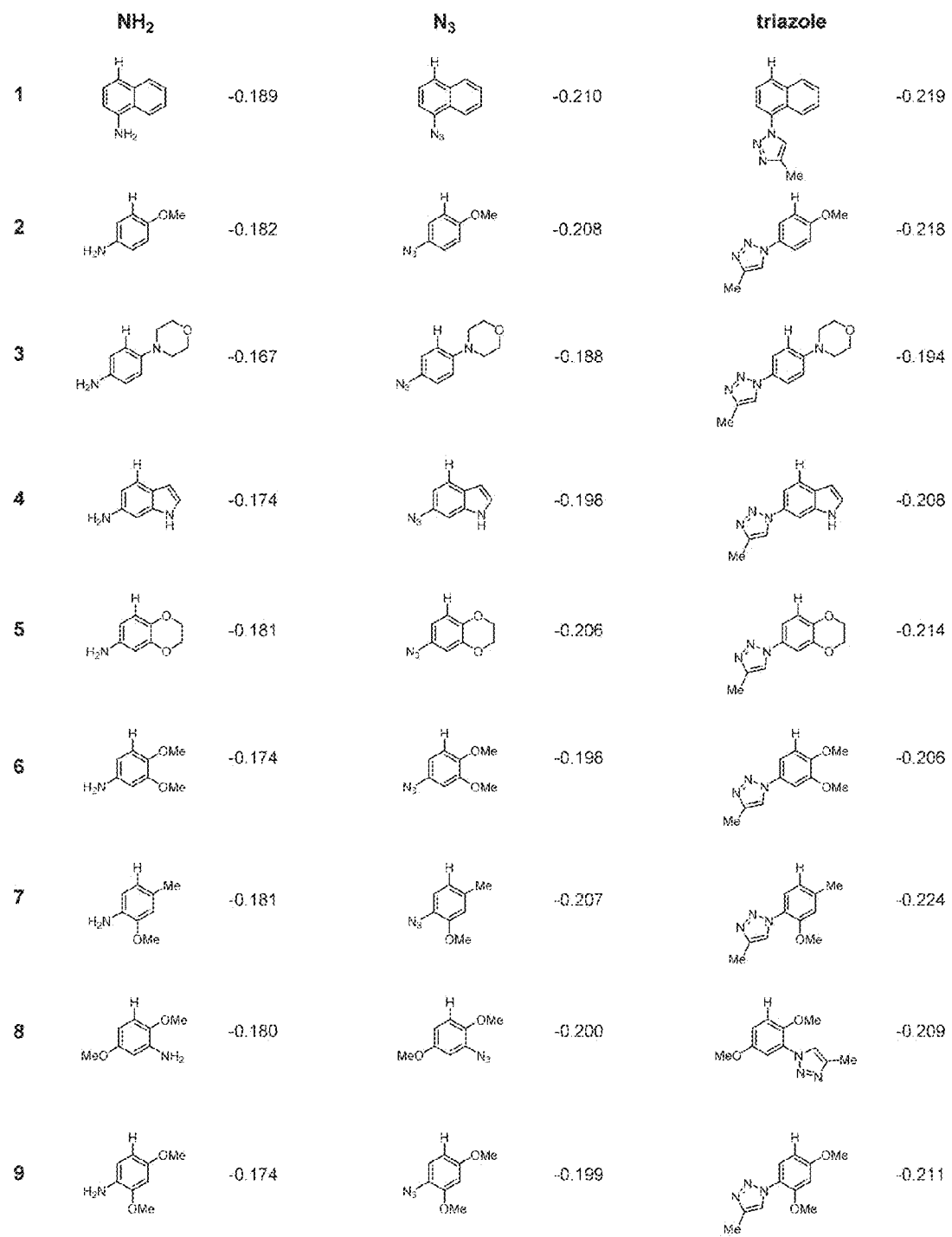
FIG. 9 shows structures and calculated aryl $E_{HOMO}$s in Hartrees of the pendant aryl rings of evaluated probes 1 to 9, according to embodiments of the present disclosure. The H represents the attachment point onto the xanthene moiety. The triazole substituent was truncated as a methyl group to simplify calculations.
Figure 10:
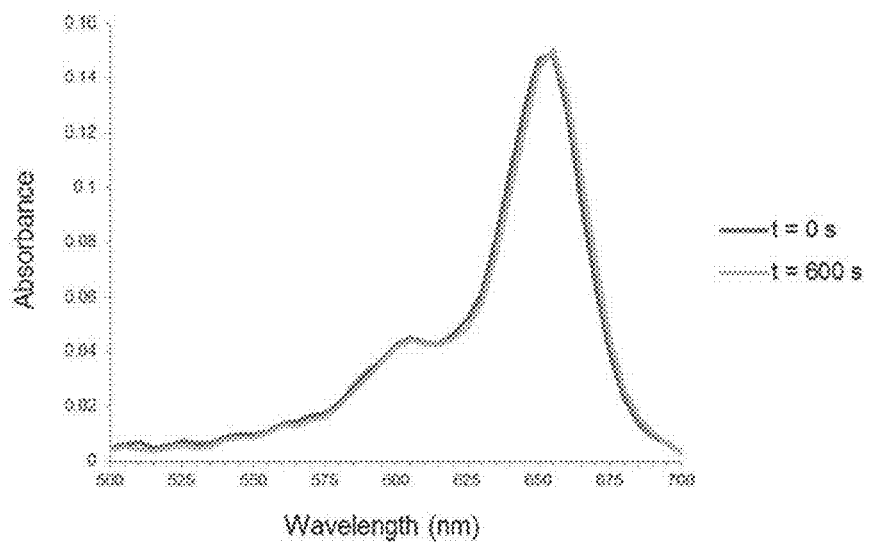
FIG. 10 shows absorption spectra of 9 under the copper-catalyzed click reaction conditions described above, according to embodiments of the present disclosure.

Computational results suggested that the pendant aryl rings of compounds 5-9 possess higher electron density than that of compound 1 (FIG. 9). These compounds were synthesized, and their photophysical properties experimentally characterized (Table 1). 3-Azido-4,6-dimethoxy-Si-rhodamine 9 (FIG. 3), the most promising of this group, displayed a 48-fold increase in fluorescence quantum yield upon triazole formation. This fluorescence enhancement was recapitulated in situ by monitoring fluorescence immediately after addition of alkyne A to a solution of CuSO4, the ligand BTTAA (BTTAA=2-[4-({bis[(1-tert-butyl-1H-1,2,3-triazol-4-yl)methyl]amino}methyl)-1H-1,2,3-triazol-1-yl]acetic acid), sodium ascorbate and compound 9 (FIG. 4). Under these conditions, the absorption of the compound did not change significantly (FIG. 10), indicating that the observed change in fluorescence intensity arises solely from an increase in fluorescence quantum yield.

TABLE 1

Photophysical properties of Si-rhodamines 1-9 and their amino and triazolyl counterparts in PBS pH 7.4.

| Compound | $\lambda_{abs}$ (nm) | $\lambda_{em}$ (nm) | $\Phi_{fl}$ | Change in $\Phi_{fl}$ |
|---|---|---|---|---|
| 1-NH$_2$ | 653 | 669 | 0.0016 | 24-fold ↓ |
| 1-N$_3$ | 654 | 666 | 0.038 | — |
| 1-triazole | 656 | 670 | 0.19 | 5.0-fold ↑ |
| 2-NH$_2$ | 650 | 669 | 0.0025 | 32-fold ↓ |
| 2-N$_3$ | 653 | 667 | 0.081 | — |
| 2-triazole | 655 | 669 | 0.19 | 2.3-fold ↑ |
| 3-NH$_2$ | 650 | 672 | 0.00096 | 1.4-fold ↓ |
| 3-N$_3$ | 656 | 667 | 0.0014 | — |
| 3-triazole | 663 | 676 | 0.0015 | 1.1-fold ↑ |
| 4-NH$_2$ | 650 | 673 | 0.00088 | 5.5-fold ↓ |
| 4-N$_3$ | 660 | 669 | 0.0048 | — |
| 4-triazole | 654 | 668 | 0.0088 | 1.8-fold ↑ |
| 5-NH$_2$ | 653 | 667 | 0.00093 | 21-fold ↓ |
| 5-N$_3$ | 655 | 668 | 0.019 | — |
| 5-triazole | 656 | 668 | 0.18 | 9.5-fold ↑ |
| 6-NH$_2$ | 652 | 665 | 0.00067 | 58-fold ↓ |
| 6-N$_3$ | 654 | 669 | 0.039 | — |
| 6-triazole | 656 | 670 | 0.18 | 4.6-fold ↑ |
| 7-NH$_2$ | 648 | 669 | 0.0015 | 45-fold ↓ |
| 7-N$_3$ | 650 | 666 | 0.066 | — |
| 7-triazole | 652 | 666 | 0.25 | 3.7-fold ↑ |
| 8-NH$_2$ | 654 | 672 | 0.0012 | 41-fold ↓ |
| 8-N$_3$ | 655 | 669 | 0.051 | — |
| 8-triazole | 657 | 671 | 0.16 | 3.2-fold ↑ |
| 9-NH$_2$ | 650 | 664 | 0.0014 | 3.0-fold ↓ |
| 9-N$_3$ | 654 | 666 | 0.0042 | — |
| 9-triazole | 655 | 668 | 0.20 | 48-fold ↑ |

Figure 11:
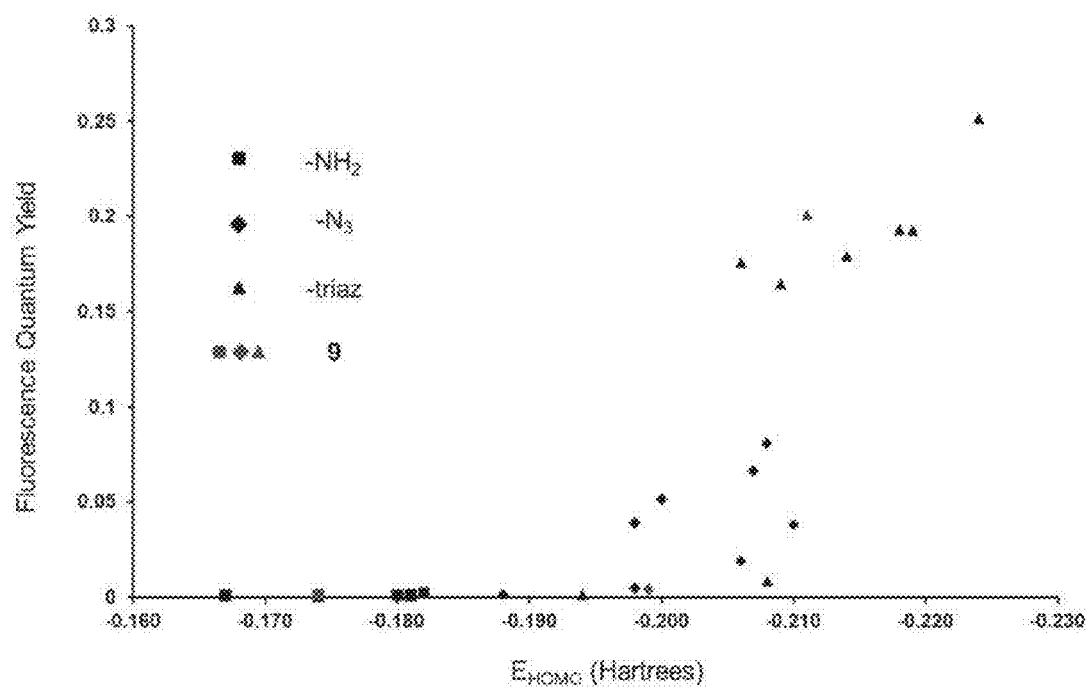
FIG. 11 shows a graph of fluorescence quantum yield vs. calculated $E_{HOMO}$s. The points highlighted in red correspond to derivatives of 9, according to embodiments of the present disclosure.

An interesting feature of compounds 1-9 is that their fluorescence quantum yields, which are already lower than those of the corresponding triazoles, are even further reduced by conversion to the corresponding amines (Table 1), a potential route of biological degradation. Thus, azide reduction, if it occurs, will suppress rather than enhance background fluorescence for this set of azido Si-rhodamine probes. This property stands in contrast to probes where azide reduction is a key part of sensor design. While a trend exists between calculated EHOMO and fluorescence quantum yield for compounds 1-9 (FIG. 11), the observed differences in quantum yields for some compounds with similar EHOMOs (for example, compare the data for compounds 8 and 9 in Table 1) suggests that other factors might influence PeT efficiency, or that other fluorescence quenching mechanisms are at play.

Optimization of Azido Si-Rhodamine 9 for Mammalian Cell Surface Labeling

Figure 12:
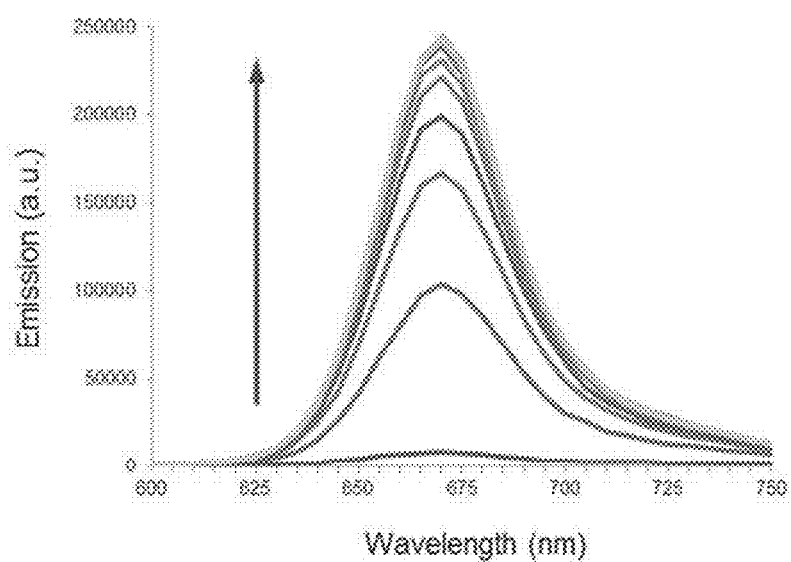
FIG. 12 shows a graph of emission spectra of 10 under the copper-catalyzed reaction conditions described above. Emission scans were taken every 30 seconds, with excitation at 600 nm, according to embodiments of the present disclosure.

Compound 9 was tested as a biological imaging reagent using mammalian cells that had been metabolically labeled with peracetylated N-pentynoylmannosamine (Ac4ManNAl), which is metabolized to N-pentynoyl sialic acid (SiaNAl) and presented on cell-surface glycoconjugates. However, compound 9 showed significant alkyne-independent background labeling even after repeated washing steps, most likely due to its substantial hydrophobic character. It was hypothesized that replacing the methoxy groups with more water soluble alkoxy substituents would maintain the electronic balance between the pendant aryl and the Si-xanthene moieties while enhancing hydrophilicity. To this end, compound 10 was synthesized in six steps from 2,4-difluoronitrobenzene (FIG. 5, and Scheme 1). Consistent with the hypothesis, compound 10 underwent a significant fluorescence enhancement upon copper-catalyzed click reaction with alkyne A (FIG. 12).

Figure 13:
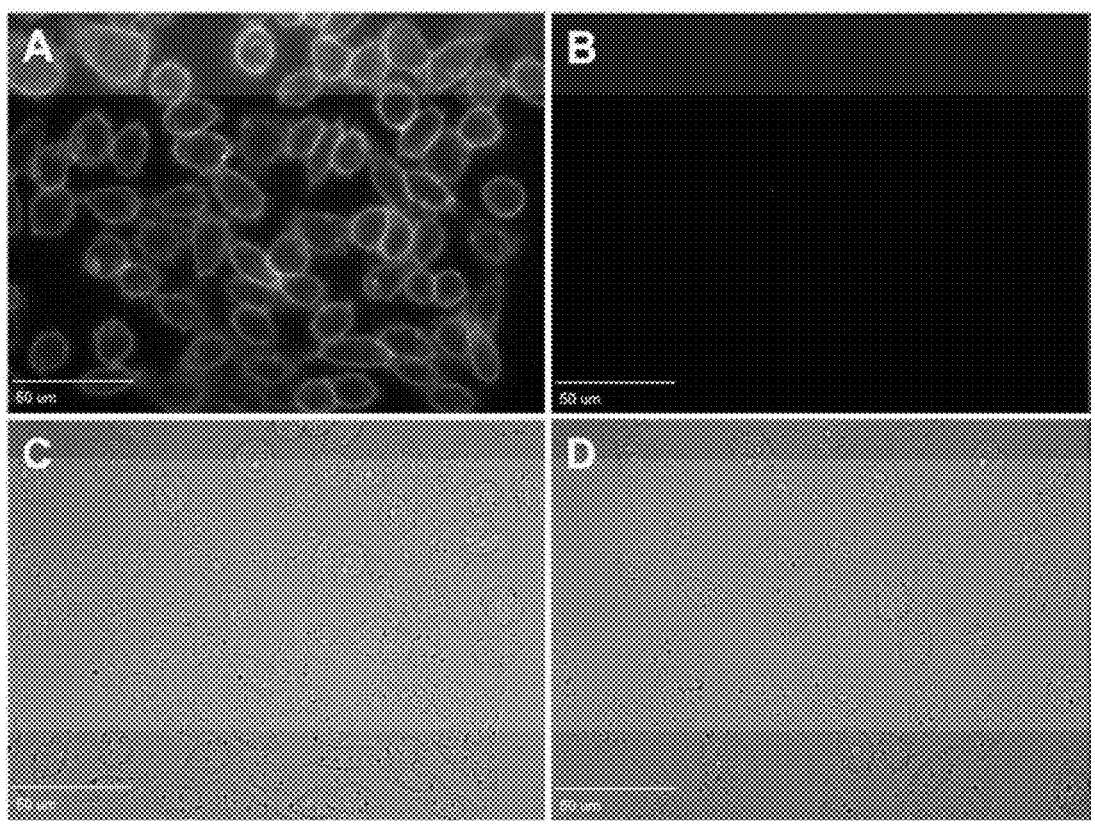
FIG. 13A-13D show images of no-wash CHO cell labeling with 10, according to embodiments of the present disclosure. Labeling was performed for 15 min and quenched with BCS following the above procedure. (A),(C) Fluorescence and brightfield images of cells treated with Ac$_4$ManNAl (B),(D) Fluorescence and brightfield images of cells treated with Ac$_4$ManNAc. Scale bar=50 µm.
Figure 14:
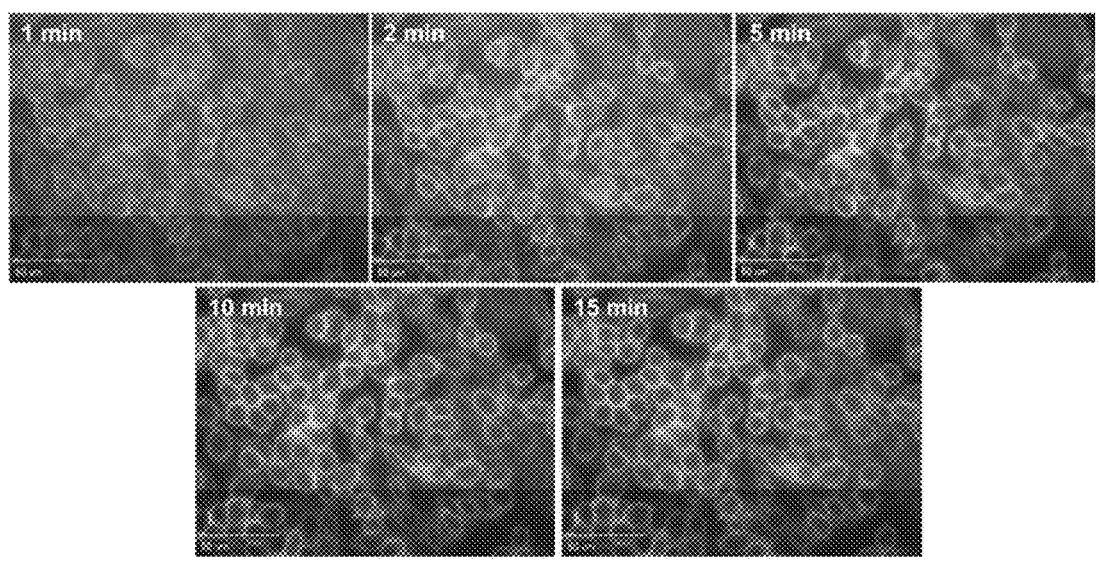
FIG. 14 shows images of real-time CHO K1 cell surface labeling. Ac$_4$ManNAl treated CHO K1 cells were labeled with 10 following the previously described procedure, then immediately taken on for imaging, according to embodiments of the present disclosure. Contrast is enhanced at early time points to show cell-surface labeling. Scale bar=50 µm.

Si-rhodamine 10 was evaluated as a reagent for imaging SiaNAl residues on live cell surfaces. CHO K1 cells were incubated with 50 μM Ac4ManNAl for 3 days, washed, and then incubated with 5 μM 10, 50 μM CuSO4, 300 μM BTTAA, and 1 mM sodium ascorbate. After 15 minutes, without washing away excess probe, robust cell-surface labeling was observed (FIG. 13). Cell-surface glycan labeling was visualized as it occurred in real time (FIG. 14). Background labeling was minimal on control cells treated with N-acetylmannosamine (Ac4ManNAc) (FIG. 13).

When a similar experiment was performed using HEK 293T cells, punctate fluorescence appeared within the cells almost immediately after exposure compound 10 (FIG. 15). It has been previously demonstrated that Si-rhodamines, as lipophilic cations, can localize to the mitochondria. Indeed, such localization of our probe was confirmed by co-staining with Mitotracker Green (FIG. 16). This observation suggests that, while probe 10 has the potentially beneficial property of cell permeability, it may be compromised by unwanted mitochondrial labeling in some eukaryotic cell types.

Figure 6:
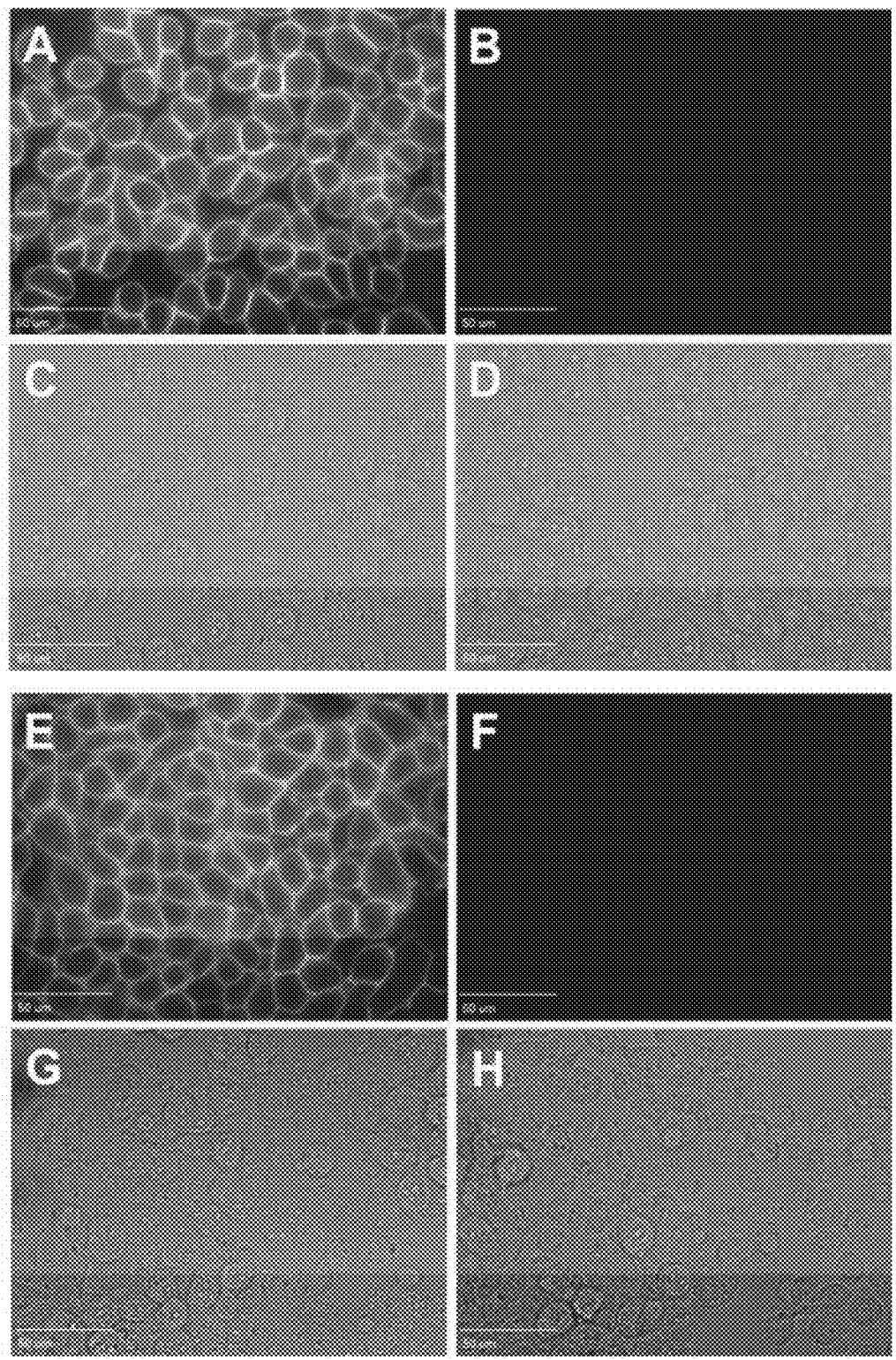
FIG. 6A-6H show images of no-wash mammalian cell surface labeling with bis-sulfated probe 11, according to embodiments of the present disclosure. (A),(C) Fluorescence and brightfield images of CHO K1 cells treated with Ac$_4$ManNAl and labeled with 11. (B),(D) Fluorescence and brightfield images of CHO K1 cells treated with Ac$_4$ManNAc and labeled with 11. (E),(G) Fluorescence and brightfield images of HEK 293T cells treated with Ac$_4$ManNAl and labeled with 11. (F),(H) Fluorescence and brightfield images of HEK 293T cells treated with Ac$_4$ManNAc and labeled with 11. Scale bar=50 µm.
Figure 17:
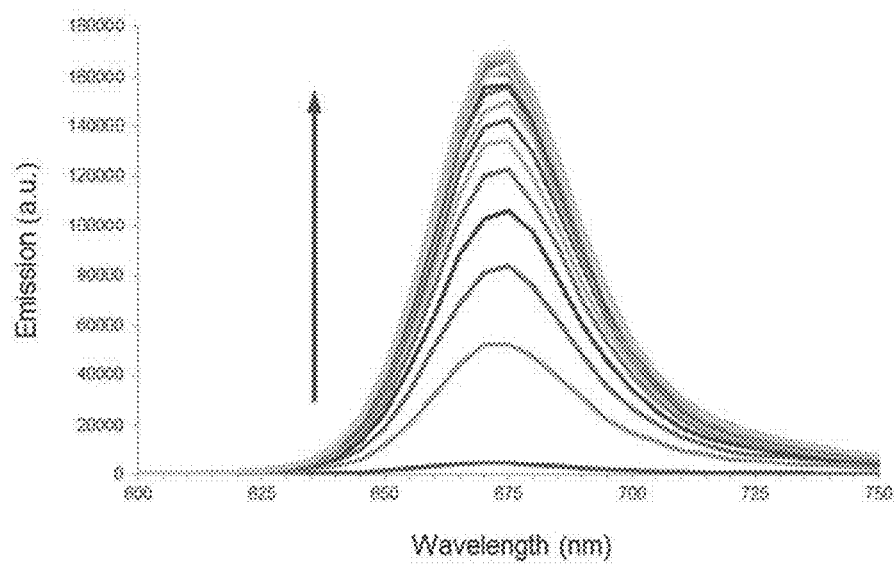
FIG. 17 shows a graph of fluorescence enhancement of 11 under the copper-catalyzed click conditions described above, according to embodiments of the present disclosure. Emission scans were taken every 30 seconds, with excitation at 600 nm.
Figure 18:
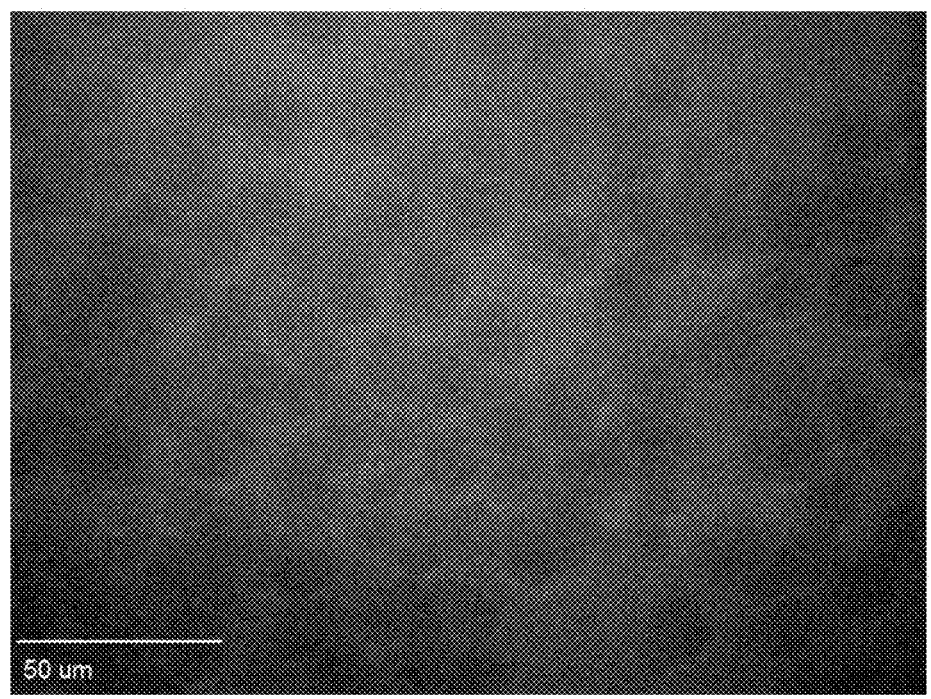
FIG. 18 shows a higher contrast image of $Ac_4ManNAc$-treated cells in FIG. 6F, demonstrating that 11 is not cell permeable, according to embodiments of the present disclosure. Scale bar=50 µm.

To prevent mitochondrial labeling, bis-sulfated probe 11 was synthesized; it was anticipated that the negative charges would limit cell permeability as well as mitochondrial localization (FIG. 5, and Scheme 2). Like its predecessors, compound 11 displayed significant fluorescence enhancement upon triazole formation (FIG. 17). In contrast to compound 10, this bis-sulfated probe gave robust cell-surface labeling under no-wash conditions for both CHO K1 and HEK 293T cells, with no unwanted background or mitochondrial labeling (FIG. 6, and FIG. 18).

Incorporation of Cyclooctyne-Functionalized D-Alanine Analogs into Peptidoglycan Bacterial peptidoglycan (PG) is an emerging target for molecular imaging using bioorthogonal chemistry. As shown below, metabolic labeling with a cyclooctyne D-alanine analog enabled copper-free PG imaging using the NIR fluorogenic probes described above.

Figure 7:
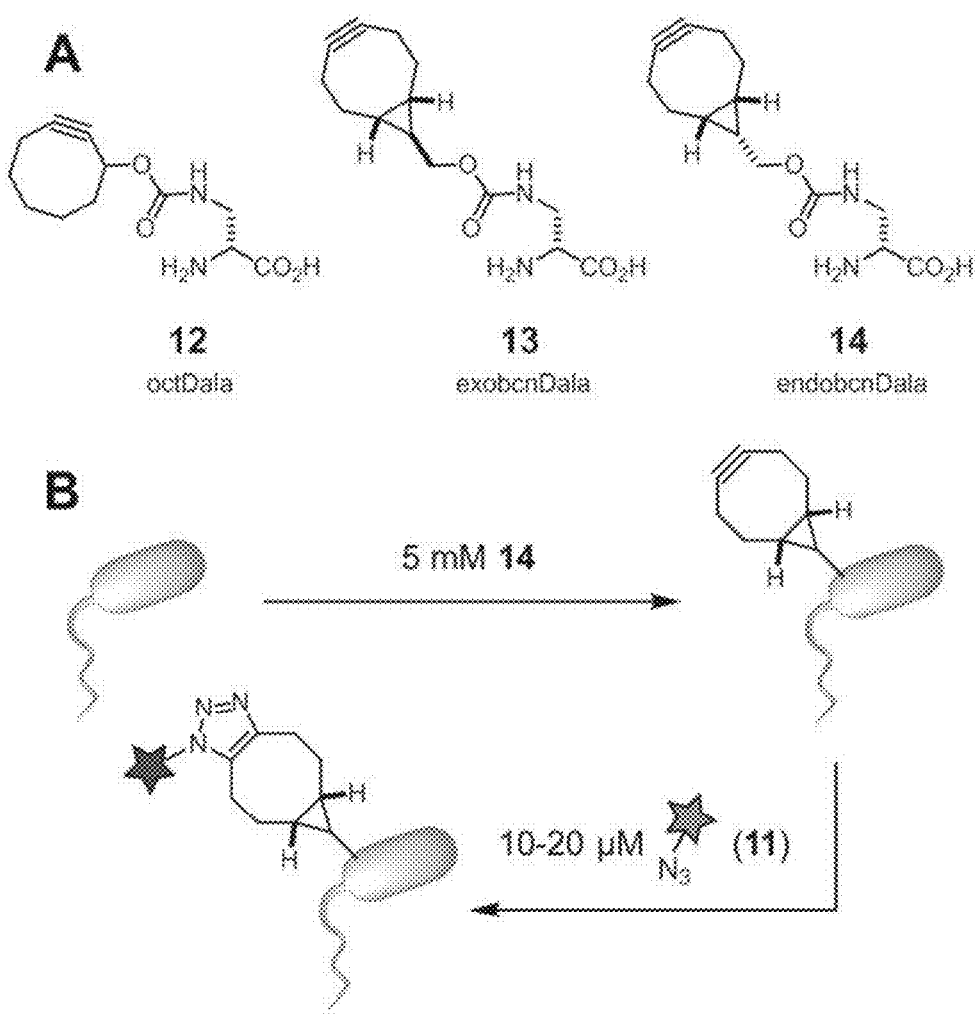
FIG. 7A-7B show structures and a scheme for imaging bacterial PG with cyclooctyne D-alanine analogs and fluorogenic azide probes, according to embodiments of the present disclosure. (A) Structures of cyclooctyne D-amino acids 12 through 14. (B) No-wash peptidoglycan labeling workflow using endobcnDala 14 and bis-sulfated azido Si-rhodamine 11.

Cyclooctyne-functionalized D-alanine analog 12 (oct-Dala), as well as the bicyclononyne (BCN) derivatized stereoisomers 13 (exobcnDala) and 14 (endobcnDala), were synthesized, all in two steps from known compounds (FIG. 7A, and Scheme 3). The minimally substituted cyclooctyne ring of 12 offers the least steric bulk, but is less reactive than the BCN moiety of 13 and 14. Although there are other means of enhancing cyclooctyne reactivity, such as aryl ring fusions, these would impose much additional steric bulk.

Metabolic incorporation of 12-14 into the cell walls of the Gram-positive bacteria *Mycobacterium smegmatis, Corynebacterium glutamicum* and *Listeria monocytogenes* was tested. The bacteria were grown for one doubling time in the presence of 5 mM 12, 13 or 14, washed to remove excess amino acid, and then reacted with 20 µM commercially available azido-PEG3-carboxyrhodamine 110, a reagent previously used to image alkyne-funtionalized D-alanine derivative (alkDala)-labeled PG under copper-catalyzed conditions. The cells were washed to remove excess probe, fixed, and analyzed by flow cytometry and microscopy (FIGS. 19-21). The fluorescence intensities observed correlated with the relative reactivities of the parent cyclooctynes. Cells incubated with 13 and 14 followed by copper-free reaction with azido-PEG3-carboxyrhodamine 110 showed comparable fluorescence intensity to cells metabolically labeled with alkDala followed by copper-catalyzed reaction with the same probe. Thus, cyclooctyne D-alanine analogs 13 and 14 enable PG imaging with the same sensitivity as the earlier methods, but without the need for a cytotoxic copper catalyst.

While the observed fluorescence appeared to concentrate at the bacterial cell walls (FIGS. 19-21), consistent with incorporation of cyclooctyne D-alanine analogs into PG, additional evidence that these unnatural amino acids access the same metabolic pathways as natural D-alanine was sought. A competition experiment was performed, showing that excess D-alanine decreases the fluorescence intensity of *L. monocytogenes* incubated with 12, 13 or 14 (FIG. 22). Additionally, it was found that *L. monocytogenes* lacking the PBP5 carboxypeptidase, which trims the terminal D-alanine residues from the pentapeptide PG crosslink, shows enhanced labeling compared to wild type bacteria (FIG. 23). The labeling enhancement in the absence of PBP5 is comparable for both the relatively small alkDala and our bulkier cyclooctyne amino acids, suggesting that this carboxypeptidase is tolerant of larger, unnatural D-amino acids.

Copper-Free Peptidoglycan Imaging with Fluorogenic NIR Azide Probes

Figure 8:
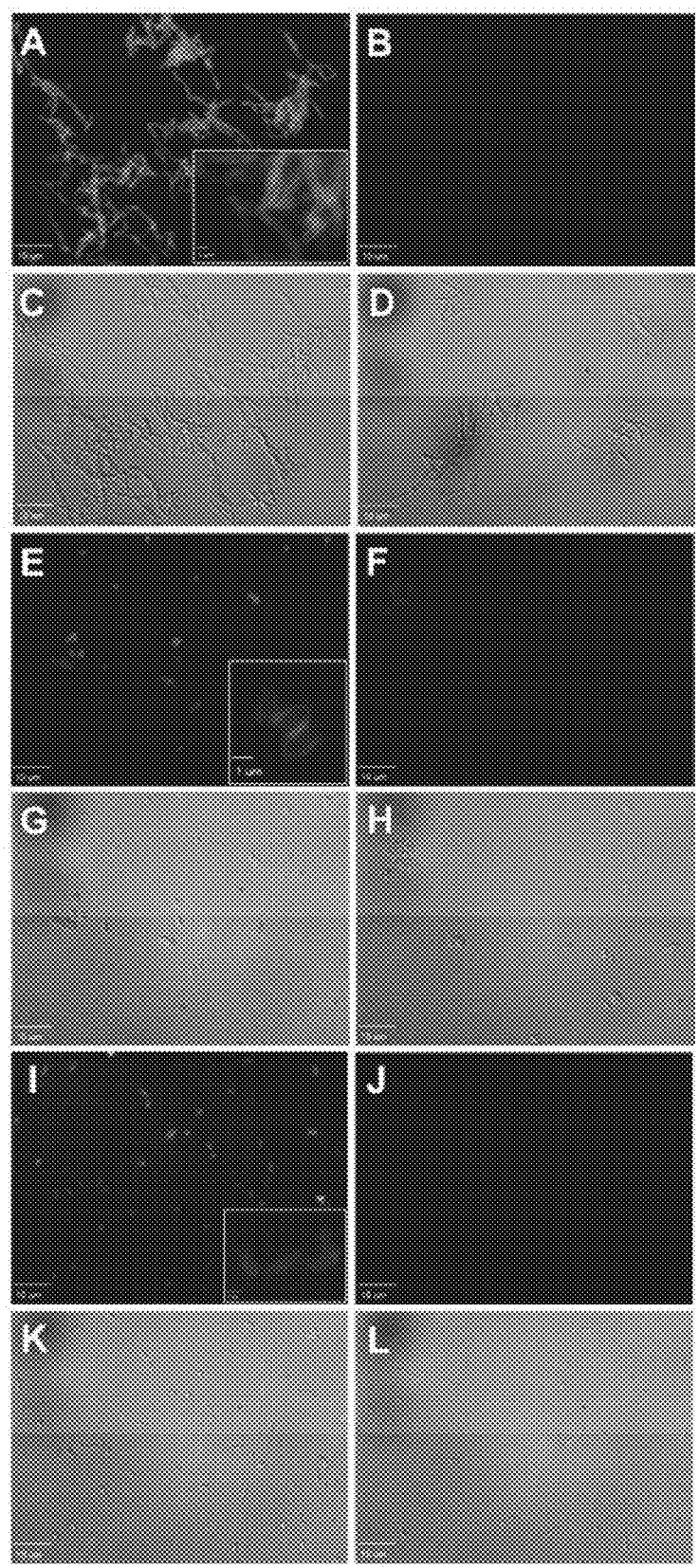
FIG. 8A-8L show images of no-wash bacterial PG labeling. Bacteria were treated with 5 mM endobcnDala 14 or D-alanine, then reacted with 10 or 20 µM bis-sulfated probe 11 for 1 h, according to embodiments of the present disclosure. (A)-(D) Fluorescence and brightfield images of M. smegmatis treated with 14 or D-alanine and labeled with 10 µM 11. (E)-(H) Fluorescence and brightfield images of C. glutamicum treated under the same conditions. (I)-(L) Fluorescence and brightfield images of L. monocytogenes pbp::tn treated under the same conditions, but labeled with 20 µM 11. Scale bar=10 Insets in (A), (E), (I) show cells enlarged to highlight cell surface labeling. Scale bar=1 µm.

Finally, the bacteria were imaged using the NIR fluorogenic azide probes. It was confirmed that azido Si-rhodamines 9, 10, and 11 would undergo an enhancement in fluorescence upon reaction with cyclooctynes. These probes were incubated with endo-bicyclononynol in vitro to generate triazole products (FIG. 24A). Their fluorescence enhancement was similar to that observed in the copper-catalyzed click reaction with linear alkynes, showing that the fluorogenic character of probes 9-11 is not dependent on the substitution pattern of the triazole (FIG. 24B). All three bacterial strains were incubated with endobcnDala 14 as before, but after washing away excess amino acid, the bacteria were incubated with 10 or 20 µM 11 for 1 hour and directly imaged without washing away excess probe (FIG. 7B). Clear fluorescence signal over background was observed in all cases, demonstrating the suitability of cyclooctyne-functionalized D-amino acids and fluorogenic azides for imaging PG on live cells (FIG. 8). Notably, cyclooctyne-dependent labeling was observable even with the use of 500 µM endobcnDala 14, showing that the sensitivity of our method can be comparable to other D-amino acid labeling strategies (FIG. 25). While the biosynthetic machinery can tolerate fluorophore-conjugated D-amino acids, allowing one-step PG imaging versus our two-step metabolic/chemical labeling approach, chemical reporter groups are much smaller than long-wavelength fluorophores and therefore minimize possible biological perturbations. The Gram-negative organism *Escherichia coli* metabolized compound 14 similarly to the Gram-positive bacteria, but was not efficiently labeled with dye 11 (FIG. 26). It is hypothesized that the presence of an outer membrane (though apparently not a mycobacterial "mycomembrane", FIG. 8A-D) limits access of compound 11 to PG. By contrast, smaller dyes were able to access both terminal alkynes and cyclooctynes in metabolically labeled *E. coli* PG (FIG. 27).

DFT Calculations

Aryl $E_{HOMO}$s were calculated by first performing a conformational search in MacroModel (Schrödinger) to identify low energy conformers. Low energy conformers were further optimized using Jaguar (Schrödinger) at the B3LYP/6-31G (d) level of theory. See FIG. 9. The reported $E_{HOMO}$ corresponds to the lowest energy conformer after DFT calculations. No significant differences in energies were observed by considering sets of conformers or by optimizing the geometry with the xanthene moiety present. Calculations were performed at the UC Berkeley College of Chemistry Molecular Graphics and Computation Facility.

Measuring Fluorescence Quantum Yields

Fluorescence quantum yields were measured by creating 2 mM stocks of dyes in MeOH. The dyes were then diluted to 20 µM in PBS, then further diluted in PBS to various final concentrations. The absorbance and emission spectra of five different concentrations of dye were measured while keeping maximum absorbance under 0.2. Solutions of probe were excited at 600 nm, and emission was integrated from 600 to 800 nm. Plotting integrated emission vs. absorbance at 600 nm yielded a line, whose slope corresponds to the fluorescence quantum yield. Absolute quantum yields were determined by comparison with the slope of the line measured for cresyl violet in MeOH ($\Phi_{fl}$=0.54). The reported quantum yields are the average of three sets of measurements. Absorbance spectra were recorded on a Varian Cary 50 UV-Visible spectrophotometer. Fluorescence spectra were recorded on a Photon Technology International Quanta Master 4 L-format scanning spectrofluorometer equipped with an LPS-220B 75-W xenon lamp and power supply, A-1010B lamp housing with an integrated igniter, switchable 814 photon counting/analog photomultiplier detection unit, and MD5020 motor driver. Measurements were made in 1 cm×0.4 cm quartz cuvettes with a total sample volume of 1 mL.

Monitoring Absorbance/Fluorescence During Copper-Catalyzed Click Reactions

To a 1 cm×0.4 cm quartz cuvette was added 944 µL PBS. Next, 2 µL 50 mM BTTAA in PBS and 1 µL 50 mM CuSO$_4$ in H$_2$O were added and the solution mixed with a pipette. Next, 50 µL freshly prepared 100 mM sodium ascorbate in PBS was added and the solution mixed again. Then, 2 µL 1 mM azido Si-rhodamine in 4:1 PBS/MeOH was added and the solution mixed. The emission spectra were recorded at this time (t=0 s). Finally, 1 µL 100 mM alkyne in dimethylsulfoxide (DMSO) was added and the solution vigorously mixed and monitored every 30 s for 10 min. Final concentrations for all reagents are 2 µM azido Si-rhodamine, 100 µM alkyne, 100 µM BTTAA, 50 µM CuSO$_4$, and 5 mM sodium ascorbate with a total volume of 1 mL. Fluorescence spectra were recorded on a Photon Technology International Quanta Master 4 L-format scanning spectrofluorometer equipped with an LPS-220B 75-W xenon lamp and power supply, A-1010B lamp housing with an integrated igniter, switchable 814 photon counting/analog photomultiplier detection unit, and MD5020 motor driver. Absorption spectra were recorded on a Varian Cary 50 UV-Visible spectrophotometer with 1.5 µM dye. See FIGS. 10-12.

Fluorescence Microscopy

For mammalian cells, microscopy was performed using a Zeiss AxioVert 200M inverted microscope using a Plan-Neofluar 40×/ 0.75 or 63×/0.75 objective. For bacterial cells, microscopy was performed using a 100×/1.3 objective. A 175 W xenon lamp housed in a Sutter DG4 illuminator linked to the microscope by an optical fiber assured shuttering and illumination. Exposure time was 1000 ms using the Cy5 filter for labeling with azido Si-rhodamines and 1000 ms using the FITC filter for labeling with azido-PEG$_3$-carboxyrhodamine 110 or azido-carboxyrhodamine 110. Images were acquired and processed using SlideBook 5.0, and are shown as a single z-plane. Images acquired with the Cy5 filter are false-colored white or pink, while images acquired with the FITC filter are false-colored green.

No-Wash Mammalian Cell Labeling

Cells were grown in 8-well Lab-Tek Chambered Coverglass systems in media (HAM-F12 for CHO K1 cells, DMEM for HEK 293T cells) containing 10% fetal bovine serum, penicillin/streptomycin, and either 50 µM Ac$_4$ManNAl or Ac$_4$ManNAc for 3 d at 37° C., as described previously. The cells were then washed with 3×300 µL PBS, then incubated with 100 µL freshly prepared click solution. Click solution comprised of 50 µM CuSO$_4$, 300 µM BTTAA, 2.5 mM sodium ascorbate, and 5 µM azido Si-rhodamine. This was prepared by first adding 0.5 µL 50 mM CuSO$_4$ in H$_2$O and 3 µL 50 mM BTTAA in H$_2$O to 481.5 µL PBS. Next, 12.5 µL freshly prepared 100 mM sodium ascorbate in PBS was added. Finally, 2.5 µL 1 mM azido Si-rhodamine in 4:1 PBS/MeOH was added. After 15 min, the reactions were quenched with the addition of 1 µL of 100 mM bathocuproine disulfonate (BCS) in H$_2$O (final concentration 1 mM). No changes in fluorescence were observed before or after the addition of BCS. For real-time imaging, images were acquired as the labeling progressed without quenching the reaction. See FIGS. 13-15.

Mitochondrial Co-Staining Experiments

HEK 293T cells were grown in a LabTek 8-well chambered glass slide in DMEM containing fetal bovine serum, penicillin/streptomycin for 3 d at 37° C. The cells were then incubated with 100 nM MitoTracker Green FM and 1 µg/mL Hoechst 33342 in fresh media for 30 min at 37° C., then media removed and the cells incubated with 100 µL PBS containing 5 µM 10. The cells were then directly imaged. See FIG. 16.

Peptidoglycan Labeling with Unnatural D-Amino Acids

Bacteria were grown to an optical density (OD) of 0.4 in their respective media (7H9 for *M. smegmatis*, LB for *C. glutamicum*, BHI for *L. monocytogenes*) at 37° C. (*M. smegmatis* and *L. monocytogenes*) or 30° C. (*C. glutamicum*). Then, 5 mM D-amino acid was added (from a 1 M stock in H$_2$O, 1 eq. NaOH was added to help solubilize compounds 12, 13, and 14) and the cells grown for one doubling time. The bacteria were then added to a 96-well V-bottom plate at 200 µL/well and pelleted by centrifugation at 3500 rpm for 3 min. The supernatant was removed and the cells resuspended in 200 µL PBS and pelleted again. This wash process was repeated twice more. The cells were then incubated with 100 µL of 20 µM azido-PEG$_3$-carboxyrhodamine 110 (Click Chemistry Tools) in PBS (made by diluting a 1 mM stock in 9:1 PBS/DMSO) and placed in a 37° C. shaker for 1 h. Alternatively, for alkDala, labeling was performed by incubation with 100 µL of 20 µM azido-PEG$_3$-carboxyrhodamine 110, 128 µM TBTA, 1 mM CuSO$_4$, and 1.2 mM sodium ascorbate in PBS in a 37° C. shaker for 1 h. The cells were washed three times, then fixed with 4% paraformaldehyde for 10 min at rt. The cells were washed another three times, then studied by flow cytometry and microscopy. For flow cytometry studies with *M. smegmatis*, the cells were washed with PBS containing 0.5 mg/mL BSA and 0.1% v/v TWEEN 20 to minimize clumping. See FIGS. 19-23.

Reaction of Azido Si-Rhodamines with Endo-Bicyclononynol

25 µL of 1 mM azido Si-rhodamine in 4:1 PBS/MeOH was mixed with 0.5 µL of DMSO or 0.5 µL 100 mM endo-bicyclononynol (2 equiv.) in DMSO. The solutions were covered with foil and gently shaken overnight (18 h). 2.04 µL of each solution was diluted to a final volume of 1 mL in PBS for fluorescence measurements. See FIG. 24.

No-Wash Peptidoglycan Labeling with Compound 11

The bacteria were incubated with either endobcnDala or Dala and washed as described above. The cells were then taken up in 100 µL of 10 to 20 µM 11 in PBS (made by dilution of a 1 mM stock of 11 in 4:1 PBS/MeOH. 5 µL of cells were immediately plated on a glass slide, covered by coverslip, and imaged after 1 h. See FIGS. 25-27.

Synthetic Schemes
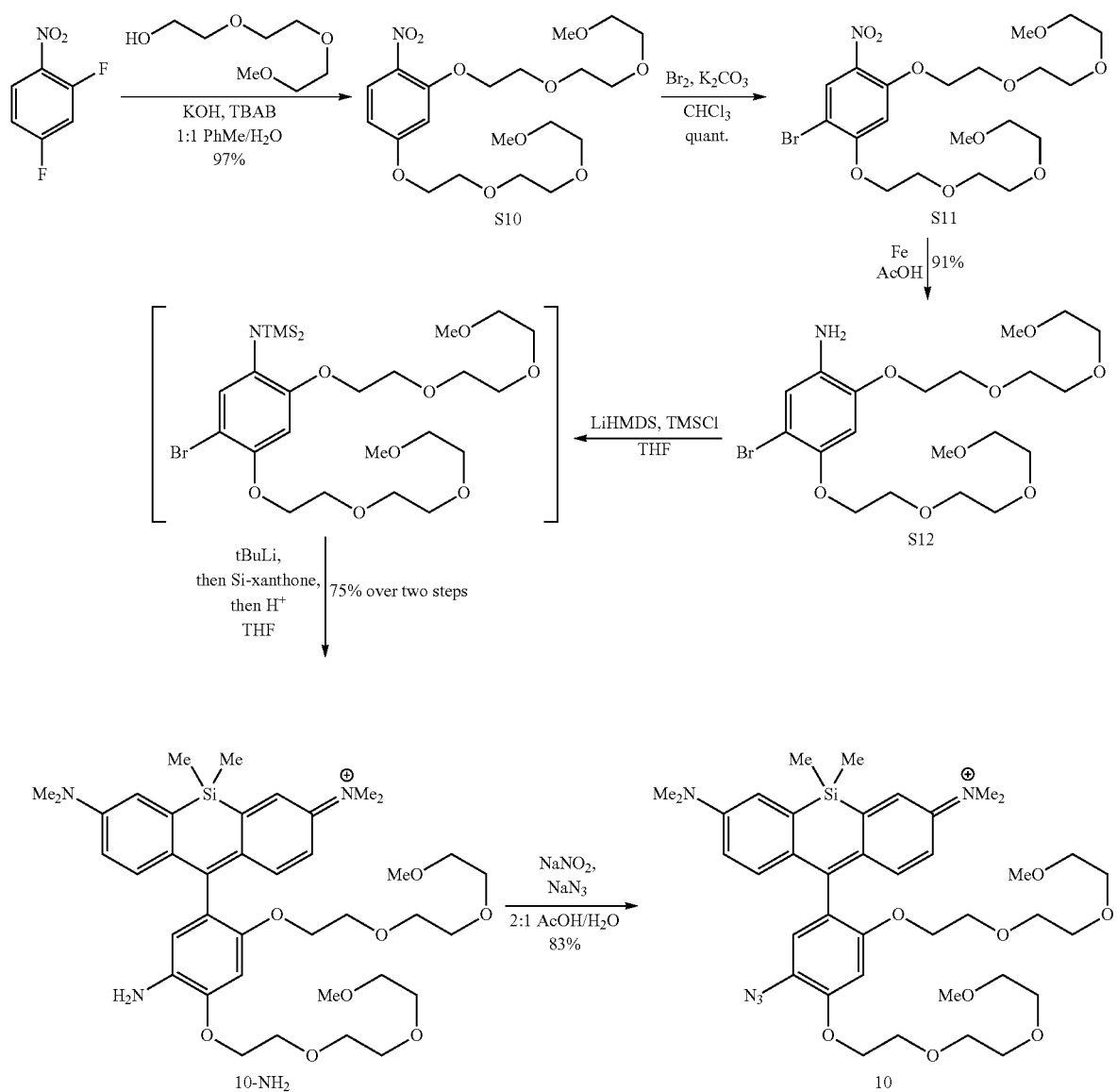
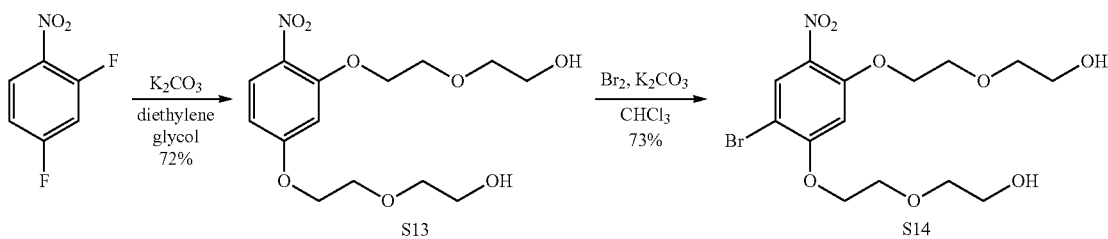

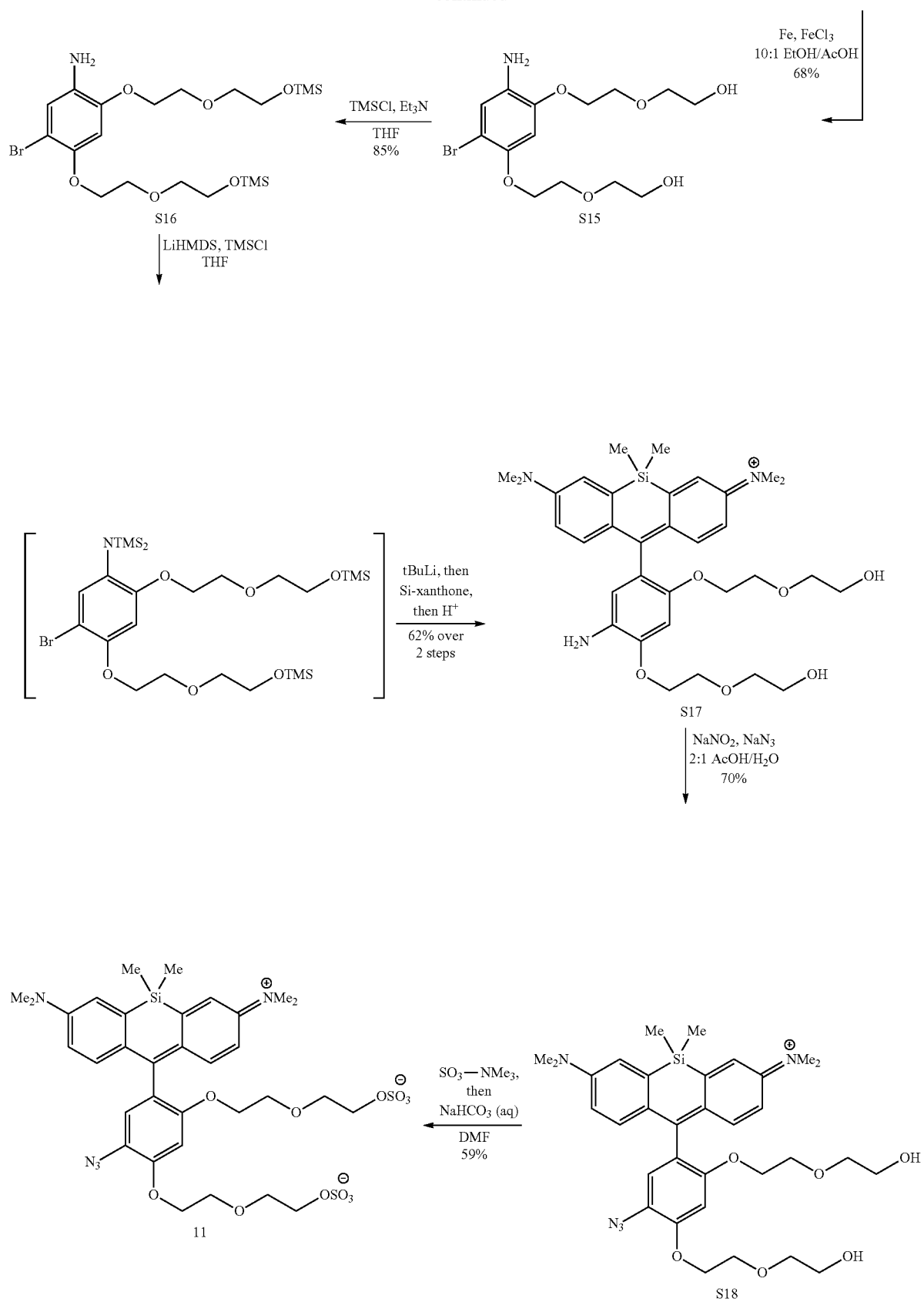

Scheme 3
Synthesis of cyclooctyne-functionalized D-alanine analogs 12 to 14

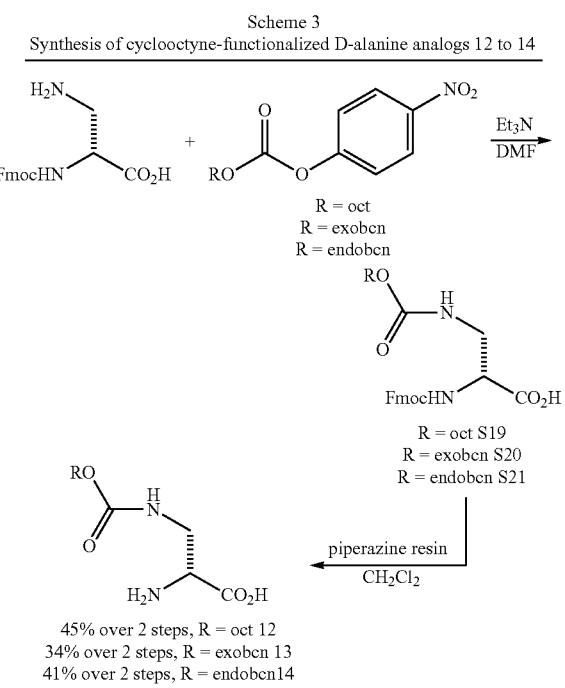

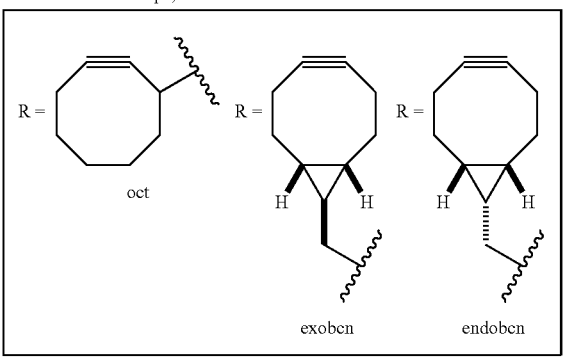

Synthetic Procedures

All chemical reagents obtained from commercial suppliers were used without further purification. Anhydrous dichloromethane, tetrahydrofuran and acetonitrile were passed through an activated alumina column prior to use. Anhydrous DMF was used as purchased. Water was double distilled prior to use. Ac$_4$ManNAl[1] and BTTAA[2] were prepared according to literature procedures.

Flash chromatography was performed using Silicycle SiliaFlash P60 silica gel. Analytical thin layer chromatography was performed using glass-backed Analtech Uniplate silica gel plates containing a fluorescent indicator. Reversed-phase HPLC was performed on a Varian Pro Star system with a Varian UV-Vis detector model 345 (210, 254 nm) on a Dynamax Microsorb C-18 preparative column (21.4×250 mm) at a flow rate of 20 mL/min or on a Dynamax Microsorb C-18 semi-preparative column (10.0×250 mm) at a flow rate of 4 mL/min.

NMR spectra were obtained on Bruker AVQ-400, AVB-400, DRX-500, AV-500, or AV-600 spectrometers at ambient temperature at the UC Berkeley College of Chemistry NMR Facility. $^1$H NMR shifts are calibrated to residual undeuterated solvent: δ 7.26 for CHCl$_3$, 2.50 for d$_5$-DMSO, 4.79 for HDO, and 3.31 for CHD$_2$OD. $^{13}$C NMR shifts are calibrated to solvent peaks: δ 77.16 for CDCl$_3$, 39.52 for d$_6$-DMSO, and 49.00 for CD$_3$OD. High resolution mass spectrometry was performed at the UC Berkeley Mass Spectrometry Laboratory.

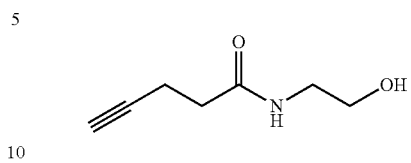

0.245 g (2.50 mmol) 4-pentynoic acid, a white crystalline solid, was dissolved in 25 mL dry CH$_2$Cl$_2$ in a flame-dried flask. Then, 0.382 g HOBt hydrate (2.50 mmol, 1 equiv.), an off white powder, was added. The cloudy white suspension was cooled to 0° C., then 0.387 mL (0.316 g, 2.50 mmol, 1 equiv.) diisopropylcarbodiimide, a clear liquid, was added. The solution was warmed to rt and stirred vigorously for 10 min, then 0.21 mL (0.214 g, 3.50 mmol, 1.4 equiv.) ethanolamine, a viscous yellow liquid, was added, immediately turning the slightly cloudy white solution to a thick white slurry. The reaction was stirred at rt for 8 h, then filtered to remove the HOBt. The clear filtrate was concentrated to yield an off-white residue. The residue was purified by flash chromatography using 20:1 to 10:1 CHCl$_3$/MeOH, yielding alkyne A (0.323 g, 2.29 mmol, 92%) as a clear oil that solidified to a white solid upon storage at −20° C. Spectral data were identical to reported values.[3]

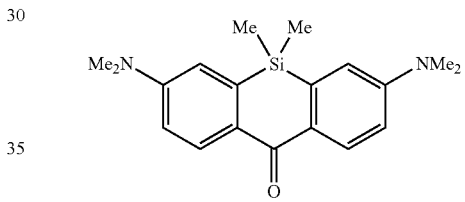

2.02 g (4.90 mmol) 4,4'-methylenebis(3-bromo-N,N-dimethylaniline)[3], a light pink solid, was added to a flame-dried flask and azeotropically dried with benzene. The solid was dissolved in 48 mL dry THF in a flame-dried flask. The clear solution was cooled to −78° C. Next, 10.7 mL sec-butyllithium (0.96 M in cyclohexane, 10.3 mmol, 2.1 equiv.), was added slowly directly into the solution. The now yellow solution was stirred at −78° C. for 30 min. Next, 0.71 mL (0.759 g, 5.88 mmol, 1.2 equiv.) dimethyldichlorosilane, a clear liquid, in 24 mL dry THF was added dropwise down the side of the flask. Upon completion of addition, the solution was warmed to rt and stirred for 3 h under N$_2$. The solution was quenched by the addition of 6 mL 2M HCl, and the cloudy solution then poured into 100 mL sat. NaHCO$_3$ and extracted with 3×150 mL CH$_2$Cl$_2$. The combined organic layers were dried over MgSO$_4$ and concentrated, yielding intermediate N3,N3,N7,N7,5,5-hexamethyl-5,10-dihydrodibenzo[b,e]siline-3,7-diamine as an air-sensitive light blue-green oil. R$_f$=0.3 (10:1 hex/EtOAc, UV/I$_2$).

The light blue-green oil was dissolved in 35 mL CH$_2$Cl$_2$ and cooled to 0° C. Next, 2.32 g (10.86 mmol, 3 equiv.) potassium permanganate, a grey solid, was dissolved in ~20 mL hot water and 4.9 mL 1M KOH (4.90 mmol, 1 equiv.), 0.333 g (0.980 mmol, 0.2 equiv.) tetrabutylammonium bisulfate, a white solid, and cold water were added to give a final volume of 30 mL. The purple solution was added to the reaction flask, turning the solution to a muddy brown. The flask containing the reagents was washed with another 20 mL CH$_2$Cl$_2$ and 20 mL H$_2$O. The cloudy brown solution was stirred for 30 min, after which TLC indicated consumption of starting material, then the reaction was quenched by the addition of 10 mL AcOH. (Letting the reaction go for too long results in the formation of significant amounts of a difficult-to-separate byproduct with a slightly lower $R_f$ than the desired Si-xanthone). The solution was cooled to 0° C., then 3.8 g $Na_2SO_3$ was carefully added, turning the brown solution an olive-green. The reaction was diluted with 150 mL 50% brine and extracted with 5×100 mL $CH_2Cl_2$, dried over $MgSO_4$, and concentrated, yielding a blue-green solid. The solid was purified by flash chromatography with 7:1 hexanes/EtOAc to yield Si-xanthone (0.706 g, 2.18 mmol, 44%) as a golden yellow solid. Spectral data were identical to reported values.

General Procedure for the Synthesis of Bis-Trimethylsilyl-Protected Bromoanilines:

Bromoaniline was dissolved in dry THF (concentration of 0.30 M) in a flame-dried flask and cooled to −78° C. To the solution was added 2.1 equiv. freshly prepared 0.60 M LiHMDS in THF, also cooled to −78° C., dropwise via cannula. After addition, the solution was stirred for 10 min at −78° C., warmed to rt for 5 min, then cooled back to −78° C. Finally, 2.1 equiv. trimethylsilyl chloride was added dropwise and the solution warmed to rt and stirred overnight (16 h). The now cloudy solution was concentrated and taken up in hexanes and filtered. The filtrate was concentrated to afford bis-TMS-protected aniline, generally contaminated with small amounts of tris-trimethylsilylamine, which was used directly in the next step without further purification.

General Procedure for the Synthesis of Amino Si-Rhodamines

Bis-TMS-protected aniline was dissolved in dry THF in a flame-dried flask to a final concentration of 0.2 M. The solution was cooled to −78° C. To the solution was then added dropwise 2 equiv. tBuLi (freshly titrated, from a ~1.6 M solution in pentanes). After 30 minutes, 0.48 equiv. Si-xanthone, a yellow solid, was suspended in 3 mL dry THF (concentration of 0.1 M) and added in one portion. The solution was immediately warmed to rt and stirred for 1 h. The reaction was then quenched by the slow addition of 3 equiv. HCl (from a 2 M aqueous solution), turning the solution a deep blue color. The blue solution was quickly poured into 10% sat. $NaHCO_3$ and extracted 5 times with $CH_2Cl_2$, dried over $MgSO_4$, and concentrated to yield a blue solid. The solid was purified by flash chromatography with $CHCl_3$ to 20:1 $CHCl_3$/MeOH to 7:1 $CHCl_3$/MeOH to yield the product as a blue solid. For photophysical measurements, the solid was further purified by reverse-phase HPLC using a 20-100% MeCN/$H_2O$+0.1% TFA gradient.

General Procedure for the Synthesis of Azido Si-Rhodamines

Amino Si-rhodamine, a blue solid, was dissolved in a 2:1 AcOH/$H_2O$ mixture to a final concentration of 0.025 M. The blue solution was cooled to 0° C. Next, 1.5 eq. sodium nitrite, a white powder, was added. The solution was stirred for 5 min at 0° C., during which the color lightened slightly. Next, 2 eq. sodium azide, a white solid, was added. Bubbling was observed. The solution was stirred for 1 h at 0° C. and 1 h at rt, then concentrated in vacuo. The remaining blue residue was purified with flash chromatography using $CHCl_3$ to 20:1 $CHCl_3$/MeOH to 7:1 $CHCl_3$/MeOH to yield the product as a blue solid. The product was further taken up in $CHCl_3$ and washed 3 times with 0.1% TFA in $H_2O$ to yield the product as the TFA salt. For photophysical measurements and biological experiments, the solid was further purified by reverse-phase HPLC using a 20-100% MeCN/$H_2O$+0.1% TFA gradient.

General Procedure for the Synthesis of Triazolyl Si-Rhodamines

Azido Si-rhodamine, a blue solid, was dissolved in MeOH to a final concentration of 0.02 M. The blue solution was placed under a $N_2$ atmosphere, then 5 equiv. alkyne A, a white solid, was added. Next, 0.5 equiv. Cu(MeCN)$_4$PF$_6$, a white powder, was added, followed by 0.01 equiv. TBTA (added from a 10 mM solution in MeOH). The blue solution was stirred for 15 h, after which consumption of starting material was confirmed by LC-MS. The solution was concentrated and the blue residue purified by reverse-phase HPLC using a 20-100% MeCN/$H_2O$+0.1% TFA gradient to yield the product as a blue solid.

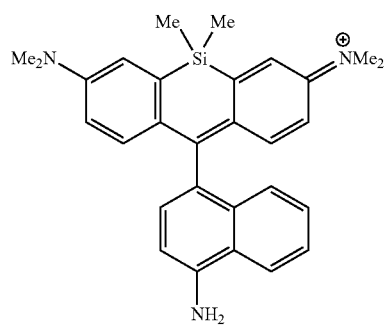

0.111 g (0.500 mmol) of 1-amino-4-bromonaphthalene was converted to the bis-trimethylsilyl-protected-aminobromonaphthalene (0.173 g, 0.472 mmol, 94%), a wet pink-grey solid, via the general procedure.

0.120 g (0.328 mmol) of this intermediate was converted to 1-NH$_2$ (64.2 mg, 0.132 mmol, 80% based off Si-xanthone), a blue solid, via the general procedure.

$^1$H NMR (500 MHz, CDCl$_3$): δ 0.04 (s, 3H), 0.06 (s, 3H), 3.36 (s, 12H), 4.72 (brs, 2H), 6.48 (dd, 2H, J=9.6 Hz, 2.9 Hz), 6.97 (d, 1H, J=7.6 Hz), 7.09 (d, 1H, J=7.7 Hz), 7.14 (d, 2H, J=9.6 Hz), 7.20 (d, 2H, J=2.9 Hz), 7.27-7.35 (m, 2H), 7.41-7.49 (m, 1H), 7.97 (d, 1H, J=8.5 Hz); $^{13}$C NMR (151 MHz, CDCl$_3$): δ −0.64, −0.53, 41.12, 108.26, 113.70, 120.38, 1212.84, 122.76, 125.10, 125.49, 126.50, 126.98, 128.41, 129.18, 133.26, 142.80, 144.50, 148.14, 153.98, 171.50; HRMS (ESI): Calculated for C$_{29}$H$_{32}$N$_3$Si [M−Cl]$^+$ 450.2360. found 450.2352.

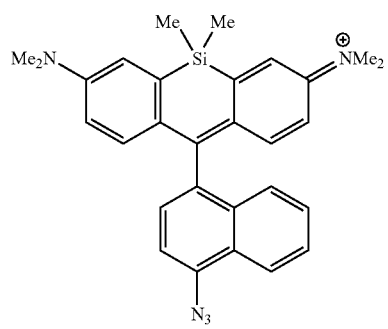

47.1 mg (0.0971 mmol) 1-NH$_2$ was converted to 1-N$_3$ (34.5 mg, 0.0585 mmol, 60%), a blue solid, via the general procedure.

$^1$H NMR (600 MHz, CDCl$_3$): δ 0.63 (s, 3H), 0.66 (s, 3H), 3.32 (s, 12H), 6.47 (dd, 2H, J=9.6 Hz, 2.6 Hz), 6.98 (d, 2H, J=9.6 Hz), 7.18 (d, 2H, J=2.7 Hz), 7.47-7.30 (m, 4H), 7.52

(ddd, 1H, J=8.3 Hz, 6.6 Hz, 1.3 Hz), 8.22 (d, 1H, J=8.5 Hz); $^{13}$C NMR (100 MHz, CDCl$_3$): δ −0.82, −0.80, 40.97, 113.08, 114.03, 120.90, 123.14, 126.07, 126.10, 126.99, 127.05, 128.48, 128.58, 133.03, 133.36, 137.93, 142.19, 148.50, 154.22, 168.31; HRMS (ESI): Calculated for C$_{29}$H$_{30}$N$_5$Si [M−TFA]$^+$ 476.2265. found 476.2256.

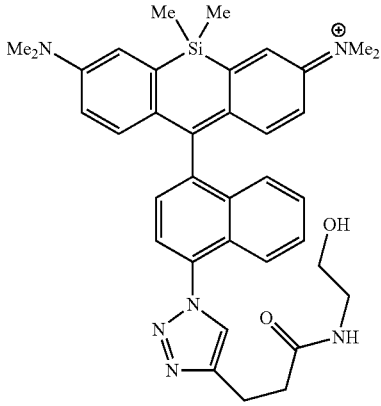

5.9 mg (0.010 mmol) of 1-N$_3$ was converted to 1-triazole (6.3 mg, 0.0086 mmol, 86%), a blue solid, via the general procedure.

HRMS (ESI): Calculated for C$_{36}$H$_{41}$N$_6$O$_2$Si [M−TFA]$^+$ 617.3055. found 617.3048.

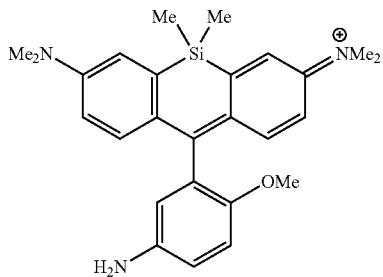

0.202 g (1.00 mmol) 3-bromo-4-methoxyaniline was converted to bis-trimethylsilyl-protected bromoaniline (0.340 g, 0.985 mmol, 98%), a brown oil, via the general procedure.

69.1 mg (0.200 mmol) of this intermediate was converted to 2-NH$_2$ (26.0 mg, 0.056 mmol, 56% based off Si-xanthone), a blue solid, via the general procedure.

$^1$H NMR (400 MHz, CD$_3$OD): δ 0.58 (s, 3H), 0.62 (s, 3H), 3.35 (s, 12H), 3.76 (s, 3H), 6.78 (dd, 2H, J=9.6 Hz, 2.8 Hz), 7.12 (d, 2H, J=9.6 Hz), 7.16 (d, 1H, J=2.7 Hz), 7.32-7.40 (m, 3H), 7.60 (dd, 1H, J=8.9 Hz, 2.8 Hz); $^{13}$C NMR (125 MHz, CDCl$_3$): δ −0.81, −0.64, 41.11, 56.53, 112.82, 113.82, 117.08, 117.49, 120.32, 128.11, 128.15, 140.34, 142.31, 148.23, 149.39, 154.12, 169.17; HRMS (ESI): Calculated for C$_{26}$H$_{32}$N$_3$OSi [M−Cl]$^+$ 430.23092. found 430.23010.

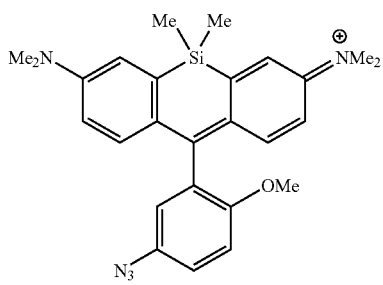

42.3 mg (0.0908 mmol) of 2-NH$_2$ was converted to 2-N$_3$ (30.7 mg, 0.0539 mmol, 59%), a blue solid, via the general procedure.

$^1$H NMR (400 MHz, CDCl$_3$): δ 0.57 (s, 3H), 0.59 (s, 3H), 3.35 (s, 12H), 3.69 (s, 3H), 6.65 (dd, 2H, J=9.6 Hz, 2.8 Hz); 6.74 (d, 1H, J=2.8 Hz); 7.06 (d, 1H, J=8.9 Hz); 7.14 (d, 2H, J=9.6 Hz); 7.14 (d, 2H, J=2.8 Hz), 7.17 (dd, 1H, J=2.8 Hz, 8.9 Hz); $^{13}$C NMR (125 MHz, CDCl$_3$): δ −0.98, −0.72, 40.98, 56.36, 112.65, 114.11, 120.73, 120.88, 120.93, 127.83, 129.06, 132.69, 141.65, 148.45, 154.06, 154.26, 166.39; HRMS (ESI): Calculated for C$_{26}$H$_{30}$N$_5$OSi [M−TFA]$^+$ 456.2214. found 456.2211.

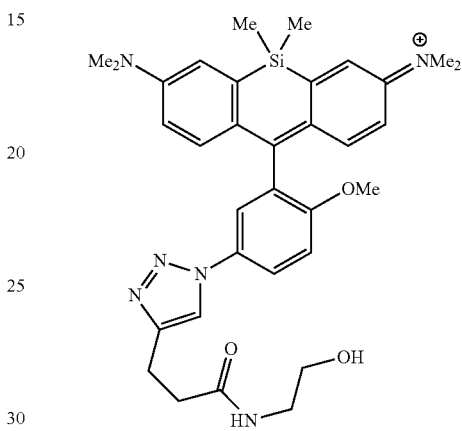

5.7 mg (0.010 mmol) of 2-N$_3$ was converted to 2-triazole (2.5 mg, 0.0035 mmol, 35%), a blue solid, via the general procedure.

HRMS (ESI): Calculated for C$_{33}$H$_{41}$N$_6$O$_3$Si [M−TFA]$^+$ 597.3004. found 597.2991.

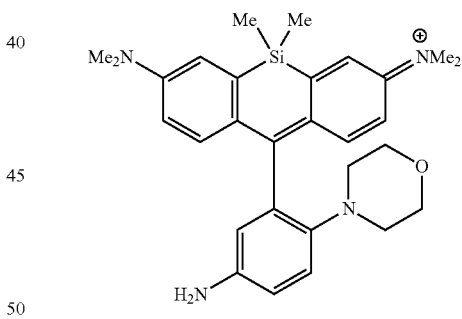

0.386 g (1.50 mmol) 3-bromo-4-morpholinoaniline, a light yellow solid, was converted to bis-trimethylsilyl-protected bromoaniline (0.625 g, 1.50 mmol, quant.), a golden yellow solid, via the general procedure.

0.263 g (0.655 mmol) of the above intermediate was converted to 3-NH$_2$ (0.123 g, 0.236 mmol, 76% based off Si-xanthone) via the general procedure.

$^1$H NMR (400 MHz, CDCl$_3$): δ 0.53 (s, 3H), 0.68 (s, 3H), 2.62 (t, 4H, J=4.4 Hz), 3.31 (t, 4H, J=4.4 Hz), 3.39 (s, 12H), 6.58 (d, 1H, J=2.7 Hz), 6.65 (dd, 2H, J=9.6 Hz, 2.8 Hz), 6.86 (dd, 1H, J=8.6 Hz, 2.7 Hz), 7.10 (d, 1H, J=8.6 Hz), 7.13 (d, 2H, J=2.8 Hz), 7.35 (d, 2H, J=9.6 Hz); $^{13}$C NMR (100 MHz, CDCl$_3$): δ −1.88, −0.24, 41.08, 52.74, 67.37, 113.61, 117.11, 117.37, 120.09, 122.99, 128.00, 136.46, 142.14, 142.19, 143.06, 147.95, 153.93, 171.69; HRMS (ESI): Calculated for C$_{29}$H$_{37}$N$_4$OSi [M−Cl]$^+$ 485.2731. found 485.2731.

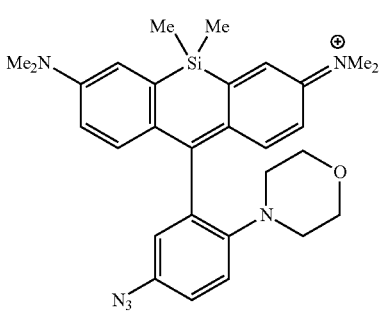

55.6 mg (0.107 mmol) 3-NH$_2$ was converted to 3-N$_3$ (42.1 mg, 0.0674 mmol, 63%) via the general procedure.

$^1$H NMR (500 MHz, CDCl$_3$): δ 0.52 (s, 3H), 0.65 (s, 3H), 2.75 (t, 4H, J=4.6 Hz), 3.35 (t, 4H, J=4.6 Hz), 3.38 (s, 12H), 6.67 (dd, 2H, J=9.6 Hz, 2.9 Hz), 6.76 (d, 1H, J=2.6 Hz), 7.19 (m, 6H); $^{13}$C NMR (125 MHz, CDCl$_3$): δ −1.83, 0.06, 31.01, 52.12, 67.11, 114.03, 120.68, 121.02, 121.46, 122.52, 127.40, 135.51, 135.85, 141.70, 147.92, 148.25, 154.10, 168.03; HRMS (ESI): Calculated for C$_{29}$H$_{35}$N$_6$OSi [M−TFA]$^+$ 511.2636. found 511.2636.

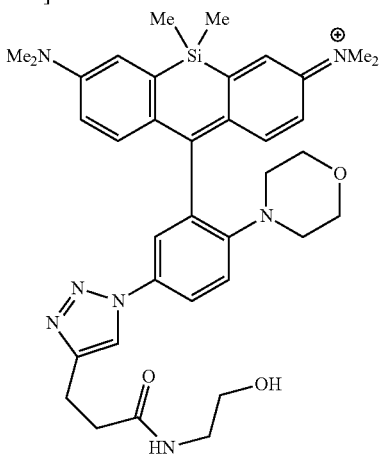

6.3 mg (0.010 mmol) 9-N$_3$ was converted to 9-triazole (6.17 mg, 0.0081 mmol, 81%) via the general procedure.

HRMS (ESI): Calculated for C$_{36}$H$_{46}$N$_7$O$_3$Si [M−TFA]$^+$ 652.3426. found 652.3425.

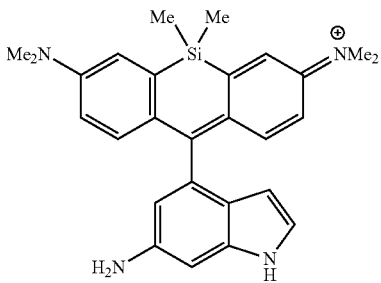

0.363 g (1.72 mmol) 4-bromo-6-amino indole, a brown solid, was dissolved in 5.1 mL dry THF and the light brown solution cooled to −78° C. Next, 3.1 mL (1.72 mmol) of freshly prepared 0.6 M LiHMDS solution, also cooled to −78° C., was added dropwise via cannula, turning the solution of indole a deep red brown. The solution was stirred at −78° C. for 10 min, warmed to rt for 5 min, then cooled to −78° C. again, during which it turned a cloudy brown. Finally, 0.218 mL (0.187 g, 1.72 mmol, 1 equiv.) trimethylsilyl chloride was added dropwise. The solution was warmed to rt and stirred for 4 h. The solution was cooled to −78° C. and another 6.2 mL (3.61 mmol) of 0.6 M LiHMDS solution was added via cannula at −78° C. The solution was stirred at −78° C. for 10 min, then warmed to rt for 5 min and cooled back to −78° C. 0.42 ml TMSCl was added. The reaction was warmed to rt and stirred overnight (16 h). The solution was concentrated, taken up in 50 mL hexanes and filtered, yielding tris-TMS-protected bromoindole (0.697 g, 0.796 mmol, 46%) contaminated with significant amounts of tris-trimethysilyl amine (~1.9 equiv. by NMR) as a brown oil.

0.570 g (0.655 mmol) of the tris-protected bromoindole was converted to a 1:1 mix of 4-NH$_2$ and TMS-protected-4-NH$_2$ (53 mg, 0.111 mmol, 36% based off Si-xanthone) as a blue solid. Analytically pure material could be obtained by HPLC purification using 20-100% MeCN/H$_2$O+0.1% TFA.

$^1$H NMR (500 MHz, CD$_3$OD): δ 0.62 (s, 3H), 0.66 (s, 3H), 3.33 (s, 12H), 6.06 (d, 1H, J=3.2 Hz), 6.67 (dd, 2H, J=9.7 Hz, 2.9 Hz), 6.93 (d, 1H, J=1.8 Hz), 7.10 (d, 2H, J=9.7 Hz), 7.37 (app. d, 3H, J=2.8 Hz), 7.60 (d, 1H, J=1.8 Hz); $^{13}$C NMR (100 MHz, CD$_3$OD): δ −1.15, −1.07, 40.87, 101.74, 106.67, 114.94, 115.61, 122.15, 128.63, 129.03, 129.12, 133.62, 137.08, 142.96, 149.50, 155.74, 168.65; HRMS (ESI): Calculated for C$_{27}$H$_{31}$N$_4$Si [M−Cl]$^+$ 439.2313. found 439.2309.

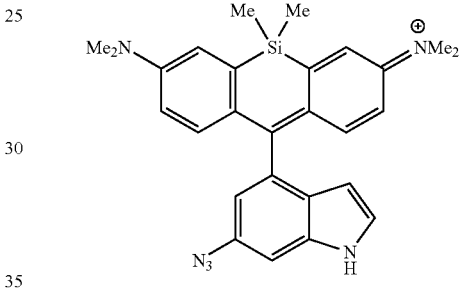

23.7 mg (0.050 mmol) 4-NH$_2$ was converted to 4-N$_3$ (9.6 mg, 0.016 mmol, 34%), a blue solid, via the general procedure.

$^1$H NMR (500 MHz, CDCl$_3$): δ 0.61 (s, 3H), 0.61 (s, 3H), 3.29 (s, 12H), 5.89 (s, 1H), 6.43 (dd, 2H, J=9.6 Hz, 2.8 Hz), 6.55 (d, 1H, J=1.8 Hz), 7.10 (d, 2H, J=2.8 Hz), 7.18 (d, 2H, J=9.6 Hz), 7.26 (s, 1H), 7.44 (s, 1H), 12.06 (brs, 1H); $^{13}$C NMR (125 MHz, CDCl$_3$): δ −0.76, −0.68, 40.88, 99.82, 103.58, 112.08, 113.77, 120.35, 126.39, 128.10, 128.18, 130.93, 133.08, 136.88, 143.12, 148.47, 154.21, 170.78; HRMS (ESI): Calculated for C$_{27}$H$_{29}$N$_6$Si [M−TFA]$^+$ 465.2218. found 465.2214.

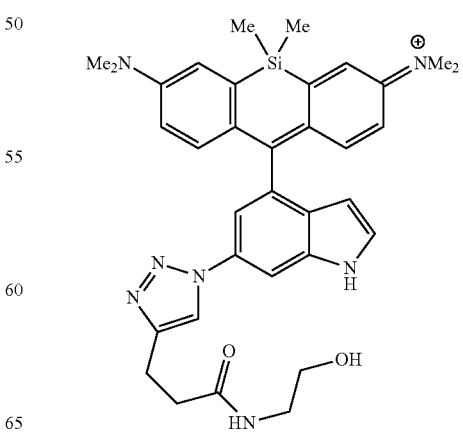

2.9 mg (0.0050 mmol) of 4-N₃ was converted to 4-triazole (2.9 mg, 0.0040 mmol, 80%), a blue solid, via the general procedure.

HRMS (ESI): Calculated for $C_{34}H_{40}N_7O_2Si$ [M–TFA]⁺ 606.3007. found 606.2998.

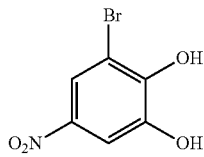

The starting material 2-bromo-6-methoxy-4-nitrophenol was prepared according to literature procedure.[5] 1.24 g (5.00 mmol) 2-bromo-6-methoxy-4-nitrophenol, a yellow powder, was suspended in 10 mL AcOH and 10 mL 48% HBr. The suspension refluxed overnight under $N_2$. After 20 h, the solution was cooled to rt, diluted with 100 mL 50% brine, extracted with 5×150 mL $CH_2Cl_2$, dried over $MgSO_4$, and concentrated to yield S1 (1.12 g, 4.78 mmol, 96%) as a yellow-brown solid.

$R_f$=0.55 (1:1 hex/EtOAc, UV/$I_2$); ¹H NMR (500 MHz, d₆-DMSO): δ 7.61 (d, 1H, J=2.7 Hz), 7.88 (d, 1H, J=2.7 Hz), 10.95 (brs, 2H); ¹³C NMR (125 MHz, d₆-DMSO): δ 108.74, 109.21, 119.28, 139.34, 145.79, 150.22; HRMS (ESI): Calculated for $C_6H_3BrNO_4$ [M–H]⁻ 231.9251. found 231.9251.

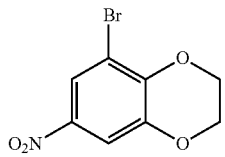

1.17 g (5.00 mmol) S1, a yellow-brown solid, was dissolved in 7.5 mL ethylene glycol. 1.42 g (10.25 mmol, 2.05 equiv.) potassium carbonate, a white powder, was added, turning the light yellow solution a deep red. Next, 0.86 mL 1,2-dibromoethane, a clear liquid, (1.88 g, 10.00 mmol, 2 equiv.), was added and the solution heated to 120° C. under $N_2$ for 12 h. Another 0.21 mL 1,2-dibromoethane, a clear liquid, was added, and the solution heated to 120° C. for another 4 h. The cloudy red solution was cooled to rt, diluted with 100 mL $H_2O$, extracted with 5×100 mL $CH_2Cl_2$, dried over $MgSO_4$, and concentrated, yielding a light brown solid. The solid was purified by flash chromatography with hexanes to 7:1 hexanes/EtOAc to yield S2 (0.752 g, 2.89 mmol, 58%) as a white solid.

$R_f$=0.15 (10:1 hex/EtOAc, UV); ¹H NMR (500 MHz, CDCl₃): δ 4.34 (m, 2H), 4.47 (m, 2H), 7.76 (d, 1H, J=2.6 Hz), 8.07 (d, 1H, J=2.6 Hz); ¹³C NMR (100 MHz, CDCl₃): δ 64.15, 65.57, 110.86, 112.78, 121.26, 141.58, 143.87, 146.69; HRMS (EI): Calculated for $C_8H_6BrNO_4$ [M⁺] 258.9480. found 258.9475.

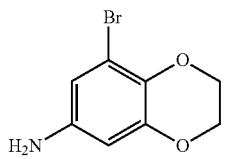

0.724 g (2.78 mmol) S2, a white solid, was covered with 10 mL AcOH. Next, 0.466 g iron, a grey powder, (8.35 mmol, 3 equiv.), was added. The suspension was vigorously stirred at 100° C. under $N_2$ for 1 h, turning to a cloudy yellow-grey slurry. The solution was cooled to rt and diluted with 80 mL 50% brine and extracted with 3×80 mL $CH_2Cl_2$, dried over $MgSO_4$, and concentrated, yielding a pale pink oil. The oil was purified by flash chromatography with 3:1 to 1:1 hexanes/EtOAc to yield S3 (0.309 g, 1.34 mmol, 48%) as a light pink oil.

$R_f$=0.45 (4:1 hex/EtOAc, UV/$I_2$); ¹H NMR (600 MHz, CDCl₃): δ 3.53 (brs, 2H), 4.22 (m, 2H), 4.27 (m, 2H), 6.20 (d, 2H, J=2.7 Hz), 6.48 (d, 2H, J=2.7 Hz); ¹³C NMR (125 MHz, CDCl₃): δ 64.42, 64.59, 103.50, 110.58, 111.96, 133.55, 140.87, 144.58; HRMS (ESI): Calculated for $C_8H_9BrNO_2$ [M+H]⁺ 229.9811. found 229.9812.

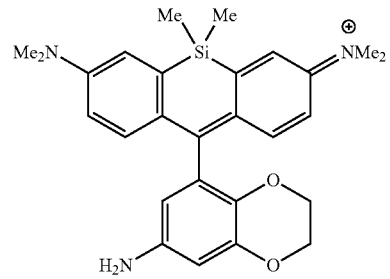

0.309 g (1.50 mmol) S3 was converted to bis-trimethylsilyl-protected bromoaniline (0.625 g, 1.50 mmol, quant.), a red-brown oil, via the general procedure.

0.245 g (0.655 mmol) of the above intermediate was converted to 5-NH₂ (0.106 g, 0.214 mmol, 69% based off Si-xanthone), a blue solid, via the general procedure.

¹H NMR (600 MHz, CDCl₃): δ 0.54 (s, 3H), 0.55 (s, 3H), 3.36 (s, 12H), 3.98 (t, 2H, J=3.9 Hz), 4.16 (t, 2H, J=3.8 Hz), 6.07 (d, 1H, J=2.7 Hz), 6.35 (d, 1H, J=2.7 Hz), 6.64 (dd, 2H, J=9.6 Hz, 2.9 Hz), 7.08 (d, 2H, J=2.9 Hz), 7.37 (d, 2H, J=9.6 Hz); ¹³C NMR (151 MHz, CDCl₃): δ –0.77, –0.62, 41.15, 64.37, 64.78, 104.72, 109.92, 114.00, 120.48, 127.74, 127.97, 133.89, 140.81, 142.24, 144.05, 148.24, 154.24, 167.85; HRMS (ESI): Calculated for $C_{27}H_{32}N_3O_2Si$ [M–Cl]⁺ 458.2258. found 458.2252.

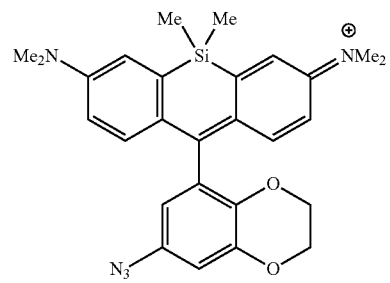

71.2 mg 5-NH₂ (0.144 mmol) was converted to 5-N₃ (33.7 mg, 0.056 mmol, 39%), a blue solid, via the general procedure.

¹H NMR (400 MHz, CDCl₃): δ 0.56 (s, 3H), 0.58 (s, 3H), 3.37 (s, 12H), 4.11 (m, 2H), 4.26 (m, 2H), 6.35 (d, 1H, J=2.6 Hz), 6.68 (dd, 2H, J=2.6 Hz, 9.6 Hz), 6.71 (d, 1H, J=2.6 Hz), 7.13 (d, 2H, J=2.7 Hz), 7.23 (d, 2H, J=9.5 Hz); ¹³C NMR (151 MHz, CDCl₃): δ –0.94, –0.76, 41.04, 64.57, 64.68, 108.79, 112.94, 114.21, 120.89, 127.71, 128.69, 133.33, 138.77, 141.58, 144.71, 148.49, 154.33, 165.23; HRMS (ESI): Calculated for $C_{27}H_{30}N_5O_2Si$ [M−TFA]$^+$ 484.2163. found 484.2158.

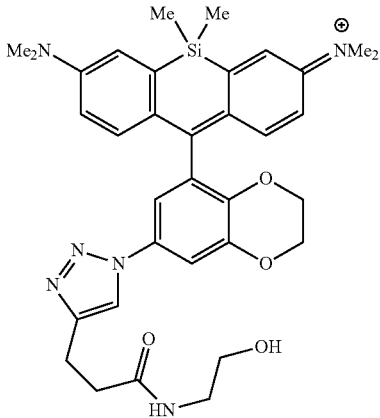

6.0 mg 5-N$_3$ (0.010 mmol) was converted to 5-triazole (5.3 mg, 0.0072 mmol, 72%), a blue solid, via the general procedure.

HRMS (ESI): Calculated for $C_{34}H_{41}N_6O_4Si$ [M−TFA]$^+$ 625.2953. found 625.2939.

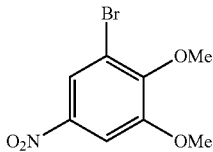 [SMILES: COc1cc([N+](=O)[O-])cc(Br)c1OC]

0.992 g (4.00 mmol) 2-bromo-6-methoxy-4-nitrophenol, a pale-yellow solid, was suspended in 5.6 mL dry DMF in a flame-dried flask. Next, 1.10 g (8.00 mmol, 2 equiv.) potassium carbonate, a white powder and 0.320 mL (0.738 g, 5.20 mmol, 1.3 equiv.) methyl iodide, a clear liquid, were added. A reflux condenser was attached and the reaction mixture heated to 40° C. under N$_2$ for 6 h. The now orange-brown suspension was cooled to rt, then diluted with 25 mL H$_2$O, turning the solution a cloudy yellow. The product was extracted with 3×25 mL Et$_2$O and the combined ether layers washed with 25 mL H$_2$O and 2×25 mL brine, dried over MgSO$_4$, and concentrated, yielding S4 (0.938 g, 3.58 mmol, 89%) as an light brown solid.

R$_f$=0.40 (10:1 hexanes/EtOAc, UV); $^1$H NMR (600 MHz, CDCl$_3$): δ 3.97 (s, 3H), 3.97 (s, 3H), 7.75 (d, 1H, J=2.6 Hz), 8.10 (d, 1H, J=2.6 Hz); $^{13}$C NMR (151 MHz, CDCl$_3$): δ 56.49, 60.93, 106.91, 117.31, 120.72, 143.76, 151.98, 153.21; HRMS (EI): Calculated for $C_8H_8BrNO_4$ [M$^+$] 260.9637 found 260.9637.

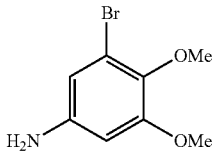

0.852 g (3.25 mmol) S4, a light brown solid, was suspended in 12 mL AcOH. 0.544 g (9.75 mmol, 3 equiv.) iron, a grey powder, was added and the grey suspension heated to 100° C. for 1 h. The now light brown slurry was cooled to rt and diluted with 80 mL 50% brine and extracted with 3×80 mL CH$_2$Cl$_2$. The organic layers were dried over MgSO$_4$ and concentrated, yielding a pink oil. The oil was purified by flash chromatography with 3:1 to 1:1 hexanes/EtOAc, yielding S5 (0.469 g, 2.02 mmol, 62%) as an off-white solid.

R$_f$=0.40 (1:1 hexanes/EtOAc, UV/I$_2$); $^1$H NMR (500 MHz, CDCl$_3$): δ 3.57 (brs, 2H), 3.76 (s, 3H), 3.81 (s, 3H), 6.20 (d, 1H, J=2.4 Hz), 6.45 (d, 1H, J=2.4 Hz); $^{13}$C NMR (151 MHz, CDCl$_3$): δ 55.94, 60.81, 99.60, 110.24, 138.83, 143.93, 154.12; HRMS (ESI): Calculated for $C_8H_{11}BrNO_2$ [M+H]$^+$ 231.9968. found 231.9969.

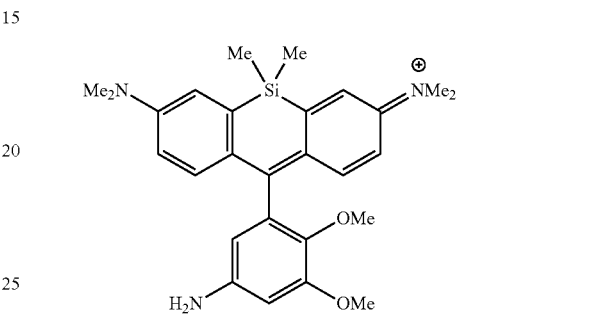

0.464 g (2.00 mmol) S5 was converted to bis-trimethylsilyl-protected bromoaniline (0.766 g, 2.00 mmol, quant.), a red-brown oil, via the general procedure.

0.245 g (0.655 mmol) of the above intermediate was converted to 6-NH$_2$ (0.106 g, 0.214 mmol, 69% based off Si-xanthone), a blue solid, via the general procedure.

$^1$H NMR (400 MHz, CDCl$_3$): δ 0.55 (s, 3H), 0.57 (s, 3H), 3.32 (s, 12H), 3.52 (s, 3H), 3.93 (s, 3H), 6.58 (s, 1H), 6.63 (dd, 2H, J=9.6 Hz, 2.8 Hz), 7.08 (d, 2H, J=2.8 Hz), 7.10 (s, 1H), 7.28 (d, 2H, J=9.6 Hz), 8.45 (brs, 2H); $^{13}$C NMR (151 MHz, CD$_3$OD): δ −1.37, −0.95, 40.91, 56.19, 61.20, 101.84, 108.79, 114.79, 121.76, 128.86, 134.63, 139.44, 143.12, 145.77, 149.30, 154.61, 155.3, 169.42; HRMS (ESI): Calculated for $C_{27}H_{34}N_3O_2Si$ [M−Cl]$^+$ 460.2415. found 460.2411.

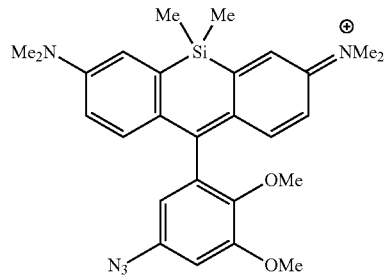

51.8 mg (0.104 mmol) 6-NH$_2$ was converted to 6-N$_3$ (32.3 mg, 0.054 mmol, 52%), a blue solid, via the general procedure.

$^1$H NMR (500 MHz, CDCl$_3$): δ 0.59 (s, 3H), 0.59 (s, 3H), 3.36 (s, 12H), 3.56 (s, 3H), 3.95 (s, 3H), 6.40 (d, 1H, J=2.5 Hz), 6.66 (dd, 2H, J=9.6 Hz, 2.4 Hz), 6.68 (d, 1H, J=2.5 Hz), 7.16 (d, 2H, J=2.6 Hz), 7.23 (d, 2H, J=9.5 Hz); $^{13}$C NMR (100 MHz, CDCl$_3$): δ −0.98, −0.81, 41.05, 56.17, 61.17, 104.40, 111.57, 114.04, 120.86, 127.65, 134.00, 136.21, 141.70, 143.55, 148.46, 153.90, 154.29, 165.79; Calculated for $C_{27}H_{32}N_5O_2Si$ [M−TFA]$^+$ 486.2320. found 486.2316.

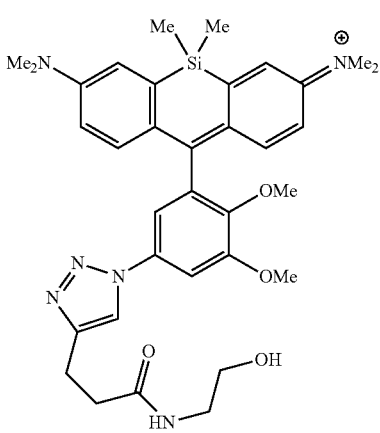

3.0 mg (0.0050 mmol) 6-N₃ was converted to 6-triazole (3.1 mg, 0.0042 mmol, 84%), a blue solid, via the general procedure.
HRMS (ESI): Calculated for $C_{34}H_{43}N_6O_4Si$ [M−TFA]⁺ 627.3110. found 627.3107.

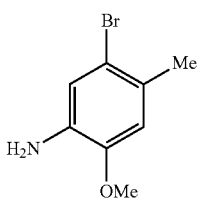

The starting material 1-bromo-4-methoxy-2-methyl-5-nitrobenzene was prepared according to literature procedure.[6] 0.505 g (2.05 mmol) 1-bromo-4-methoxy-2-methyl-5-nitrobenzene, a yellow solid, was dissolved in 8.8 mL AcOH. Next, 0.344 g (6.14 mmol, 3 equiv.) iron, a grey powder, was added and the grey suspension heated to 100° C. under N₂ for 1 h. The now greenish-grey slurry was cooled to rt and diluted with 50 mL H₂O, extracted with 3×30 mL ethyl acetate, dried over MgSO₄, and concentrated. The crude product was then purified with flash chromatography using hexanes to 10:1 hexanes/EtOAc to yield S6 (0.364 g, 1.69 mmol, 82%) as a clear oil.

$R_f$=0.25 (10:1 hexanes/EtOAc, UV/I₂); ¹H NMR (500 MHz, CDCl₃): δ 2.29 (s, 3H), 3.70 (brs, 2H), 3.82 (s, 3H), 6.63 (s, 1H), 6.87 (s, 1H);); ¹³C NMR (151 MHz, CDCl₃): δ 22.37, 55.80, 112.88, 115.22, 118.32, 135.37, 146.77; HRMS (ESI): Calculated for $C_8H_{11}BrNO$ [M+H]⁺ 216.0019. found 216.0019.

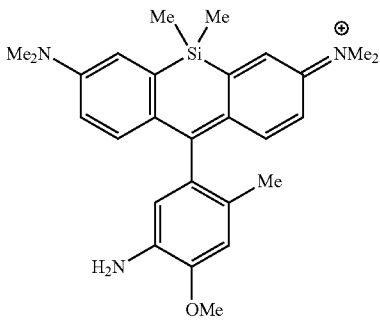

0.323 g (1.49 mmol) S6 was converted to bis-trimethylsilyl-protected bromoaniline (0.549 g, 1.49 mmol, quant.), an orange oil, via the general procedure.

0.236 g (0.655 mmol) of the above intermediate was converted to 7-NH₂ (0.153 g, 0.312 mmol, quant. based off Si-xanthone), a blue solid, via the general procedure.

¹H NMR (600 MHz, CDCl₃): δ 0.59 (s, 3H), 0.62 (s, 3H), 1.90 (s, 3H), 3.39 (s, 12H), 3.93 (s, 3H), 6.51 (s, 1H), 6.63 (dd, 2H, J=9.7 Hz, 2.6 Hz), 6.70 (s, 1H), 7.16 (d, 2H, J=2.6 Hz), 7.25 (d, 2H, J=9.7 Hz); ¹³C NMR (151 MHz, CDCl₃): δ −1.01, −0.66, 18.91, 41.09, 55.64, 111.84, 113.85, 115.73, 120.33, 125.21, 127.98, 130.29, 133.80, 142.19, 147.55, 148.19, 154.02, 171.52; HRMS (ESI): Calculated for $C_{27}H_{34}N_3OSi$ [M−Cl]⁺ 444.2466. found 444.2461.

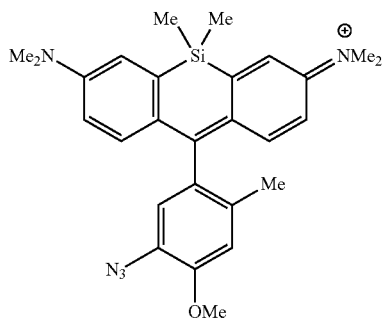

20.0 mg (0.045 mmol) 7-NH₂ was converted to 7-N₃ (17.5 mg, 0.037 mmol, 83%), a blue solid, via the general procedure.

¹H NMR (600 MHz, CDCl₃): δ 0.58 (s, 3H), 0.59 (s, 3H), 1.99 (s, 3H), 3.37 (s, 12H), 3.97 (s, 3H), 6.65 (dd, 2H, J=9.6 Hz, 2.8 Hz), 6.70 (s, 1H), 6.86 (s, 1H), 7.11 (d, 2H, J=9.6 Hz), 7.16 (d, 2H, J=2.9 Hz); 13C NMR (151 MHz, CDCl₃): δ −1.09, −0.85, 19.41, 40.92, 56.23, 113.95, 114.17, 120.74, 120.77, 126.07, 127.71, 130.98, 133.74, 141.56, 148.40, 152.11, 154.18, 168.60; HRMS (ESI): Calculated for $C_{27}H_{32}NOSi$ [M−TFA]⁺ 470.2371. found 470.2367.

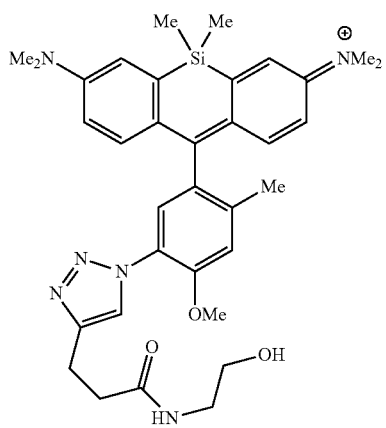

3.0 mg (0.0051 mmol) 7-N₃ was converted to 7-triazole (2.4 mg, 0.0034 mmol, 67%), a blue solid, via the general procedure.

HRMS (ESI): Calculated for $C_{34}H_{43}O_3N_6Si$ [M−TFA]⁺ 611.3160. found 611.3160.

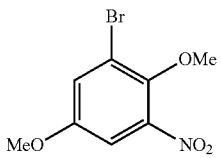

1.24 g (5.00 mmol) 2-bromo-4-methoxy-6-nitrophenol, a bright orange crystalline solid, was dissolved in 7 mL dry DMF in a flame-dried flask. Next, 1.38 g (10.0 mmol, 2 equiv.) potassium carbonate, a white powder, was added, turning the solution a deep red color Finally, 0.40 mL (0.923 g, 6.50 mmol, 1.3 equiv.) methyl iodide, a clear liquid, was added, a reflux condenser attached, and the solution heated to 40° C. overnight (10 h). The now cloudy light brown solution was cooled and diluted with 30 mL H$_2$O, causing a white precipitate to form. The product was extracted with 3×30 mL Et$_2$O and the organic layers washed with 30 mL H$_2$O and 2×30 mL brine, dried over MgSO$_4$, and concentrated, yielding S7 (1.28 g, 4.88 mmol, 98%) as an off-white solid.

R$_f$=0.45 (10:1 hex/EtOAc, UV); $^1$H NMR (500 MHz, CDCl$_3$): δ 3.83 (s, 3H), 3.96 (s, 3H), 7.28 (d, 1H, J=3.1 Hz), 7.35 (d, 1H, J=3.5 Hz); $^{13}$C NMR (151 MHz, CDCl$_3$): δ 55.72, 59.97, 101.34, 107.17, 117.09, 138.78, 141.60, 154.70, 156.94; HRMS (EI): Calculated for C$_8$H$_8$BrNO$_4$ [M$^+$] 260.9637. found 260.9644.

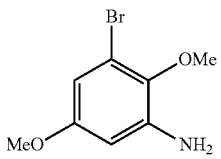

1.07 g (4.06 mmol) S7, an off-white powder, was dissolved in 15 mL AcOH. Next, 0.681 g (12.19 mmol, 3 equiv.) iron, a grey powder, was added and the grey suspension heated to 100° C. under N$_2$ for 1 h. The now brown slurry was cooled to rt, diluted with 50 mL 50% brine and extracted with 3×50 mL CH$_2$Cl$_2$. The organic layers were dried over MgSO$_4$ and concentrated, yielding a brown oil. The oil was purified with flash chromatography using 4:1 to 2:1 hexanes/EtOAc to yield S8 (0.747 g, 3.22 mmol, 79%) as a pale-yellow oil.

R$_f$=0.55 (1:1 hex/EtOAc, UV); $^1$H NMR (500 MHz, CDCl$_3$): δ 3.71 (s, 3H), 3.78 (s, 3H), 3.94 (brs, 2H), 6.24 (d, 1H, J=2.9 Hz), 6.46 (d, 1H, J=2.9 Hz); $^{13}$C NMR (151 MHz, CDCl$_3$): δ 56.41, 62.85, 109.36, 120.30, 124.01, 144.68, 145.23, 155.69; HRMS (ESI): Calculated for C$_8$H$_{11}$BrNO$_2$ [M+H]$^+$ 231.9968. found 231.9969.

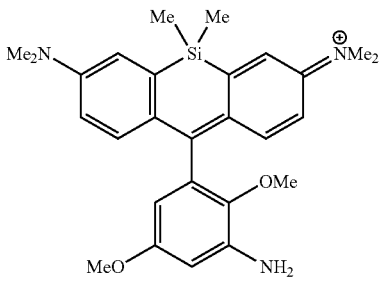

0.580 g (2.50 mmol) S8 was converted to bis-trimethylsilyl-protected bromoaniline (0.891 g, 2.37 mmol, 95%), a golden-yellow oil, via the general procedure.

0.247 g (0.655 mmol) of the above intermediate was converted to 8-NH$_2$ (0.121 g, 0.244 mmol, 78% based off Si-xanthone), a blue solid, via the general procedure.

$^1$H NMR (400 MHz, CDCl$_3$): δ 0.59 (s, 3H), 0.63 (s, 3H), 3.41 (s, 12H), 3.75 (s, 3H), 6.02 (d, 1H, J=2.9 Hz), 6.55 (d, 1H, J=2.9 Hz), 6.68 (dd, 2H, J=9.6 Hz, 2.8 Hz), 7.18 (d, 2H, J=2.8 Hz), 7.42 (d, 2H, J=9.6 Hz); $^{13}$C NMR (125 MHz, CDCl$_3$): δ −1.31, −0.56, 41.00, 55.52, 60.15, 101.97, 104.66, 113.71, 120.35, 127.56, 132.36, 138.42, 141.37, 142.16, 147.98, 153.95, 155.75, 167.63; HRMS (ESI): Calculated for C$_{27}$H$_{34}$N$_3$O$_2$Si [M−Cl]$^+$ 460.2415. found 460.2412.

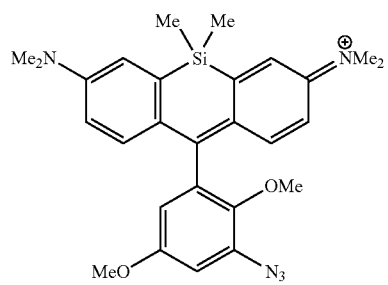

54.4 mg (0.110 mmol) 8-NH$_2$ was converted to 8-N$_3$ (66.3 mg, 0.110 mmol, quant.), a blue solid, via the general procedure.

$^1$H NMR (600 MHz, CDCl$_3$): δ 0.57 (s, 3H), 0.60 (s, 3H), 3.37 (s, 12H), 3.48 (s, 3H), 3.80 (s, 3H), 6.43 (d, 1H, J=2.8 Hz), 6.67 (dd, 2H, J=9.6 Hz, 2.7 Hz), 6.75 (d, 1H, J=2.8 Hz), 7.16 (d, 2H, J=2.8 Hz), 7.24 (d, 2H, J=9.5 Hz); $^{13}$C NMR (125 MHz, CDCl$_3$): δ −1.21, −0.56, 41.04, 56.05, 62.12, 107.03, 111.83, 114.15, 120.90, 127.63, 134.52, 134.56, 141.72, 143.06, 148.40, 154.30, 155.95, 165.44; HRMS (ESI): Calculated for C$_{27}$H$_{32}$N$_5$O$_2$Si [M−TFA]$^+$ 486.2320. found 486.2317.

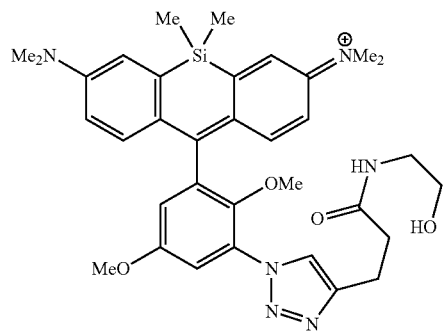

6.0 mg (0.010 mmol) 8-N$_3$ was converted to 8-triazole (3.4 mg, 0.0046 mmol, 46%), a blue solid, via the general procedure.

HRMS (ESI): Calculated for C$_{34}$H$_{43}$N$_6$O$_4$Si [M−TFA]$^+$ 627.3110. found 627.3106.

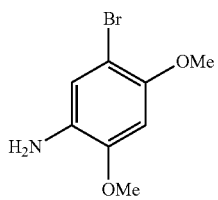

The starting material 1-bromo-2,4-dimethoxy-5-nitrobenzene was prepared according to literature procedure.[7] 1.30 g (5.00 mmol) 1-bromo-2,4-dimethoxy-5-nitrobenzene, an off-white solid, was suspended in 15 mL AcOH. To the light yellow suspension was added 0.837 g (15.0 mmol, 3 equiv.) iron, a grey powder. The now grey suspension was heated to 100° C. under $N_2$ for 1 h. The cloudy grey slurry was cooled to rt, diluted with 100 mL 50% brine, and extracted with 3×60 mL $CH_2Cl_2$. The combined organic layers were carefully washed with 50 mL $NaHCO_3$ (caution: gas evolution!), dried over $MgSO_4$, and concentrated, yielding a yellow-orange solid. The solid was purified with flash chromatography with 3:1 hexanes/EtOAc to yield S9 (0.956 g, 4.12 mmol, 82%) as an off-white solid.

$R_f$=0.70 (1:1 hex/EtOAc, $UV/I_2$); $^1H$ NMR (500 MHz, $CDCl_3$): δ 3.56 (brs, 2H), 3.83 (s, 3H), 3.85 (s, 3H), 6.49 (s, 1H), 6.89 (s, 1H); $^{13}C$ NMR (151 MHz, $CDCl_3$): δ 55.97, 57.68, 98.81, 102.43, 119.09, 131.19, 147.46, 149.00; HRMS (ESI): Calculated for $C_8H_{11}BrNO_2$ $[M+H]^+$ 231.9968. found 231.9968.

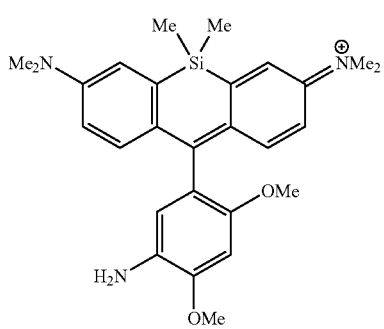

0.464 g S9 (2.00 mmol) was converted to the bis-trimethylsilyl protected bromoaniline (0.709 g, 1.90 mmol, 95%), a red-brown solid, via the general procedure.

0.245 g (0.655 mmol) of this intermediate was then converted to 9-$NH_2$ (0.141 g, 0.284 mmol, 91% based off Si-xanthone), a blue solid, via the general procedure.

$^1H$ NMR (500 MHz, $CDCl_3$): δ 0.54 (s, 3H), 0.56 (s, 3H), 3.35 (s, 12H), 3.60 (s, 3H), 3.95 (s, 3H), 6.47 (s, 1H), 6.56 (s, 1H), 6.62 (dd, 2H, J=9.6 Hz, 2.8 Hz), 7.08 (d, 2H, J=2.8 Hz), 7.31 (d, 2H, J=9.5 Hz); 13C NMR (125 MHz, $CDCl_3$): δ −0.76, −0.60, 41.15, 55.98, 56.99, 96.78, 113.80, 116.86, 119.35, 120.25, 128.61, 129.74, 142.52, 148.20, 148.85, 149.61, 154.08, 169.56; HRMS (ESI): Calculated for $C_{27}H_{34}N_3O_2Si$ $[M-Cl]^+$ 460.2420. found 460.2408.

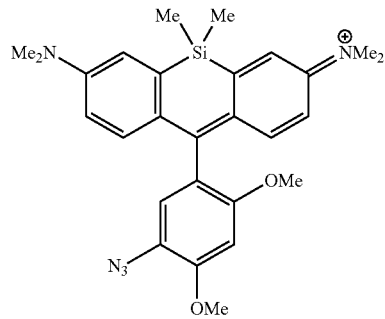

76.6 mg (0.155 mmol) 9-$NH_2$ was converted to 9-$N_3$ (63.4 mg, 0.105 mmol, 68%), a blue solid, via the general procedure.

$^1H$ NMR (600 MHz, $CDCl_3$): δ 0.60 (s, 3H), 0.63 (s, 3H), 3.40 (s, 12H), 3.76 (s, 3H), 4.07 (s, 3H), 6.71 (dd, 2H, J=2.8 Hz, 9.6 Hz), 6.72 (s, 1H), 6.72 (s, 1H), 7.15 (d, 2H, J=2.8 Hz), 7.25 (d, 2H, J=9.6 Hz); $^{13}C$ NMR (125 MHz, $CDCl_3$): δ −1.04, −0.76, 40.88, 56.41, 56.46, 96.91, 113.95, 119.65, 120.46, 120.69, 121.77, 128.24, 141.88, 148.27, 153.60, 154.12, 154.73, 166.98; HRMS (ESI): Calculated for $C_{27}H_{32}N_5O_2Si$ $[M-TFA]^+$ 486.2320. found 486.2314.

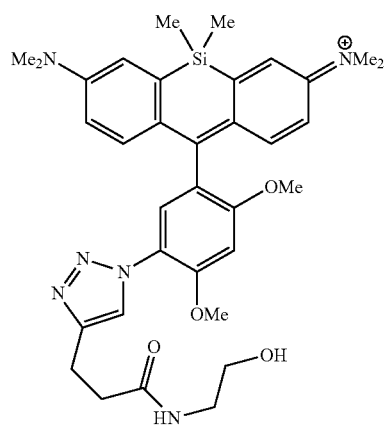

6.0 mg (0.010 mmol) 9-$N_3$ was converted to 9-triazole (1.85 mg, 0.0025 mmol, 25%), a blue solid, via the general procedure.

HRMS (ESI): Calculated for $C_{34}H_{43}N_6O_4Si$ $[M-TFA]^+$ 627.3110. found 627.3100.

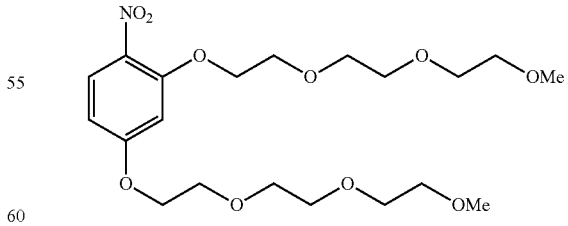

1.31 mL (1.91 g, 12.0 mmol) 2,4-difluoronitrobenzene, a pale yellow liquid, was dissolved in 10 mL toluene. Next, 7.52 mL (7.88 g, 48.0 mmol, 4 equiv.) triethylene glycol monomethyl ether, a clear liquid, was added. 10 mL 50% KOH was then added, immediately warming the solution and turning it a golden yellow color. Finally, 387 mg (1.20 mmol, 0.1 equiv.) tetrabutylammonium bromide, a white solid, was added and the solution vigorously stirred at 60° C. overnight (16 h). The solution was cooled to rt and diluted with 80 mL cold brine. The product was then extracted with 3×80 mL ethyl acetate, the organic layer washed with 3×120 mL sat. NaHCO$_3$, dried over MgSO$_4$, and concentrated, yielding S10 (5.19 g, 11.6 mmol, 97%) as a yellow oil.

R$_f$=0.70 (10:1 CHCl$_3$/MeOH, UV); $^1$H NMR (400 MHz, CDCl$_3$): δ 3.37 (s, 3H), 3.38 (s, 3H), 3.55 (m, 4H), 3.67 (m, 8H), 3.73 (m, 2H), 3.78 (m, 2H), 3.87 (t, 2H, J=4.8 Hz), 3.92 (t, 2H, J=4.8 Hz), 6.51 (dd, 1H, J=9.1 Hz, 2.5 Hz), 6.59 (d, 1H, J=2.5 Hz), 7.96 (d, 1H, J=9.1 Hz); $^{13}$C NMR (100 MHz, CDCl$_3$): δ 59.06, 59.10, 68.18, 69.25, 69.44, 69.66, 70.54, 70.64, 70.70, 70.72, 70.93, 70.97, 71.17, 71.96, 101.47, 105.78, 128.25, 133.32, 154.92, 163.90; HRMS (ESI): Calculated for C$_{20}$H$_{33}$NNaO$_{10}$ [M+Na]$^+$ 470.1997. found 470.2005.

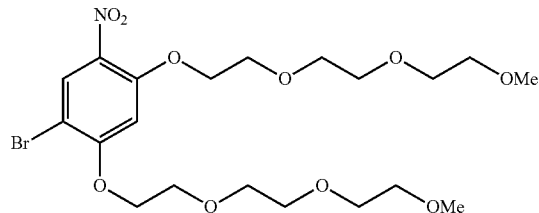

4.37 g (9.76 mmol) S10, a yellow oil, was dissolved in 20 mL CHCl$_3$. Next, 1.42 g (10.25 mmol, 1.05 equiv.) potassium carbonate, a white solid, was added. Finally, 0.526 mL (1.64 g, 10.25 mmol, 1.05 equiv.) bromine, a red liquid, was added dropwise to the vigorously stirring solution. Bubbling was observed. The red solution was stirred for 2 h in the dark. Another 0.1 mL bromine was added and the reaction stirred for 1 h, then quenched with 50 mL sat. Na$_2$S$_2$O$_3$, extracted with 3×50 mL CHCl$_3$, washed with 50 mL sat. Na$_2$S$_2$O$_3$, 3×50 mL sat. NaHCO$_3$, dried over MgSO$_4$ and concentrated to yield S11 (5.14 g, 9.76 mmol, quant.) as a pale brown oil.

R$_f$=0.75 (10:1 CHCl$_3$/MeOH, UV); $^1$H NMR (400 MHz, CDCl$_3$): δ 3.35 (s, 3H), 3.36 (s, 3H), 3.53 (m, 4H), 3.65 (m, 8H), 3.77 (m, 4H), 3.92 (m, 4H), 4.24 (t, 2H, J=4.4 Hz), 4.26 (t, 2H, J=4.4 Hz), 6.68 (s, 1H), 8.20 (s, 1H); $^{13}$C NMR (151 MHz, CDCl$_3$): δ 59.12, 59.15, 69.41, 69.48, 69.89, 70.39, 70.59, 70.67, 70.76, 70.81, 71.19, 71.30, 72.02, 72.04, 100.12, 102.48, 130.72, 133.23, 154.47, 160.21; HRMS (ESI): Calculated for C$_{20}$H$_{32}$BrNNaO$_{10}$ [M+Na]$^+$ 548.1102. found 548.1103.

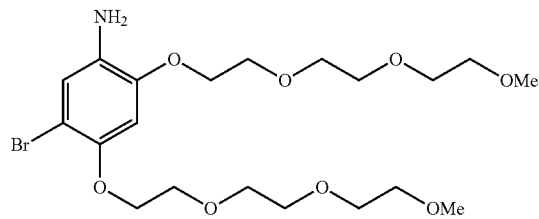 [SMILES: COCCOCCOCCOc1cc(OCCOCCOCCOC)c([N+](=O)[O-])cc1Br]

2.63 g (5.00 mmol) S11, a pale brown oil, was dissolved in 15 mL AcOH. Next, 0.838 g (15.0 mmol, 3 equiv.) iron, a grey powder, was added and the grey suspension stirred at 100° C. for 1 h. The grey slurry was cooled to rt, diluted with 50 mL 50% brine, and extracted with 3×30 mL CH$_2$Cl$_2$. The combined organic layers were carefully washed with 3×30 mL sat. NaHCO$_3$ (caution: gas evolution!), dried over MgSO$_4$, and concentrated, yielding a yellow oil. The oil was purified by flash chromatography using CHCl$_3$ to 20:1 CHCl$_3$/MeOH to 10:1 CHCl$_3$/MeOH to yield S12 (2.26 g, 4.55 mmol, 91%) as a brown oil.

R$_f$=0.50 (10:1 CHCl$_3$/MeOH, UV/I$_2$); $^1$H NMR (500 MHz, CDCl$_3$): δ 3.37 (s, 3H), 3.38 (s, 3H), 3.55 (m, 4H), 3.67 (m, 10H), 3.77 (m, 2H), 3.83 (m, 6H), 4.08 (t, 2H, J=5.0 Hz), 4.11 (t, 2H, J=5.0 Hz), 6.57 (s, 1H), 6.87 (s, 1H); $^{13}$C NMR (151 MHz, CDCl$_3$): δ 59.06, 59.06, 68.99, 69.64, 69.83, 70.56, 70.58, 70.65, 70.72, 70.77, 70.83, 70.97, 71.96, 71.96, 103.58, 104.56, 118.85, 132.83, 146.14, 147.80; HRMS (ESI): Calculated for C$_{20}$H$_{35}$BrNO$_8$ [M+H]$^+$ 496.1541. found 496.1542.

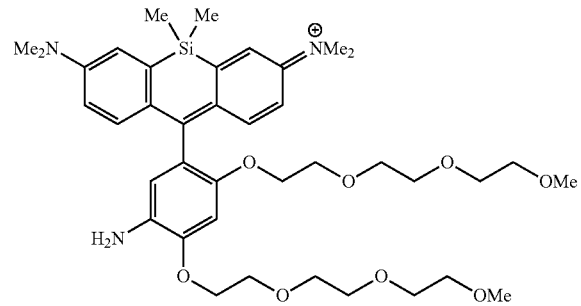

0.993 g (2.00 mmol) S12 was converted to the bis-trimethylsilyl-protected bromoaniline (1.28 g, 2.00 mmol, quant.), a red-brown oil, via the general procedure with one modification. Due to the poor solubility of the product in hexanes, the product was taken up and filtered in toluene instead.

0.420 g (0.655 mmol) of this intermediate was converted to 10-NH$_2$ (0.178 g, 0.234 mmol, 75% based off Si-xanthone), a blue solid, via the general procedure.

$^1$H NMR (500 MHz, CDCl$_3$): δ 0.55 (s, 3H), 0.60 (s, 3H), 3.33 (s, 3H), 3.39 (s, 19H), 3.47 (m, 4H), 3.51 (m, 2H), 3.57 (m, 2H), 3.67 (m, 2H), 3.61 (m, 2H), 3.72 (m, 2H), 3.90 (t, 2H, J=5.1 Hz), 3.93 (t, 2H, J=5.1 Hz), 6.49 (s, 1H), 6.64 (s, 1H), 6.64 (dd, 2H, J=9.6 Hz, 2.8 Hz), 7.13 (d, 2H, J=2.9 Hz), 7.34 (dd, 2H, J=9.6 Hz, 2.5 Hz); $^{13}$C NMR (151 MHz, CDCl$_3$): δ −1.11, −0.54, 41.03, 58.98, 59.02, 68.80, 69.68, 69.69, 69.94, 70.42, 70.49, 70.55, 70.62, 70.66, 70.79, 71.86, 71.95, 100.81, 113.70, 116.75, 120.19, 120.86, 128.53, 131.15, 142.54, 147.72, 148.11, 148.52, 154.04, 169.37; HRMS (ESI): Calculated for C$_{39}$H$_{58}$N$_3$O$_8$Si [M−Cl]$^+$ 724.3988. found 724.3983.

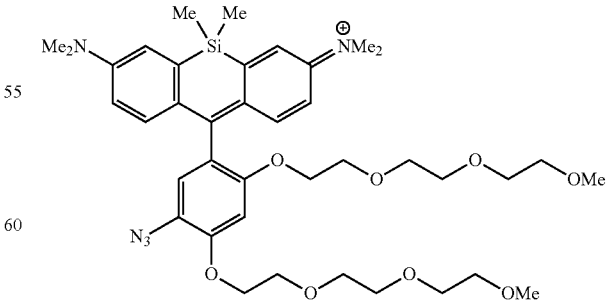

67.0 mg (0.0881 mmol) 10-NH$_2$ was converted to 10 (63.2 mg, 0.0783 mmol, 83%), a blue solid, via the general procedure.

¹H NMR (500 MHz, CDCl₃): δ 0.55 (s, 3H), 0.58 (s, 3H), 3.34 (s, 3H), 3.37 (s, 12H), 3.39 (s, 3H), 3.33-3.39 (m, 6H), 3.47 (app d, 2H, J=5.1 Hz), 3.50 (app d, 2H, J=4.8 Hz), 3.53 (t, 2H, J=4.9 Hz), 3.57 (t, 2H, J=4.7 Hz), 3.68 (t, 2H, J=4.6 Hz), 3.72 (t, 2H, J=4.7 Hz), 3.79 (t, 2H, J=4.7 Hz), 3.96 (t, 2H, J=4.7 Hz), 4.02 (t, 2H, J=5.0 Hz), 4.30 (t, 2H, J=4.7 Hz), 6.64 (s, 1H), 6.65 (dd, 2H, J=2.7 Hz, 9.7 Hz), 6.73 (s, 1H), 7.15 (d, 2H, J=2.7 Hz), 7.21 (d, 2H, J=9.7 Hz); ¹³C NMR (151 MHz, CDCl₃): δ −1.15, −0.75, 40.92, 59.02, 59.10, 69.29, 69.33, 69.51, 69.55, 70.44, 70.51, 70.58, 70.72, 70.74, 70.93, 71.90, 72.00, 99.81, 113.95, 120.51, 120.51, 121.52, 122.24, 128.35, 142.01, 148.34, 153.33, 153.98, 154.18, 167.05; HRMS (ESI): Calculated for C₃₉H₅₆O₈N₅Si₁ [M−TFA]⁺ 750.3892. found 750.3899.

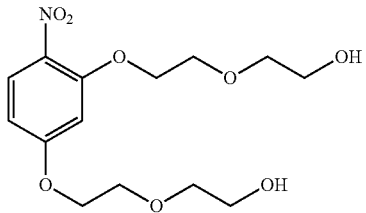 [SMILES: O=[N+]([O-])c1ccc(OCCOCCO)cc1OCCOCCO]

6.22 g (45.0 mmol, 3 equiv.) K₂CO₃, a white powder, was added to 50 mL diethylene glycol. Next, 1.65 mL (2.39 g, 15.0 mmol) 2,4-difluoronitrobenzene, a yellow liquid, was added. The suspension was then stirred at 80° C. under N₂ overnight (16 h). The now orange solution was cooled to rt, diluted with 100 mL cold 50% brine, and extracted with 3×80 mL EtOAc. The combined organic layers were washed with 5×100 mL sat. NaHCO₃, dried over MgSO₄, and concentrated to yield S13 (3.60 g, 10.87 mmol, 72%) as a yellow oil.

R$_f$=0.40 (10:1 CHCl₃/MeOH, UV); ¹H NMR (500 MHz, CDCl₃): 2.00 (brs, 2H), 3.68 (t, 2H, J=4.5 Hz), 3.71 (m, 2H), 3.77 (m, 4H), 4.21 (t, 2H, J=4.5 Hz), 4.26 (t, 2H, J=4.5 Hz), 6.53 (dd, 1H, J=9.1 Hz, 2.5 Hz), 6.66 (d, 2H, J=2.5 Hz), 7.98 (d, 2H, J=9.1 Hz); ¹³C NMR (151 MHz, CDCl₃): δ 61.83, 61.92, 68.23, 69.33, 69.42, 69.71, 72.83, 72.92, 101.95, 105.94, 128.39, 133.60, 154.96, 163.85; HRMS (ESI): Calculated for C₁₄H₂₁NNaO₈ [M+Na]⁺ 354.1159. found 354.1159.

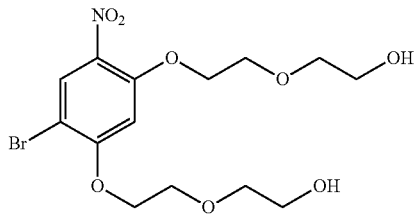 [SMILES: O=[N+]([O-])c1cc(Br)c(OCCOCCO)cc1OCCOCCO]

3.60 g (10.87 mmol) S13, a yellow oil, was dissolved in 22 mL CHCl₃. Next, 1.58 g (11.41 mmol, 1.05 equiv.) K₂CO₃, a white powder, was added. Finally, 0.58 mL (1.82 g, 11.41 mmol, 1.05 equiv.) bromine, a red liquid, was added. The red solution was then stirred in the dark for 2 h. Another 0.1 mL bromine was added at this time and the reaction stirred another 1 h. A significant amount of gummy orange paste collected at the bottom of the flask over the course of this reaction, which was occasionally broken up with a spatula. The reaction was quenched with 50 mL sat. Na₂S₂O₃ solution, then diluted with 50 mL H₂O and extracted with 3×150 mL EtOAc. The combined organic layers were washed with 100 mL sat. Na₂S₂O₃ solution and 5×100 mL sat. NaHCO₃ solution, dried over MgSO₄, and concentrated, yielding S14 (3.27 g, 7.97 mmol, 73%) as a light yellow powder.

R$_f$=0.40 (10:1 CHCl₃/MeOH, UV); ¹H NMR (500 MHz, CDCl₃): 2.07 (brs, 2H), 3.71 (m, 4H), 3.94 (m, 4H), 3.95 (m, 4H), 4.30 (t, 2H, J=4.7 Hz), 4.30 (t, 2H, J=4.7 Hz), 6.78 (s, 1H), 8.22 (s, 1H); ¹³C NMR (151 MHz, CDCl₃): δ 61.74, 61.76, 69.28, 69.31, 69.65, 70.32, 72.83, 72.85, 100.59, 102.72, 130.63, 133.37, 154.24, 160.03; HRMS (ESI): Calculated for C₁₄H₂₀BrNNaO₈ [M+Na]⁺ 432.0264. found 432.0268.

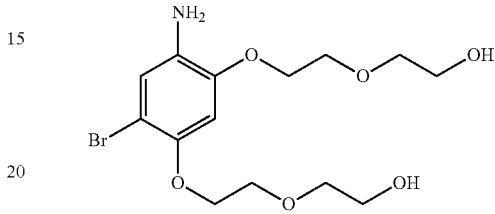

3.27 g (7.97 mmol) S14, a golden oil, was suspended in 16 mL EtOH and 1.6 mL AcOH in a 100 mL round bottom flask. The cloudy solution was heated to 80° C., during which S14 completely dissolved. Finally, 3.12 g (55.79 mmol, 7 equiv.) iron, a grey powder, was added, followed by 0.220 g (1.35 mmol, 0.170 equiv.) FeCl₃, a red-brown solid. A reflux condenser was attached and the grey suspension refluxed for 3 h, cooled to rt, diluted with 50 mL EtOH, and filtered through a pad of Celite. The pad was washed with another 150 mL EtOH. The solution was concentrated and the remaining brown residue purified with flash chromatography using CHCl₃ to 20:1 CHCl₃/MeOH to 7:1 CHCl₃/MeOH to yield S15 (2.07 g, 5.44 mmol, 68%) as a pale brown oil.

R$_f$=0.40 (10:1 CHCl₃/MeOH, UV/I₂); ¹H NMR (500 MHz, CDCl₃): δ 2.93 (brs, 4H), 3.64 (t, 2H, J=4.4 Hz), 3.70 (t, 2H, J=4.6 Hz), 3.75 (t, 2H, J=4.5 Hz), 3.77 (t, 2H, J=4.5 Hz), 3.82 (t, 2H, J=4.6 Hz), 3.86 (t, 2H, J=4.6 Hz), 4.11 (t, 2H, J=4.6 Hz), 4.17 (t, 2H, J=4.4 Hz), 6.64 (s, 1H), 6.92 (s, 1H); ¹³C NMR (151 MHz, CDCl₃): δ 61.95, 62.10, 69.38, 69.82, 70.11, 71.24, 72.99, 73.01, 104.40, 105.19, 119.52, 132.97, 146.54, 148.29; HRMS (ESI): Calculated for C₁₄H₂₃BrNO₆ [M+H]⁺ 380.0703. found 380.0704.

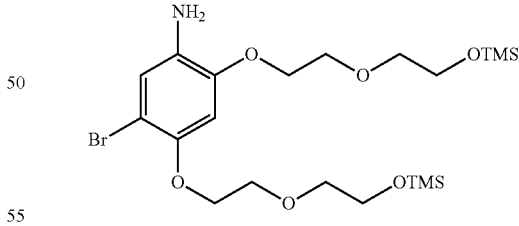

2.07 g (5.44 mmol) S15, a brown oil, was dissolved in 27 mL dry THF in a flame-dried flask. Next, 1.67 mL (1.21 g, 11.97 mmol, 2.2 equiv.) anhydrous triethylamine was added. The solution was cooled to 0° C., then 1.52 mL (1.30 g, 11.97 mmol, 2.2 equiv.) trimethylsilyl chloride was added dropwise, immediately turning the light brown solution to a cloudy slurry. After addition was completed, the reaction was warmed to rt and stirred under N₂ overnight. After 10 h, the cloudy brown solution was filtered to remove salts, then concentrated to afford S16 (2.44 g, 4.65 mmol, 85%) as a brown oil.

¹H NMR (400 MHz, CDCl₃): δ 0.13 (s, 18H), 3.62 (t, 2H, J=5.1 Hz), 3.67 (t, 2H, J=5.2 Hz), 3.75 (t, 2H, J=4.6 Hz), 3.77 (t, 2H, J=4.6 Hz), 3.83 (t, 2H, J=4.6 Hz), 3.84 (t, 2H, J=4.6 Hz), 4.08 (t, 2H, J=4.9 Hz), 4.11 (t, 2H, J=4.9 Hz), 6.57 (s, 1H), 6.89 (s, 1H); ¹³C NMR (151 MHz, CDCl₃): δ -0.29, -0.25, 62.14, 62.22, 69.02, 69.78, 69.98, 71.09, 72.94, 73.08, 103.72, 104.78, 118.98, 132.81, 146.28, 148.05.

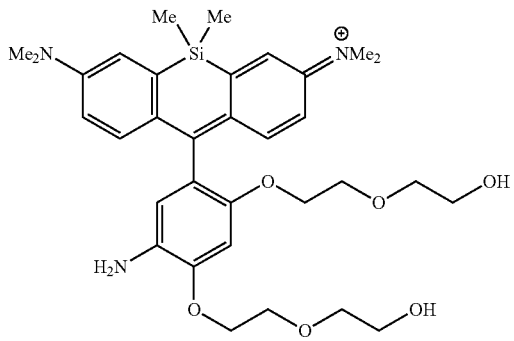

1.05 g (2.00 mmol) S16 was converted to the bis-trimethylsilyl-protected bromoaniline (1.37 g, 2.00 mmol, quant.), a brown oil, via the general procedure.

0.438 g (0.655 mmol) of this intermediate was converted to S17 (0.125 g, 0.194 mmol, 62% based off Si-xanthone), a blue solid, via the general procedure. Chromatography was performed using C₂-functionalized silica gel[8] to minimize loss of material on the column.

¹H NMR (600 MHz, CDCl₃): δ 0.57 (s, 3H), 0.57 (s, 3H), 3.34 (t, 2H, J=4.8 Hz), 3.37 (s, 12H), 3.45 (t, 2H, J=4.9 Hz), 3.53 (t, 2H, J=4.6 Hz), 3.73 (t, 2H, J=4.7 Hz), 3.80 (t, 2H, J=4.3 Hz), 3.95 (t, 2H, J=4.4 Hz), 3.99 (t, 2H, J=4.6 Hz), 4.35 (t, 2H, J=4.5 Hz), 6.65 (s, 1H), 6.73 (dd, 2H, J=9.8 Hz, 2.7 Hz), 6.78 (s, 1H), 7.09 (d, 2H, J=2.8 Hz), 7.38 (d, 2H, J=9.6 Hz); ¹³C NMR (151 MHz, CDCl₃): δ -0.61, -0.56, 41.14, 61.36, 61.63, 69.51, 69.72, 69.88., 69.95, 72.55, 72.88, 101.12, 114.06, 117.78, 120.26, 120.26, 120.85, 128.66, 142.67, 148.14, 148.50, 149.48, 154.18, 169.17; HRMS (ESI): Calculated for C₃₃H₄₆N₃O₆Si [M−Cl]⁺ 608.3150. found 608.3147.

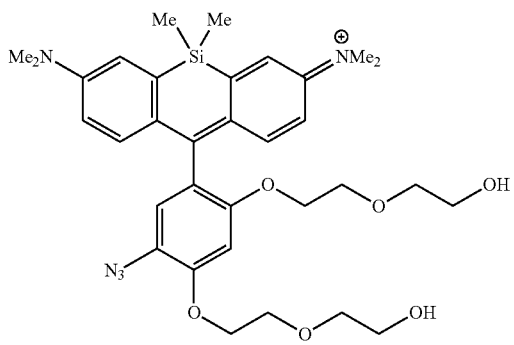

83.8 mg (0.130 mmol) S17 was converted to S18 (68 mg, 0.091 mmol, 70%), a blue solid, via the general procedure. Chromatography was performed using C₂-functionalized silica gel[8] to minimize loss of material on the column.

¹H NMR (600 MHz, CDCl₃): δ 0.56 (s, 3H), 0.59 (s, 3H), 3.35 (t, 2H, J=4.9 Hz), 3.39 (s, 12H), 3.46 (t, 2H, J=5.1 Hz), 3.59 (t, 2H, J=4.5 Hz), 3.97 (t, 2H, J=4.3 Hz), 4.11 (t, 2H, J=4.6 Hz), 3.72 (t, 2H, J=4.5 Hz), 3.80 (t, 2H, J=4.4 Hz), 4.41 (t, 2H, J=4.3 Hz), 6.64 (s, 1H), 6.75 (dd, 2H, J=9.6 Hz, 2.5 Hz), 6.92 (s, 1H), 7.10 (d, 2H, J=2.5 Hz), 7.27 (d, 2H, J=9.6 Hz); ¹³C NMR (151 MHz, CDCl₃): δ -0.84, -0.79, 41.06, 61.19, 61.61, 69.38, 69.38, 69.49, 69.54, 72.62, 72.85, 100.52, 114.12, 120.43, 120.47, 121.27, 121.93, 128.33, 142.04, 148.13, 153.37, 154.12, 154.16, 167.02; HRMS (ESI): Calculated for C₃₃H₄₄N₅O₆Si [M−TFA]⁺ 634.3055. found 634.3054.

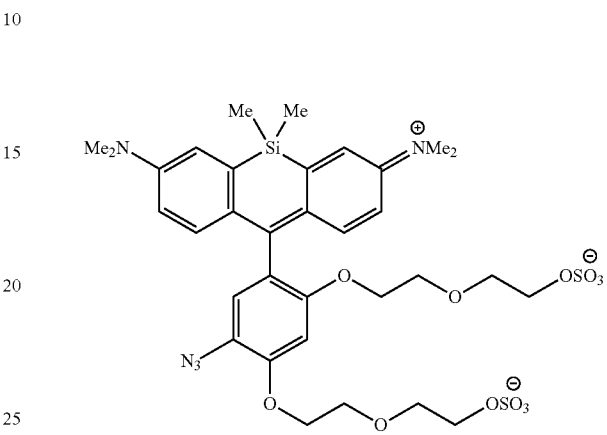

27.6 mg (0.0369 mmol) S18, a blue solid, was dissolved in 0.4 mL dry DMF in a flame-dried flask. Next, 25.8 mg (0.201 mmol, 5 equiv.) SO₃-trimethylamine complex, a white solid, was added. The flask was covered with foil and the blue solution stirred under N₂ overnight (16 h). The solution was then carefully quenched with 3 mL sat. NaHCO₃ and concentrated. The blue residue was taken up in 20 mL MeOH, filtered, and the solution concentrated, yielding a yellow residue. The residue was dissolved in 2 mL H₂O and allowed to sit for 20 min, during which the deep blue color returned. This solution was loaded directly onto the HPLC and purified using a 20-80% MeCN/H₂O gradient on reverse-phase to yield 11 (17.8 mg, 0.0218 mmol, 59%) as a blue solid.

¹H NMR (500 MHz, CD₃OD): δ 0.56 (s, 3H), 0.58 (s, 3H), 3.27 (dd, 2H, J=5.8 Hz, 4.4 Hz), 3.35 (s, 12H), 3.56 (dd, 2H, J=5.0 Hz, 3.2 Hz), 3.63 (dd, 2H, J=5.9 Hz, 4.4 Hz), 3.81-3.85 (m, 2H), 3.93-4.00 (m, 2H), 4.08 (dd, 2H, J=3.1 Hz, 5.1 Hz), 4.11-4.20 (m, 2H), 4.34-4.41 (m, 2H), 6.67 (s, 1H), 6.82 (dd, 2H, J=9.7 Hz, 2.9 Hz), 6.96 (s, 1H), 7.25 (d, 2H, J=9.6 Hz), 7.30 (d, 2H, J=2.9 Hz); ¹³C NMR (151 MHz, CD₃OD): δ -1.22, -0.90, 40.96, 67.81, 68.27, 70.40, 70.72, 70.76, 70.77, 70.86, 70.94, 115.15, 121.95, 121.95, 122.36, 123.44, 129.28, 142.66, 149.13, 154.99, 155.53, 155.66, 167.57; HRMS (ESI): Calculated for C₃₃H₄₂N₅O₁₂S₂Si [M−Na]⁻ 792.2046. found 792.2029.

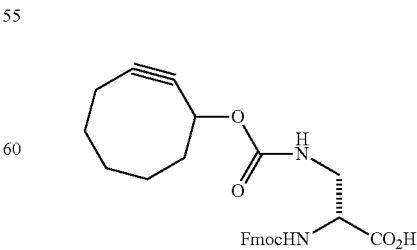

0.675 g (2.07 mmol, 1.3 equiv.) Fmoc-2,3-diaminopropionic acid[9], a brown solid, was dissolved in 45 mL dry DMF.

Next, 0.461 g (1.59 mmol) 2-cyclooctynol p-nitrophenol carbonate[10], a white powder, was added. Finally, 0.67 mL (0.483 g, 4.78 mmol, 3 equiv.) triethylamine, a clear liquid, was added. The now bright yellow solution was stirred for 1.5 h, after which TLC showed consumption of the carbonate. The solution was concentrated and the remaining brown oil taken up in 100 mL EtOAc. 1.5 mL AcOH was added, and the solution was washed with 3×100 mL 50% brine. The organic layer was dried over $Na_2SO_4$ and concentrated, yielding a brown oil. The oil was purified by flash chromatography with $CHCl_3$ to 10:1 $CHCl_3$/MeOH to yield 0.551 g S19, contaminated with p-nitrophenol, as an off-white foamy solid.

Mixture of diastereomers. $R_f$=0.40 (10:1 $CHCl_3$/MeOH, UV/$I_2$); $^1$H NMR (500 MHz, $CD_3OD$): δ 1.44-1.54 (m, 1H), 1.54-1.64 (m, 2H), 1.70-1.80 (m, 1H), 1.81-1.87 (m, 2H), 1.95-2.05 (m, 1H), 2.05-2.25 (m, 2H), 3.40 (dd, 1H (minor), J=13.5 Hz, 7.0 Hz), 3.45 (dd, 1H (major), J=14.0 Hz, 7.5 Hz), 3.56 (dd, 1H (major), J=13.8 Hz, 4.2 Hz), 3.61 (dd, 1H (minor), J=14.0 Hz, 4.3 Hz), 4.21-4.30 (m, 2H), 4.37 (dd, 1H, J=9.8 Hz, 6.9 Hz); 5.15 (app t, 1H, J=12.7 Hz), 7.32 (app t, 2H, J=7.6 Hz), 7.39 (app t, 2H, J=7.5 Hz), 7.68 (d, 2H, J=7.5 Hz), 7.80 (d, 2H, J=7.5 Hz); $^{13}$C NMR (151 MHz, $CD_3OD$): δ 21.01, 27.01 (minor), 27.03 (major), 30.50, 35.05, 42.61, 42.97, 48.07 (major), 48.09 (minor), 55.71, 68.09, 68.25, 91.98 (major), 92.01 (minor), 102.06 (major), 102.09 (minor), 120.74, 126.08, 127.98, 128.58, 142.24, 144.94, 158.08, 158.22, 173.84; HRMS (ESI): Calculated for $C_{27}H_{27}N_2O_6$ $[M+H]^+$ 475.1875. found 475.1866.

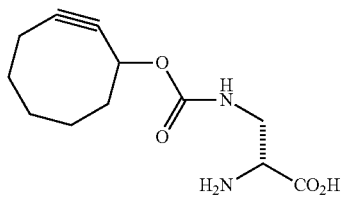

0.139 g of S19 from the previous step, an off-white foamy solid, and 1.16 g 1-2 mmol/g piperazine resin[11] were added to a flame-dried flask and covered with 10 mL dry $CH_2Cl_2$. The yellow suspension was stirred for 5 h, then filtered. The resin was washed with 50 mL $CH_2Cl_2$. Finally, the product was eluted with 150 mL 2:1 $CHCl_3$/MeOH and concentrated. The yellowish residue was dissolved in 50 mL $H_2O$ and washed with 3×50 mL EtOAc. The final wash was extracted with 2×10 mL $H_2O$. The combined aqueous layers were concentrated and lyophilized to yield 12 (46 mg, 0.180 mmol, 45% over two steps) as a white powder. For biological studies, the material was further purified by HPLC using a 5-65% MeCN/$H_2O$ gradient on reverse-phase.

Mixture of diastereomers. $^1$H NMR (500 MHz, $D_2O$): δ 2.93 (brs, 4H), 3.64 (t, 2H, J=4.4 Hz), 3.70 (t, 2H, J=4.6 Hz), 3.75 (t, 2H, J=4.5 Hz), 3.77 (t, 2H, J=4.5 Hz), 3.82 (t, 2H, J=4.6 Hz), 3.86 (t, 2H, J=4.6 Hz), 4.11 (t, 2H, J=4.6 Hz), 4.17 (t, 2H, J=4.4 Hz), 6.64 (s, 1H), 6.92 (s, 1H); $^{13}$C NMR (151 MHz, 1:1 $D_2O/d_6$-DMSO+5% 1M NaOH in $H_2O$): δ 21.24, 26.92, 30.37, 35.06, 42.57, 46.39, 57.01 (minor), 57.06 (major), 68.35, 92.66, 103.79, 158.01, 179.75 (major), 179.79 (minor); HRMS (ESI): Calculated for $C_{12}H_{19}O_4N_2$ $[M+H]^+$ 255.1339. found 255.1340.

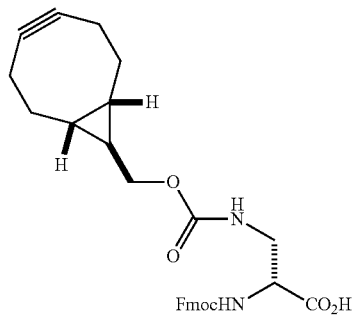

0.864 g (2.65 mmol, 1.3 equiv.) Fmoc-2,3-diaminopropionic acid[9], a light brown solid, was dissolved in 60 mL dry DMF in a flame-dried flask. To this light brown solution was added 0.642 g (2.04 mmol) exo-bicyclononynol p-nitrophenol carbonate[12], a white solid. Finally, 0.85 mL (0.618 g, 6.11 mmol, 3 equiv.) triethylamine, a clear liquid, was added and the yellow solution stirred for 1.5 h, after which all of the carbonate was consumed according to TLC. The solvent was then removed under vacuum and the remaining yellow oil diluted with 100 mL EtOAc. To this solution was added 2 mL AcOH in 100 mL 50% brine. The organic layer was collected, washed with 3×100 mL 50% brine, dried over $Na_2SO_4$, and concentrated to yield a light brown oil. The oil was purified with flash chromatography with $CHCl_3$ to 40:1 $CHCl_3$/MeOH to 10:1 $CHCl_3$/MeOH to yield 0.678 g S20, contaminated with p-nitrophenol, as a white foamy solid.

$R_f$=0.40 (10:1 $CHCl_3$/MeOH, UV/$I_2$); $^1$H NMR (500 MHz, $CD_3OD$): δ 0.57-0.74 (m, 3H), 1.29 (app q, 2H, J=13.0 Hz), 1.97-2.07 (m, 2H), 2.10-2.21 (m, 2H), 2.30 (d, 2H, J=13.4 Hz), 3.43 (dd, 1H, J=13.8 Hz, 8.0 Hz), 3.60 (dd, 1H, J=14.0 Hz, 4.4 Hz), 3.88-3.97 (m, 2H), 4.22-4.30 (m, 2H), 4.36 (dd, 1H, J=7.32 (t, 2H, J=7.9 Hz), 7.39 (t, 2H, J=7.6 Hz), 7.68 (t, 2H, J=6.6 Hz), 7.80 (d, 2H, J=7.7 Hz); $^{13}$C NMR (151 MHz, $CD_3OD$): δ 21.78, 21.79, 23.97, 24.75, 34.21, 43.04, 55.73, 68.18, 70.21, 99.44, 120.89, 126.21, 128.09, 128.70, 142.40, 145.08, 158.38, 159.32, 173.65; HRMS (ESI): Calculated for $C_{29}H_{29}N_2O_6$ $[M+H]^+$ 501.2031. found 501.2019.

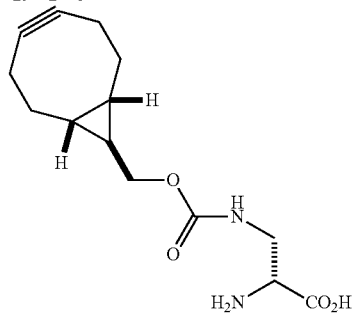

0.149 g S20 from the previous step and 1.16 g 1-2 mmol/g piperazine resin were covered with 10 mL dry $CH_2Cl_2$ in a flame-dried flask.[11] The yellow suspension was stirred for 5 h, then filtered. The resin was washed with 50 mL $CH_2Cl_2$, then the product eluted with 150 mL 2:1 $CHCl_3$/MeOH and concentrated to yield a yellow solid. The solid was then taken up in 50 mL $H_2O$ and washed with 3×50 mL EtOAc, then concentrated and lyophilized to yield 13 (41.5 mg, 0.147 mmol, 34% over two steps) as a white solid. The solid was further purified by HPLC with 5-65% MeCN/$H_2O$ on reverse-phase for biological experiments.

$^1$H NMR (500 MHz, D$_2$O): δ 0.71-0.83 (m, 3H), 1.37 (app q, 2H, J=9.6 Hz), 2.14 (app dt, 2H, J=14.2 Hz, 2.6 Hz), 2.26 (dd, 2H, J=15.8 Hz, 12.4 Hz), 2.39 (dd, 2H, J=13.6 Hz, 2.9 Hz), 3.49 (dd, 1H, J=15.0 Hz, 6.8 Hz), 3.65 (dd, 1H, J=14.9 Hz, 3.9 Hz), 3.78 (dd, 1H, J=6.9 Hz, 3.9 Hz), 3.91-4.12 (m, 2H); $^{13}$C NMR (151 MHz, 1:1 D$_2$O/d$_6$-DMSO+5% 1M NaOH in H$_2$O): 22.18, 23.86, 24.64, 46.44, 57.36, 70.92, 101.57, 159.84, 180.94; HRMS (ESI): Calculated for C$_{14}$H$_{21}$O$_4$N$_2$ [M+H]$^+$ 281.1496. found 281.1498.

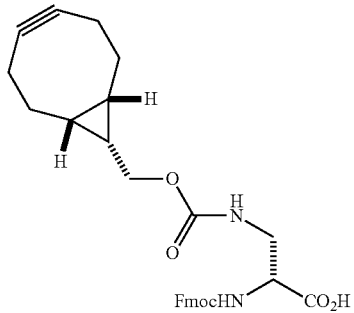

0.849 g (2.60 mmol, 1.3 equiv.) Fmoc-2,3-diaminopropionic acid[9], a light brown solid, was dissolved in 60 mL dry DMF in a flame-dried flask. To this light brown solution was added 0.630 g (2.00 mmol) endo-bicyclononynol p-nitrophenol carbonate[12], a white solid. Finally, 0.84 mL (0.607 g, 6.00 mmol, 3 equiv.) triethylamine, a clear liquid, was added and the yellow solution stirred for 1.5 h, after which all of the carbonate was consumed according to TLC. The solvent was then removed under vacuum and the remaining yellow oil diluted with 100 mL EtOAc. To this solution was added 2 mL AcOH in 100 mL 50% brine. The organic layer was collected, washed with 3×100 mL 50% brine, dried over Na$_2$SO$_4$, and concentrated to yield a light brown oil. The oil was purified by flash chromatography with CHCl$_3$ to 40:1 CHCl$_3$/MeOH to 20:1 CHCl$_3$/MeOH to 10:1 CHCl$_3$/MeOH to yield 0.782 g S21, contaminated with p-nitrophenol, as a white foamy solid.

R$_f$=0.40 (10:1 CHCl$_3$/MeOH, UV/I$_2$); $^1$H NMR (600 MHz, CD$_3$OD): δ 0.80-0.95 (m, 2H), 1.28-1.32 (m, 1H), 1.41-1.63 (m, 2H), 2.02-2.25 (m, 6H), 3.44 (dd, 1H, J=14.1 Hz, 8.2 Hz), 3.61 (dd, 1H, J=14.4 Hz, 4.8 Hz), 4.04 (dd, 1H, J=11.4 Hz, 8.4 Hz), 4.07-4.17 (m, 2H), 4.20-4.40 (m, 3H), 7.31 (app t, 2H, J=8.0 Hz), 7.38 (app t, 2H, J=8.2 Hz), 7.57-7.72 (m, 2H), 7.80 (d, 2H, J=7.7 Hz); 13C NMR (125 MHz, CD$_3$OD): δ 18.78, 21.33, 21.87, 30.04, 43.16, 55.89, 64.01, 68.23, 99.50, 120.92, 126.25, 128.14, 128.76, 142.51, 145.16, 158.47, 159.42, 173.79; HRMS (ESI): Calculated for C$_{29}$H$_{29}$N$_2$O$_6$ [M+H]$^+$ 501.2031. found 501.2021.

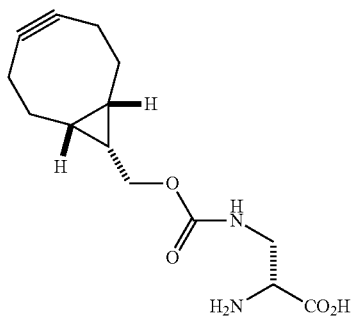

0.270 g of S21 from the previous step, a white foamy solid, and 2.15 g 1-2 mmol/g piperazine resin[11] were added to a flame-dried flask and covered with 18 mL dry CH$_2$Cl$_2$. The now yellow solution was stirred for 5 h. The mixture was then filtered and washed with 100 mL CH$_2$Cl$_2$. The product was then eluted with 150 mL 2:1 CHCl$_3$/MeOH, then concentrated. The solid was then taken up in 80 mL H$_2$O and washed with 3×80 mL EtOAc, then concentrated and lyophilized to yield 14 (78.4 mg, 0.280 mmol, 41% over two steps) as a white solid. The solid was further purified by HPLC with 5-65% MeCN/H$_2$O on reverse-phase for biological experiments.

$^1$H NMR (500 MHz, D$_2$O): δ 0.98 (t, 2H, J=9.4 Hz), 1.40 (t, 1H, J=8.7 Hz), 1.53-1.61 (m, 2H), 2.19-2.31 (m, 6H), 3.54 (dd, 1H, J=15.1 Hz, 6.9 Hz), 3.70 (d, 1H, J=15.2 Hz), 3.85 (dd, 1H, J=7.0 Hz, 3.7 Hz), 4.20 (d, 2H, J=8.8 Hz); $^{13}$C NMR (151 MHz, 1:1 D$_2$O/d$_6$-DMSO DMSO+5% 1M NaOH in H$_2$O): 18.71, 21.10, 22.22, 46.52, 57.33, 64.43, 101.28, 159.51, 180.42; HRMS (ESI): Calculated for C$_{14}$H$_{21}$O$_4$N$_2$ [M+H]$^+$ 281.1496. found 281.1492.

Fluorescein, Rhodamine and Si-Fluorescein Derivatives

Figure 28:
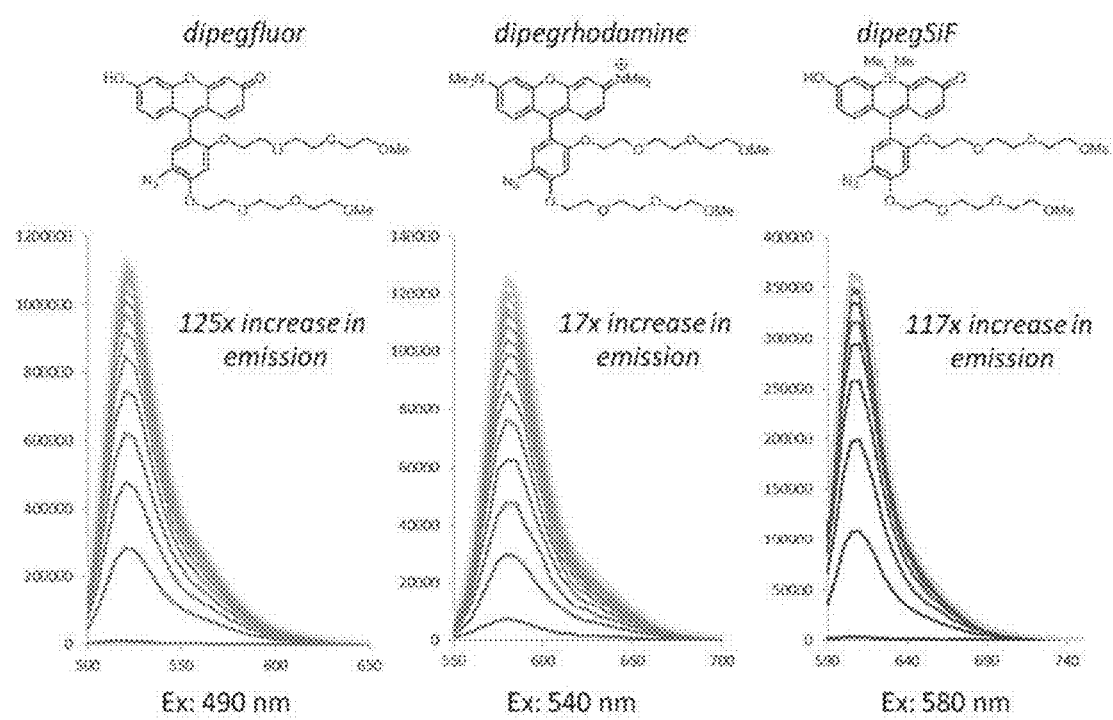
FIG. 28 shows graphs of fluorescence enhancement (emission, a.u.) vs. excitation wavelength (nm) for di-PEG-fluorescein, di-PEG-rhodamine, and di-PEG-Si-fluorescein, according to embodiments of the present disclosure.
Figure 29:
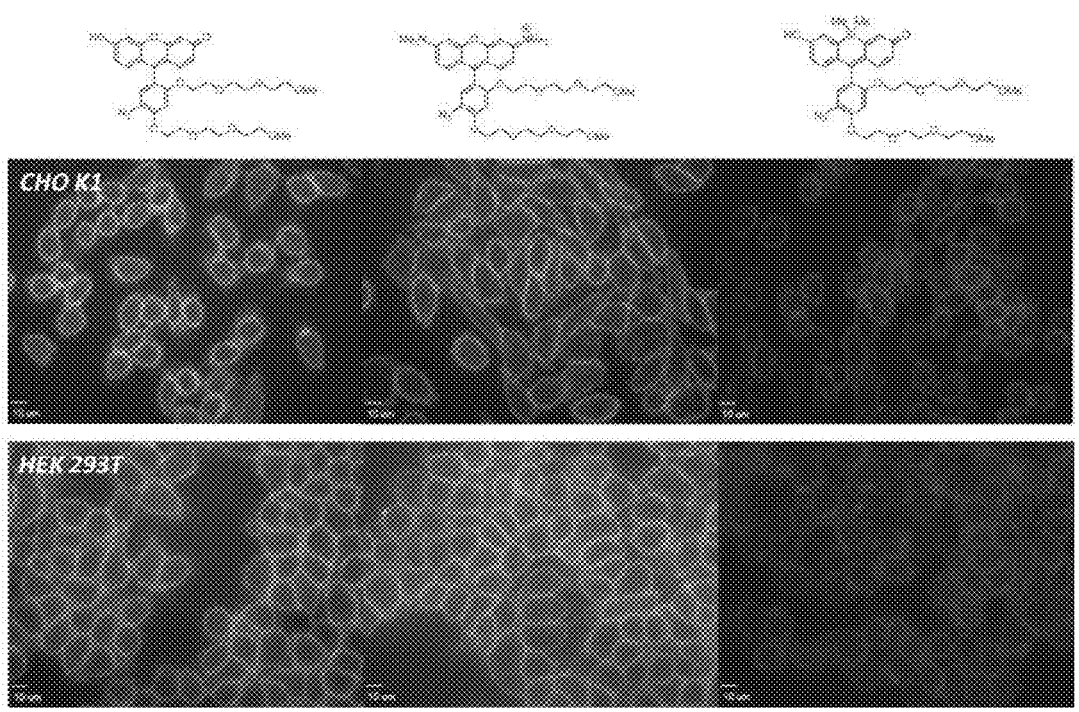
FIG. 29 shows fluorescence images of labeling of CHO K1 and HEK 293T cells with di-PEG-fluorescein, di-PEG-rhodamine, and di-PEG-Si-fluorescein, according to embodiments of the present disclosure.

Experiments were performed to test the pendant aryl ring ability to efficiently switch fluorescence in a variety of xanthene fluorophores, such as fluorescein, rhodamines, and Si-fluoresceins. (FIG. 28) The fluorescence enhancement of the fluorescein and Si-fluorescein derivatives upon triazole formation was larger than that of our Si-rhodamine derivative. These analogs were all suitable for the no-wash detection of alkyne-functionalized sialic acids on cell surface glycoproteins. (FIG. 29) These probes, all rendered highly fluorogenic by the same pendant aryl ring, may find use in multicolor imaging experiments or in experiments requiring fluorophores of a certain excitation/emission wavelength.

Generality of the 2,4-Dialkoxy-5-Azido Group

To a 1 cm×0.4 cm quartz cuvette was added 944 μL PBS. Next, 2 μL 50 mM BTTAA in PBS and 1 μL 50 mM CuSO$_4$ in H$_2$O were added and the solution mixed with a pipette. Next, 50 μL freshly prepared 100 mM sodium ascorbate in PBS was added and the solution mixed again. Then, 2 μL 1 mM azido fluorophore in 4:1 PBS/MeOH was added and the solution mixed. The emission spectra were recorded at this time (t=0 s). Finally, 1 μL 100 mM alkyne in DMSO was added and the solution vigorously mixed and monitored every 30 s for 10 min. Final concentrations for all reagents are 2 μM azido fluorophore, 100 μM alkyne, 100 μM BTTAA, 50 μM CuSO$_4$, and 5 mM sodium ascorbate with a total volume of 1 mL. Fluorescence spectra were recorded on a Photon Technology International Quanta Master 4 L-format scanning spectrofluorometer equipped with an LPS-220B 75-W xenon lamp and power supply, A-1010B lamp housing with an integrated igniter, switchable 814 photon counting/analog photomultiplier detection unit, and MD5020 motor driver. See FIG. 28.

Mammalian Cell Surface Labeling with 2,4-Dialkoxy-5-Azido Substituted Fluorophores Cells were grown in 8-well Lab-Tek Chambered Coverglass systems in media (HAM-F12 for CHO K1 cells, DMEM for HEK 293T cells) containing 10% fetal bovine serum, penicillin/streptomycin, and 50 μM Ac$_4$ManNAl for 3 d at 37° C. The cells were then washed with 3×300 μL PBS, then incubated with 100 μL freshly prepared click solution. Click solution comprised of 50 μM CuSO$_4$, 300 μM BTTAA, 2.5 mM sodium ascorbate, and 5 μM azido fluorophore. This was prepared by first adding 0.5 μL 50 mM CuSO$_4$ in H$_2$O and 3 μL 50 mM BTTAA in H$_2$O to 481.5 μL PBS. Next, 12.5 μL freshly prepared 100 mM sodium ascorbate in PBS was added. Finally, 2.5 μL 1 mM azido fluorophore in 4:1 PBS/

MeOH was added. After 15 min, the reactions were quenched with the addition of 1 μL of 100 mM bathocuproine disulfonate (BCS) in $H_2O$ (final concentration 1 mM). Microscopy was performed using a Zeiss AxioVert 200M inverted microscope using a Plan-Neofluar 40×/0.75 objective. Exposure time was 1000 ms using the FITC, Cy3, or Cy5 filters. Images were acquired and processed using SlideBook 5.0, and are shown as a single z-plane. See FIG. 29.

Example 2

CalFluors

A Universal Motif for Fluorogenic Azide Probes Across the Visible Spectrum

A universal switch capable of PeT across a variety of dye structures was identified for use in activatable azide probes with various photophysical and photochemical properties. It is demonstrated herein that the 3-azido 4,6-dialkoxyaryl group possesses this capability. Incorporation of this group into various xanthene scaffolds provided a palette of dyes that emit at green to near-infrared (NIR) wavelengths. When functionalized with water solubilizing groups, these probes provided robust and sensitive detection of alkyne-labeled biomolecules under no-wash conditions and in a variety of settings, including live cells and tissue sections. The probes are referred to as Click Activated Luminogenic Fluorophores, or CalFluors.

Results

The 3-azido-4,6-dimethoxy benzene substituent was identified as a fluorogenic switch that outperformed many other aryl substituents examined. To further investigate the electronic basis of this superior performance, a panel of azide- and triazole-functionalized aryl rings was synthesized (3-7, FIG. 31A) and their redox potentials were determined using cyclic voltammetry (FIG. 31B). The measured oxidation potentials reflect the compounds' propensity to donate an electron, which would result in fluorescence quenching via PeT. Consistent with calculations, it was found that all the triazoles had higher oxidation potentials than their parent azides (FIG. 31C). Among the aryl azides, compound 3a was the most electron rich, underscoring its potent quenching activity, and its change in oxidation potential upon conversion to triazole 3b was the most dramatic (FIG. 2D). This large change is consistent with computational predictions that an ortho-substituent forces the triazole to twist further out of plane and prevents donation from the nitrogen lone pair into the aryl system. It was found that calculated $E_{HOMO}$ and oxidation potential correlate, though the modest fit suggests that more sophisticated approaches towards predicting PeT efficiency may be necessary for future improvements in computation-based probe design. Nevertheless, these results indicated that dimethoxy aryl ring 3 would efficiently switch fluorescence in a variety of fluorophore systems, regardless of subtle differences in their electronics.

FIG. 31: Cyclic voltammetry analysis of substituted aryl systems. (A) Aryl azides (3a-7a) and triazoles (3b-7b) synthesized and studied by cyclic voltammetry. (B) Cyclic voltammetry plots of compounds 3-7. (C) Oxidation potentials of compounds 3-7. Note that all redox cycles were completely or partially irreversible. Cyclic voltammetry was performed in acetonitrile containing 0.1 M $NBu_4PF_6$ as an electrolyte using platinum and glassy carbon electrodes, with a silver reference standard. Ferrocene was added afterwards as an internal standard. Scans were performed at 100 mV/s from 0 to 2 V.

A panel of xanthene fluorophores containing the 3-azido 2,4-dimethoxy benzene substituent were investigated. Fluorescein, tetramethylrhodamine (rhodamine) and dimethylsilicon-substituted fluorescein (Si-fluorescein) scaffolds, which have emission maxima of around 520 nm (green, compound 8), 580 nm (orange, compound 9) and 610 nm (red, compound 10), respectively (FIG. 32A), were investigated. Following a general route, 3-bromo-4,6-dimethoxy aniline was protected, lithiated, and then added into various protected xanthones to generate the corresponding amino-fluorescein, -rhodamine, and -Si-fluorescein derivatives. While the fluorescein and Si-fluorescein xanthones were readily prepared via literature procedures, a new route was developed to access the rhodamine xanthone from commercially available Pyronin Y. These amine-functionalized probes were converted to aryl azides by diazotization and displacement with sodium azide to generate compounds 8a to 10a. The corresponding triazoles, 8b to 10b, were prepared under Cu-catalyzed click conditions.

The fluorescence quantum yields of the azides and triazole products were measured in pH 7.4 phosphate-buffered saline. It was found that their common dimethoxy aryl substituent efficiently switched fluorescence for all fluorophores tested (Table 2). Notably, the fluorescein and Si-fluorescein probes offered higher levels of fluorescence enhancement. In particular, Si-fluorescein 10a, which has an emission maximum beyond 600 nm, underwent >100-fold enhancement in fluorescence upon click reaction. Rhodamine 9a, however, showed a significantly lower turn-on ratio (20-fold) due to reduced quenching of the azide starting material. All of the probes were good substrates for the Cu-catalyzed click reaction, achieving complete conversion to the corresponding triazoles within 10 min using micromolar concentrations of catalyst and reagents.

FIG. 32: Structures of fluorophores prepared in this study. (A) Parent dimethoxy-substituted fluorophores 8 to 10. (B) Oligoethylene-glycol functionalized fluorescein derivative 11.

TABLE 2

Photophysical properties of fluorophores of interest. Measurements were made in pH 7.4 phosphate-buffered saline.

| Compound | $\lambda_{max}$ | $\lambda_{em}$ | $\Phi_{fl}$ | Enhancement |
| --- | --- | --- | --- | --- |
| 8a | 497 nm | 516 nm | 0.0059 | — |
| 8b | 498 nm | 520 nm | 0.437 | 74x |
| 9a | 555 nm | 577 nm | 0.0178 | — |
| 9b | 557 nm | 580 nm | 0.351 | 20x |
| 10a | 586 nm | 604 nm | 0.00136 | — |
| 10b | 588 nm | 604 nm | 0.240 | 176x |
| 2 | 654 nm$^a$ | 666 nm$^a$ | 0.0042$^a$ | — |
| 2 triazole | 665 nm$^a$ | 668 nm$^a$ | 0.20$^a$ | 48x$^a$ |
| 11a | 499 nm | 519 nm | 0.00589 | — |
| 11b | 499 nm | 520 nm | 0.743 | 126x |
| CalFluor 488 | 498 nm | 520 nm | 0.00306 | — |
| CalFluor 488 triazole | 500 nm | 521 nm | 0.0747 | 243x |
| CalFluor 555 | 557 nm | 577 nm | 0.0174 | — |
| CalFluor 555 triazole | 561 nm | 583 nm | 0.604 | 35x |
| CalFluor 580 | 588 nm | 611 nm | 0.00250 | — |
| CalFluor 580 triazole | 591 nm | 609 nm | 0.473 | 189x |
| CalFluor 647 | 655 nm | 678 nm | 0.0056 | — |
| CalFluor 647 triazole | 657 nm | 674 nm | 0.25 | 45x |

$^a$Data from Shieh et al., Proc. Natl. Acad. Sci. 2014, 111, 5456-5461.

A significant advantage of these probes is that, by replacing the methoxy groups with other alkyloxy functionalities, their physical properties can be altered without perturbing the electronics of the system. It was found that introducing oligoethylene glycol tails significantly improved the water solubility of our probes while maintaining fluorescence enhancement. The bis-oligoethylene glycol functionalized azidofluorescein derivative 11a as well as its triazole derivative 11b (FIG. 32B) were synthesized. This fluorescein analogue maintained the enhancement in fluorescence of the parent fluorophore while showing good water solubility, making it very well-suited for biological labeling experiments (Table 2).

The robustness of this route provided access to oligoethylene glycol functionalized rhodamine and Si-fluorescein probes as well. Water solubility of the Si-rhodamine derivative was improved by adding sulfate esters at the termini of oligoethylene glycol chains In a search for alternative solubilizing groups, zwitterions were considered, which find use in anti-fouling agents in biomaterials applications. In some cases, zwitterionic coatings have been shown to outperform polyethylene glycols. Additionally, in some cases, zwitterionic fluorophores have been demonstrated to have reduced serum binding compared to anionic counterparts. To generate fluorophores containing zwitterionic tails, the sulfo-betaine scaffold, which can be generated by the reaction of tertiary amines with 1,3-propanesultone, was investigated. The mild reaction conditions suggested that these functionalities could be introduced at the end of our synthetic route, thereby minimizing difficulties in product isolation. Accordingly, a panel of zwitterionic azide fluorophores was prepared (named CalFluor 488, 555, 580 and 647, respectively, where the numbers represent their excitation wavelengths) (FIG. 33A).

All the CalFluors underwent significant fluorescence enhancement upon triazole formation at a level that was at least as high as their dimethoxy substituted counterparts (FIG. 33B, Table 2). CalFluor 488 and 580 showed higher levels of fluorescence enhancement compared to their parent derivatives, potentially due to subtle electronic differences conferred by the oligoethylene glycol tails. Additionally, the fluorescence of these probes remained virtually unaltered in proteinaceous environments (e.g., 3% BSA or neat fetal bovine serum) or in the presence of detergents such as Triton X-100 and Tween-20, demonstrating how effectively these zwitterionic tails minimize non-specific interactions.

FIG. 33: CalFluors and their fluorescence enhancements. (A) Structures of CalFluors 488, 555, 580, and 647. (B) Fluorescence enhancements of CalFluors during copper-catalyzed click reactions. To a mixture of 2 µM fluorophore, 50 µM, 300 µM BTTAA ligand, and 2.5 mM sodium ascorbate was added 100 µM alkyne and emission scans were taken every 30 seconds. The first scan was taken immediately before addition of alkyne.

The CalFluors' performance in no-wash cell imaging experiments was evaluated. Using established methods, cell-surface glycoconjugates were metabolically labeled with peracetylated N-pentynoyl mannosamine ($Ac_4ManNAl$), which introduces terminal alkyne groups into sialic acid residues (SiaNAl). HEK 293T cells treated in this fashion were then incubated, without fixation, with a cocktail containing 50 µM $CuSO_4$, 300 µM BTTAA, 5 mM sodium ascorbate and 10 µM CalFluor dye. After 15 min, cell surface glycans were robustly labeled with the given fluorophore, whereas control cells treated with peracetylated N-acetylmannosamine ($Ac_4ManNAc$) showed no detectable fluorescence (FIG. 34A). The only background fluorescence was from free fluorophore in solution (only observable at high contrast). Similar results were achieved with CHO K1 cells. Labeling with CalFluor probes could be observed in real time and clear fluorescence over background was visible just minutes into the reaction. Notably, under the same reaction conditions, CalFluors labeled cells far more intensely than the blue fluorogenic probe 3-azido-7-hydroxycoumarin, which is attributed in part to the CalFluors' superior reactivity. This observation is consistent with studies by Finn and coworkers showing that electron-rich aryl azides undergo more rapid copper-catalyzed click reactions.

FIG. 34: No-wash labeling of cell-surface glycoproteins on HEK 293T cells. Cells were grown with 50 µM $Ac_4ManNAl$ or $Ac_4ManNAc$ for 3 days, then subjected to click labeling with CalFluor probes. (A) Labeling glycoproteins on live cell surfaces. Cells were treated with 10 µM azide probe, 50 µM $CuSO_4$, 300 µM BTTAA ligand, and 5 mM sodium ascorbate. The reaction was quenched with 1 mM BCS and the cells imaged without further wash steps. (B) Labeling glycoproteins on fixed cells. Cells were fixed with 3% paraformaldehyde, then treated with 10 µM CalFluor probe, 1 mM $CuSO_4$, 100 µM TBTA ligand, and 2 mM sodium ascorbate. 0.1 mg/mL BSA was added to prevent the TBTA from precipitating over the course of the reaction.

Fixed (3% paraformaldehyde) $Ac_4ManNAl$-treated HEK 293T cells were also evaluated as substrates CalFluor labeling. In this case, copper-click reaction with 50 µM $CuSO_4$ and 300 µM BTTAA gave poor labeling, potentially due to sequestration of the copper catalyst by denatured proteins. However, use of higher catalyst concentrations (100 µM TBTA, 1 mM $CuSO_4$, 2 mM sodium ascorbate) gave robust labeling with 10 µM CalFluor dyes (FIG. 34B). While some background was apparent when using CalFluor 555 at this concentration, a single wash step was sufficient to eliminate this background fluorescence. Similar results were achieved when performing the same experiments on fixed CHO K1 cells.

Under these copper-click conditions, the 3-azido-7-hydroxycoumarin probe performed comparably to the CalFluors when labeling fixed cells. By contrast, the sulfated predecessor S1 or the oligoethylene glycol containing probe 11 gave higher background fluorescence, underscoring the benefit of the zwitterionic tails in reducing non-specific interactions. The advantage of the fluorescence turn-on of CalFluors was clear when comparing labeling by the non-fluorogenic AlexaFluor 647 alkyl azide. Even with a washing step, background from unreacted fluorophore obscured any alkyne-dependent signal.

The probes were tested for visualization of glycans in vivo. Zebrafish have been powerful model system for the study of development using optical methods due to their optical transparency. To test the utility of CalFluors in this system for such applications, zebrafish embryos at the single-cell stage were injected with SiaNAl. After either 24 or 36 hours post fertilization (hpf), the embryos were bathed in a solution containing a CalFluor probe along with copper catalyst. Bright alkyne-dependent fluorescence was observed on cells of the enveloping layer without washing (FIG. 35A). Fluorescence signal increased over time and maximized after 20 minutes. Importantly, in similar labeling experiments performed with the non-fluorogenic AlexaFluor 594 alkyl azide probe or the blue-emitting 3-azido-7-hydroxycoumarin (FIG. 35B), high levels of background fluorescence from unreacted probe or endogenous biomolecules, respectively, obscured alkyne-dependent labeling.

FIG. 35: Visualizing sialic acids in developing zebrafish with CalFluors. Zebrafish were injected with 50 pmol SiaNAl at the one to four-cell stage and allowed to develop over time. (A) Real-time labeling of sialic acids. After 24 hpf, zebrafish were incubated in a solution containing 1 µM CalFluor 580 and copper catalyst. Alkyne-dependent labeling was observable after 5 minutes, and appeared to saturate at 20 minutes. Scale bar=500 µm. (B) Comparing no-wash labeling performance by azide probes. After 36 hpf, the embryos were transferred to a solution containing the fluorophore (1 μM for CalFluor 580 and AlexaFluor 594 alkyl azide, or 5 μM for 3-azido-7-hydroxycoumarin) and copper catalyst and imaged without washing after 20 minutes. Only zebrafish labeled with CalFluor 580 show alkyne-dependent fluorescence signal. Scale bar=100 μm.

The suitability of the probes for imaging EdU-labeled DNA was tested. HEK 293T cells were treated with 10 μM EdU for 12 h, fixed and permeabilized, then labeled with azide probes under copper-click conditions. The use of fluorogenic azide probes for EdU detection would streamline the visualization of newly synthesized DNA. Robust labeling was observed using all four of the probes without the need to wash away excess reagent (FIGS. 36A, 36B). Results were significantly better than those achieved using other azide fluorophores under similar labeling conditions. (FIG. 36B). The fluorescein-based probes (CalFluors 488 and 580) labeled intracellular DNA more weakly than the related rhodamine-based probes (CalFluors 555 and 647, FIG. 35B). Similar results were achieved when newly synthesized RNA was labeled by treatment of cells with 1 mM EU. This difference could be attributed to electrostatic interactions that are favorable for the cationic rhodamines but unfavorable for the anionic fluoresceins.

The palette of probes provided two-color imaging with other well established probes, such as with cells pre-labeled with the blue-emitting Hoescht 33342 nuclear stain (FIG. 36C). No-wash labeling was also suitable for CHO K1 cells labeled with EdU and EU under identical conditions, although specific signal was lower for all probes tested, likely due to poorer alkyne incorporation. Beyond imaging mammalian cells in culture, EdU has also been used to label newly synthesized DNA in bacteria. *E. coli* were grown in the presence of EdU, fixed, permeabilized, and labeled with CalFluor 647; robust alkyne-dependent labeling was observed by flow cytometry, and significantly higher signal over background was achieved compared to AlexaFluor 647 alkyl azide. One possible application of EdU labeling is to visualize actively proliferating cells in vivo. Tissue slices were obtained from the subventricular zone of mice injected with 150 mg/kg EdU two hours before perfusion. CalFluor 647 were able to efficiently visualize EdU from these tissue sections with excellent signal over background (FIG. 36D). Finally, all four CalFluor probes were suitable for the robust detection of newly synthesized proteins containing HPG.

FIG. 36: Visualizing EdU-labeled DNA using fluorogenic azide probes. (A) No-wash labeling of EdU-labeled HEK 293T cells. Cells were treated with EdU for 16 h, fixed and permeabilized, then treated with 10 μM CalFluor probe, 1 mM $CuSO_4$, 100 μM TBTA ligand, 2 mM sodium ascorbate, and 0.1 mg/mL BSA and imaged without further wash steps after 1 hour. (B) Quantification of normalized signal over background for the four panels in (A), and comparison to labeling under identical conditions using the non-fluorogenic AlexaFluor 647 alkyl azide (AF). (C) Two-color labeling using Hoescht 33342 and CalFluor 555. After staining with Hoescht, the cells were incubated with a solution of 1 μM CalFluor probe and copper catalyst and imaged in real-time. (D) Visualization of EdU-labeled newly proliferating cells in mouse brain slices with CalFluor 647.

CONCLUSION

A general platform to generate fluorogenic azide probes across the visible spectrum is reported. The experiments demonstrate the broad applicability of these optimized probes for labeling a large panel of alkyne-functionalized biomolecules in both live and fixed cells, in tissue and in vivo. Given the generality of PeT, the bis-zwitterionic dialkoxy aryl azide motif switches fluorescence in a wide variety of fluorophores beyond the xanthenes. For example, other fluorophore scaffolds, such as BODIPY, cyanines, and pyrazolines, can all be efficiently switched via PeT. Using an optimized aryl ring in conjunction with cyanine probes or modified Si-rhodamine probes may push emission maxima further into the near-infrared. PeT has also been used to modulate other properties besides fluorescence, such as the rate of singlet oxygen generation or luminescence from metal complexes. This transportable design element is integrated into myriad dye scaffolds. In addition, the incorporation of zwitterionic sulfobetaine tails, which outperformed both oligoethylene glycol or sulfated modifications in some cases, may be used in a variety of PeT-based probes in complex environments.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of any one of formulae (II), (IV) and (V):

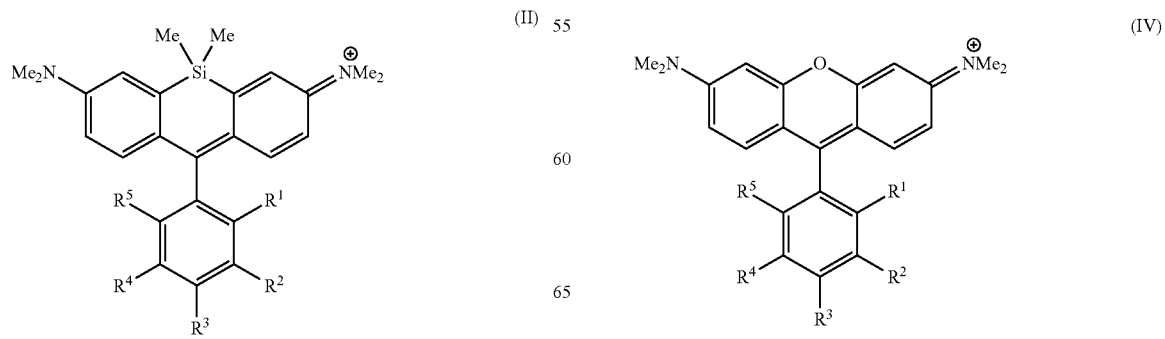

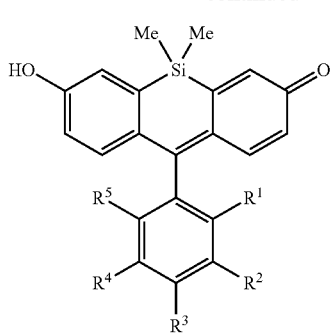

wherein
$R^1$, $R^2$, $R^3$, $R^4$ and $R^5$ are each independently selected from the group consisting of hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl;
optionally, one of $R^1$, $R^2$, $R^3$, $R^4$ or $R^5$ together with its adjacent R-group form a cycloalkyl, substituted cycloalkyl, heterocycloalkyl, substituted heterocycloalkyl, aryl, substituted aryl, heteroaryl or substituted heteroaryl; and
one of $R^1$, $R^2$, $R^3$, $R^4$ or $R^5$ is azido and one of $R^1$, $R^2$, $R^3$, $R^4$ or $R^5$ is optionally a molecule of interest.

2. The compound of claim 1, wherein $R^1$, $R^2$, $R^3$, $R^4$ and $R^5$ are each independently selected from the group consisting of hydrogen, alkyl, substituted alkyl, alkoxy, substituted alkoxy, azido, amino, substituted amino, cycloalkyl, substituted cycloalkyl, heterocycloalkyl, substituted heterocycloalkyl, aryl, substituted aryl, heteroaryl, and substituted heteroaryl.

3. The compound of claim 1, wherein $R^1$, $R^2$, $R^3$, $R^4$ and $R^5$ are each independently selected from the group consisting of hydrogen, alkyl, substituted alkyl, alkoxy, substituted alkoxy, azido, heterocycloalkyl, and substituted heterocycloalkyl.

4. The compound of claim 1, wherein one of $R^1$, $R^2$, $R^3$, $R^4$ or $R^5$ together with its adjacent R-group form a cycloalkyl, substituted cycloalkyl, heterocycloalkyl, substituted heterocycloalkyl, aryl, substituted aryl, heteroaryl or substituted heteroaryl.

5. The compound of claim 1, wherein $R^1$ and $R^2$ together form a cycloalkyl, substituted cycloalkyl, heterocycloalkyl, substituted heterocycloalkyl, aryl, substituted aryl, heteroaryl or substituted heteroaryl.

6. The compound of claim 1, wherein $R^3$ is azido.

7. The compound of claim 1, wherein $R^4$ is azido.

8. The compound of claim 1, wherein two of $R^1$, $R^2$, $R^3$, $R^4$ and $R^5$ are hydrogen, one of $R^1$, $R^2$, $R^3$, $R^4$ or $R^5$ is azido, and one of $R^1$, $R^2$, $R^3$, $R^4$ or $R^5$ together with its adjacent R-group form a cycloalkyl, substituted cycloalkyl, heterocycloalkyl, substituted heterocycloalkyl, aryl, substituted aryl, heteroaryl or substituted heteroaryl.

9. The compound of claim 1, wherein three of $R^1$, $R^2$, $R^3$, $R^4$ and $R^5$ are hydrogen, one of $R^1$, $R^2$, $R^3$, $R^4$ or $R^5$ is azido, and one of $R^1$, $R^2$, $R^3$, $R^4$ and $R^5$ is alkyl, substituted alkyl, alkoxy, substituted alkoxy, heterocycloalkyl, or substituted heterocycloalkyl.

10. The compound of claim 1, wherein two of $R^1$, $R^2$, $R^3$, $R^4$ and $R^5$ are hydrogen, one of $R^1$, $R^2$, $R^3$, $R^4$ or $R^5$ is azido, and two of $R^1$, $R^2$, $R^3$, $R^4$ and $R^5$ are independently selected from alkyl, substituted alkyl, alkoxy, substituted alkoxy, heterocycloalkyl, and substituted heterocycloalkyl.

11. A compound of formula (II):

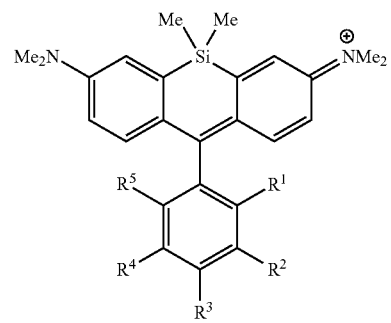

wherein:
$R^1$ is —$OR^{12}$;
$R^3$ is —$OR^{11}$;
$R^4$ is azido;
$R^2$ and $R^5$ are H; and
$R^{11}$ and $R^{12}$ are each independently hydrogen, an alkyl, a substituted alkyl, a PEG, a zwitterionic group or a water solubilizing group (WSG).

12. A compound of formula (III):

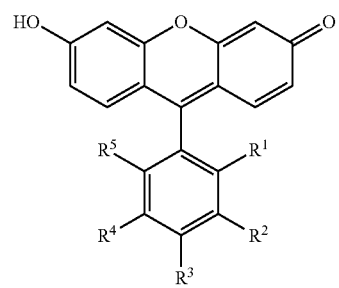

wherein:
$R^1$ is —$OR^{12}$;
$R^3$ is —$OR^{11}$;
$R^4$ is azido;
$R^2$ and $R^5$ are H; and
$R^{11}$ and $R^{12}$ are each independently hydrogen, an alkyl, a substituted alkyl, a PEG, a zwitterionic group or a water solubilizing group (WSG).

13. A compound of formula (IV):

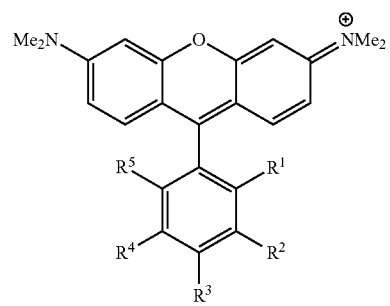

wherein:
R$^1$ is —OR$^{12}$;
R$^3$ is —OR$^{11}$;
R$^4$ is azido;
R$^2$ and R$^5$ are H; and
R$^{11}$ and R$^{12}$ are each independently hydrogen, an alkyl, a substituted alkyl, a PEG, a zwitterionic group or a water solubilizing group (WSG).

14. A compound of formula (V):

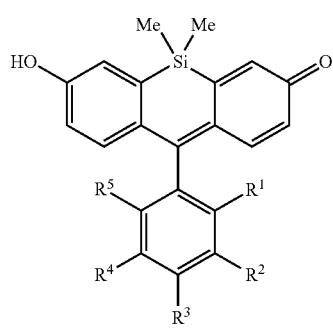

(V)

wherein:
R$^1$ is —OR$^{12}$;
R$^3$ is —OR$^{11}$;
R$^4$ is azido;
R$^2$ and R$^5$ are H; and
R$^{11}$ and R$^{12}$ are each independently hydrogen, an alkyl, a substituted alkyl, a PEG, a zwitterionic group or a water solubilizing group (WSG).

15. A method of labeling a target biomolecule comprising an alkyne, the method comprising contacting the biomolecule with a compound selected from:
(a) a compound of any one of formulae (II), (IV) and (V),

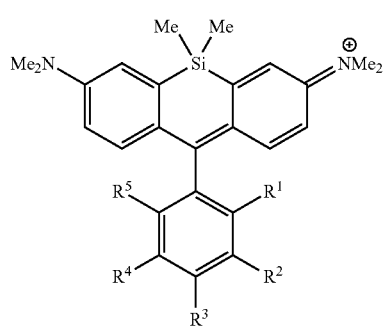

(II)

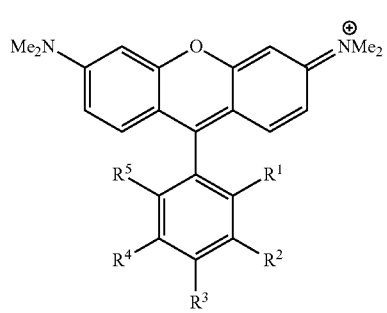

(IV)

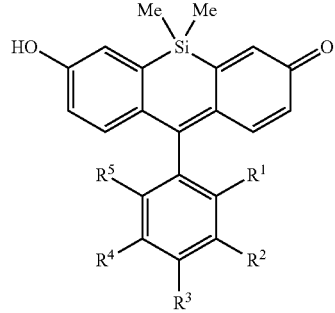

(V)

wherein R$^1$, R$^2$, R$^3$, R$^4$ and R$^5$ are each independently selected from the group consisting of hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl;
optionally, one of R$^1$, R$^2$, R$^3$, R$^4$ or R$^5$ together with its adjacent R-group form a cycloalkyl, substituted cycloalkyl, heterocycloalkyl, substituted heterocycloalkyl, aryl, substituted aryl, heteroaryl or substituted heteroaryl; and
one of R$^1$, R$^2$, R$^3$, R$^4$ or R$^5$ is azido and one of R$^1$, R$^2$, R$^3$, R$^4$ or R$^5$ is optionally a molecule of interest; and (b) a compound of formula (II):

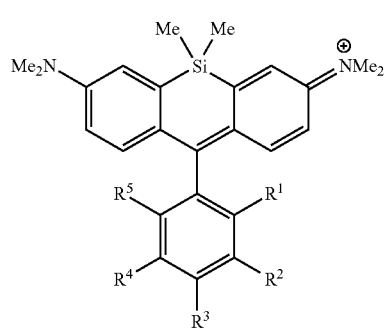

(II)

wherein:
R$^1$ is —OR$^{12}$;
R$^3$ is —OR$^{11}$;
R$^4$ is azido;
R$^2$ and R$^5$ are H; and
R$^{11}$ and R$^{12}$ are each independently hydrogen, an alkyl, a substituted alkyl, a PEG, a zwitterionic group or a water solubilizing group (WSG);
wherein said contacting results in covalent linkage of the compound with the alkyne moiety of the target biomolecule.

16. The method of claim 15, wherein the target biomolecule is a sugar.

17. The method of claim 16, wherein the sugar is a substrate of sialic acid biosynthesis.

18. The method of claim 16, wherein the sugar is mannosamine or acetylated mannosamine.

19. The method of claim 15, wherein the target molecule is an amino acid.

20. The method of claim 15, wherein said reacting is performed in aqueous conditions.

21. The method of claim 15, wherein said reacting is performed under physiological conditions.

22. The method of claim 15, wherein the target molecule is expressed on a cell surface.

23. A method for labeling a cellular component, the method comprising:
introducing an alkyne moiety into a cellular component, thereby generating an alkyne-modified cellular component; and
contacting a cell comprising the alkyne-modified cellular component with a compound wherein said contacting results in covalent linkage of the compound with the alkyne moiety of the alkyne-modified cellular component, thereby generating a labeled conjugate;
wherein the compound is selected from:
(a) a compound of any one of formulae (II), (IV) and (V),

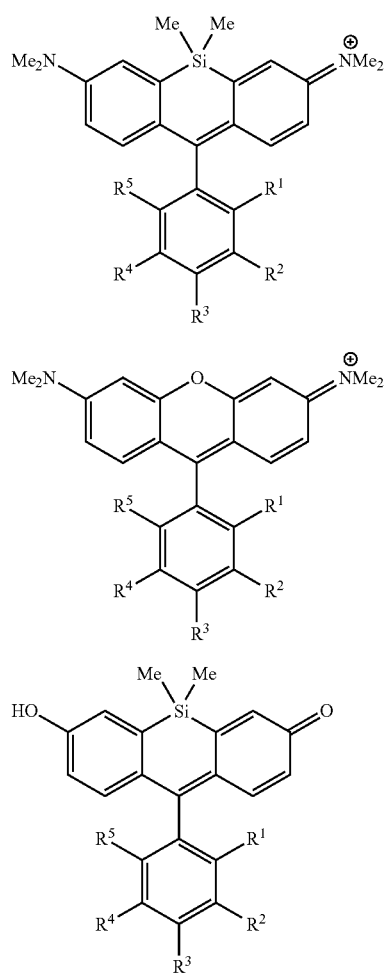

wherein $R^1$, $R^2$, $R^3$, $R^4$ and $R^5$ are each independently selected from the group consisting of hydrogen, alkyl, substituted alkyl, alkoxy, substituted alkoxy, azido, amino, substituted amino, nitro, cyano, acyl, carboxyl, carboxylester, cycloalkyl, substituted cycloalkyl, heterocycloalkyl, substituted heterocycloalkyl, aryl, substituted aryl, heteroaryl, and substituted heteroaryl;
optionally, one of $R^1$, $R^2$, $R^3$, $R^4$ or $R^5$ together with its adjacent R-group form a cycloalkyl, substituted cycloalkyl, heterocycloalkyl, substituted heterocycloalkyl, aryl, substituted aryl, heteroaryl or substituted heteroaryl; and
one of $R^1$, $R^2$, $R^3$, $R^4$ or $R^5$ is azido and one of $R^1$, $R^2$, $R^3$, $R^4$ or $R^5$ is optionally a molecule of interest; and
(b) a compound of formula (II):

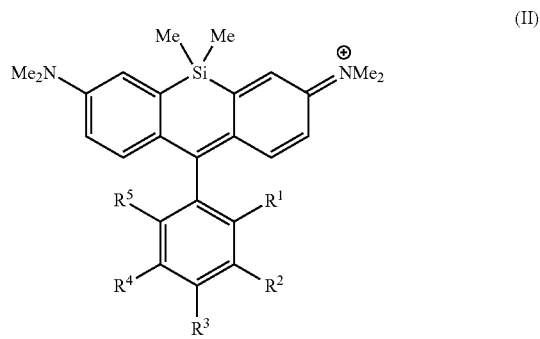

wherein:
$R^1$ is —$OR^{12}$;
$R^3$ is —$OR^{11}$;
$R^4$ is azido;
$R^2$ and $R^5$ are H; and
$R^{11}$ and $R^{12}$ are each independently hydrogen, an alkyl, a substituted alkyl, a PEG, a zwitterionic group or a water solubilizing group (WSG).

24. The method of claim 23, wherein said cellular component comprises an amino acid, a fatty acid, or a sugar that is modified with the alkyne moiety.

25. The method of claim 23, wherein said cellular component is a polypeptide.

26. The method of claim 23, wherein said cellular component is a lipid.

27. The method of claim 23, wherein said cellular component is a polysaccharide.

28. The method of claim 23, wherein said contacting is in vitro or in vivo.

29. The method of claim 23, wherein said contacting is under physiological conditions.

30. The method of claim 23, further comprising detecting the labeled conjugate.

31. The method of claim 30, wherein the cell is not washed prior to said detecting.

32. The method of claim 23, wherein the cell is a prokaryotic cell.

33. The method of claim 23, wherein the cell is a eukaryotic cell.

34. The compound of claim 1, wherein one of $R^1$, $R^2$, $R^3$, $R^4$ or $R^5$ is a molecule of interest.

35. The method of claim 15, wherein in formulae (II), (IV) and (V), one of $R^1$, $R^2$, $R^3$, $R^4$ or $R^5$ is a molecule of interest.

36. The method of claim 23, wherein in formulae (II), (IV) and (V), one of $R^1$, $R^2$, $R^3$, $R^4$ or $R^5$ is a molecule of interest.

* * * * *